US011638709B2

(12) United States Patent
Wolff-Winiski et al.

(10) Patent No.: US 11,638,709 B2
(45) Date of Patent: May 2, 2023

(54) RUCAPARIB, TALAZOPARIB, VELIPARIB, OLAPARIB AND AZD 2461 FOR TREATING IMPAIRED SKIN WOUND HEALING

(71) Applicant: AKRIBES BIOMEDICAL GMBH, Vienna (AT)

(72) Inventors: Barbara Wolff-Winiski, Vienna (AT); Anton Stütz, Altmünster (AT); Petra Dörfler, Brunn am Gebirge (AT)

(73) Assignee: AKRIBES BIOMEDICAL GMBH, Vienna (AT)

( * ) Notice: Subject to any disclaimer, the term of this patent is extended or adjusted under 35 U.S.C. 154(b) by 0 days.

(21) Appl. No.: 16/607,611

(22) PCT Filed: Apr. 24, 2018

(86) PCT No.: PCT/EP2018/060435
§ 371 (c)(1),
(2) Date: Oct. 23, 2019

(87) PCT Pub. No.: WO2018/197463
PCT Pub. Date: Nov. 1, 2018

(65) Prior Publication Data
US 2020/0078369 A1   Mar. 12, 2020

(30) Foreign Application Priority Data
Apr. 28, 2017   (EP) .................................... 17000743

(51) Int. Cl.
| A61P 17/02 | (2006.01) |
| A61K 31/375 | (2006.01) |
| A61K 31/573 | (2006.01) |
| A61K 31/55 | (2006.01) |
| A61K 31/4184 | (2006.01) |
| A61K 31/502 | (2006.01) |
| A61K 31/5025 | (2006.01) |
| G01N 33/50 | (2006.01) |

(52) U.S. Cl.
CPC .......... A61K 31/55 (2013.01); A61K 31/4184 (2013.01); A61K 31/502 (2013.01); A61K 31/5025 (2013.01); A61P 17/02 (2018.01); G01N 33/5044 (2013.01)

(58) Field of Classification Search
CPC .... A61K 31/375; A61K 31/573; A61K 38/18; A61K 45/06; A61P 17/02
See application file for complete search history.

(56) References Cited

U.S. PATENT DOCUMENTS

2009/0263407 A1\* 10/2009 Dande .................. C07D 317/28
514/1.1
2020/0129476 A1   4/2020 Wolff-Winiski et al.

FOREIGN PATENT DOCUMENTS

WO   2001042219 A2   6/2001

OTHER PUBLICATIONS

Ahmad et al. ("The clinically used PARP inhibitor olaparib improves organ function, suppresses inflammatory responses and accelerates wound healing in a murine model of third-degree burn injury." British Journal of Pharmacology; 175(2):232-245. https://doi.org/10.1111/bph.13735. First published Feb. 1, 2017 (Year: 2017).\*
Kirker et al. ("In vitro studies evaluating the effects of biofilms on wound-healing cells: a review." APMIS 2017; 125: 344-352). (Year : 2017).\*
of El-Hamoly et al. (Mol Med. 2014; 20(1): 363-371). (Year: 2014).\*
Thorsell et al. (J. Med Chem. Feb. 23, 2017; 60(4): 1262-1271. doi:10.1021/acs.jmedchem.6b00990.) (Year: 2017).\*
Phillips et al. ("Effect of chronic wound fluid on fibroblasts." Journal of Wound Care vol. 7, No. 10 | Published Online: Dec. 12, 2016 . https://doi.org/10.12968/jowc.19987.10.527.) (Year: 2016).\*
Mendez et al. (Journal of Vascular Surgery vol. 30, Issue 4, Oct. 1999, pp. 734-743). (Year: 1999).\*
Ahmad et al., "The clinically used PARP inhibitor olaparib improves organ function, suppresses inflammatory responses and accelerates wound healing in a murine model of third-degree burn injury," British Journal of Pharmacology, 2017, vol. 175, pp. 232-245.
Asmussen et al., "The angiotensin-converting enzyme inhibitor captopril inhibits poly(ADP-ribose) polymerase activation and exerts beneficial effects in an ovine model of burn and smoke injury," Shock, 2011, vol. 36, No. 4, pp. 402-409.
Bosanquet et al., "Topical steroids for chronic wounds displaying abnormal inflammation," Annals of the Royal College of Surgeons of England, 2013, vol. 95, Iss. 4, pp. 291-296.
Byun et al., "Poly(ADP-ribose) polymerase inhibition improves corneal epithelial innervation and wound healing in diabetic rats," Investigative Opthalmology & Visual Science, 2015, vol. 56, No. 3, pp. 1948-1955.
Dissemond et al., "Modern wound care—practical aspects of non-interventional topical treatment of patients with chronic wounds," Journal of the German Society of Dermatology (JDDG), 2014, vol. 12, Iss. 7, pp. 541-554.
El-Hamoly et al., "Activation of poly(ADP-ribose) polymerase-1 delays wound healing by regulating keratinocyte migration and production of inflammatory mediators," Molecular Medicine, 2014, vol. 20, No. 1, pp. 363-371.
Farkas et al., "Reduction of acute photodamage in skin by topical application of a novel PARP inhibitor," Biochemical Pharmacology, 2002, vol. 63, Iss. 5, pp. 921-932.

(Continued)

Primary Examiner — Jeffrey S Lundgren
Assistant Examiner — Chris E Simmons
(74) Attorney, Agent, or Firm — Melissa Hunter-Ensor; Evelyn Kwon; Greenberg Traurig, LLP

(57) ABSTRACT

The present invention relates to Rucaparib and/or Talazoparib and/or Veliparib and/or Olaparib, and/or AZD 2461, or a pharmaceutically acceptable salt thereof, for use in the treatment of impaired skin wound healing in a subject, an in vitro method for identifying a subject suffering from impaired skin wound healing to be responsive to the treatment with Rucaparib and/or Talazoparib and/or Veliparib and/or Olaparib and/or AZD 2461, and kits and kits-of-part related thereto.

12 Claims, 24 Drawing Sheets

(56) References Cited

OTHER PUBLICATIONS

Figure 1:
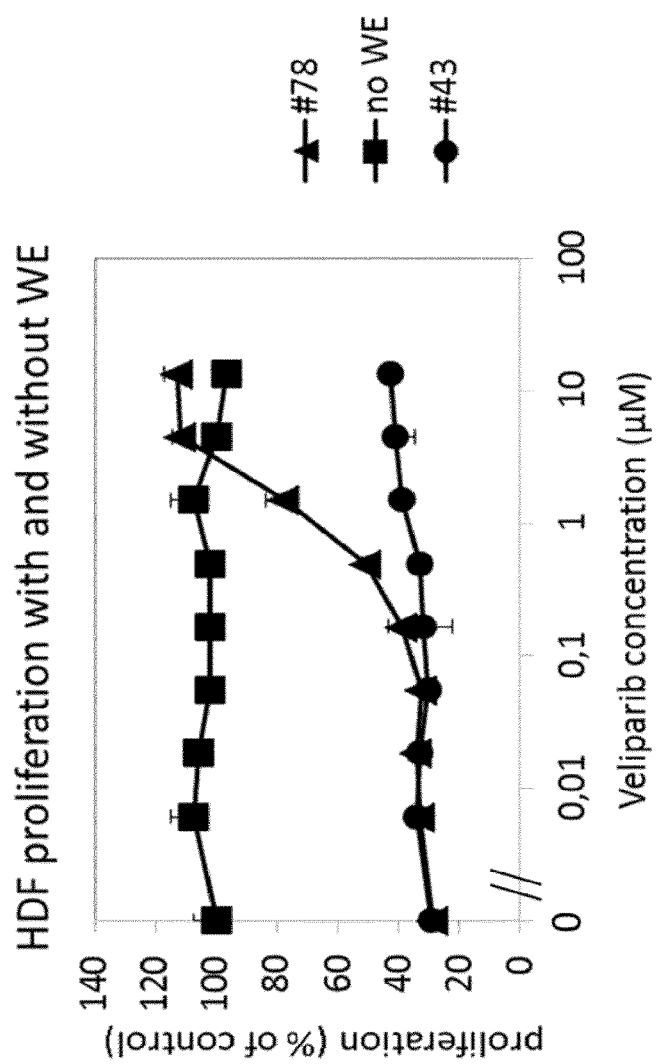

Gottrup, Finn, "A specialized wound-healing center concept: importance of a multidisciplinary department structure and surgical treatment facilities in the treatment of chronic wounds," The American Journal of Surgery, 2004, vol. 187, Iss. 5, Suppl. 1, pp. 38S-43S.
Sarras et al., "Inhibition of poly-ADP ribose polymerase enzyme activity prevents hyperglycemia-induced impairment of angiogenesis during wound healing," Wound Repair and Regeneration, 2014, vol. 22, Iss. 5, pp. 666-670.
Thorsell et al., "Structural Basis for Potency and Promiscuity in Poly(ADP-ribose) Polymerase (PARP) and Tankyrase Inhibitors," Journal of Medicinal Chemistry, 2017, vol. 60, Iss. 4, pp. 1262-1271 and supplemental pp. 1-18.
Virág et al., "The therapeutic potential of poly(ADP-ribose) polymerase inhibitors," Pharmacological Reviews, 2002, vol. 54, No. 3, pp. 375-429.
Wang et al., "Discovery and Characterization of (8S,9R)-5-Fluoro-8-(4-fluorophenyl)-9-(1-methyl-1H-1,2,4-triazol-5-yl)-2,7,8,9-tetrahydro-3H-pyrido[4,3,2-de]phthalazin-3-one (BMN 673, Talazoparib), a Novel, Highly Potent, and Orally Efficacious Poly(ADP-ribose) Polymerase-1/2 Inhibitor, as an Anticancer Agent," Journal of Medicinal Chemistry, 2016, vol. 59, Iss. 1, pp. 335-357 and supplemental pp. 1-20.
El-Hamoly et al., "3-aminobenzamidem a poly (ADP ribose) polymerase inhibitor, enhances wound healing in whole body gamma irradiated model: PARP inhibition & gamma irradiated wounds," Wound Repair and Regeneration., vol. 23, No. 5, 2015, pp. 672-684, XP055414446, ISSN: 1067-1927, DOI: 10.1111/wrr.12330 cited in the application: the whole document abstract, discussion.
Hengge et al., "Adverse effects of topical glucocorticosteroids," Journal of the American Academy of Dermatology, vol. 54, No. 1, 2006, pp. 1-15, XP005219461, ISSN: 0190-9622, DOI: 10.1016/J.JAAD.2005.01.010 cited in the application: the whole document abstract, conclusions, delayed wound healing (p. 8, right-hand column, last paragraph).
Zhou et al., "Poly-ADP-ribose polymerase inhibition enhances ischemic and diabetic wound healing by promoting angiogenesis," Journal of Vascular Surgery, vol. 65, No. 4, Jun. 8, 2016 (Jun. 8, 2016), pp. 1161-1169, XP085097852, ISSN: 0741-5214, DOI: 10.1016.J.JVS.2016.03.407 cited in the application: the whole document abstract, discussion, conclusions.
International Search Report and Written Opinion for corresponding PCT Patent Application No. PCT/EP2018/060429, dated Aug. 13, 2018 (14 pages).

* cited by examiner

A)

B)

A)

B)

C)

D)

A)

B)

C)

F)

RUCAPARIB, TALAZOPARIB, VELIPARIB, OLAPARIB AND AZD 2461 FOR TREATING IMPAIRED SKIN WOUND HEALING

This application is the U.S. national phase application, pursuant to 35 U.S.C. § 371, of PCT International Application Ser. No.: PCT/EP2018/060435, filed Apr. 24, 2018, designating the United States and published in English, which claims the benefit of European Patent Application No. 17000743.9, filed Apr. 28, 2017, each of which is incorporated herein by reference in its entirety.

The present invention relates to Rucaparib and/or Talazoparib and/or Veliparib and/or Olaparib, and/or AZD 2461, or a pharmaceutically acceptable salt thereof, for use in the treatment of impaired skin wound healing in a subject, an in vitro method for identifying a subject suffering from impaired skin wound healing to be responsive to the treatment with Rucaparib and/or Talazoparib and/or Veliparib and/or Olaparib and/or AZD 2461, and kits and kits-of-part related thereto.

Chronic wounds are a major health issue worldwide with 5.7 million affected patients in the US alone and an expected increase due to the aging population and growing incidence of metabolic diseases.

Chronic wounds have a multifactorial etiology and are dependent on different variables: a) underlying disease, e.g. diabetes, arterial or venous insufficiency, b) pressure, c) age and nutritional status and d) microbial environment.

Chronic wounds are generally understood as those wounds that have not healed within 2 months. They are a major health issue worldwide. In developed countries, including the US and the EU, it has been estimated that 1 to 2% of the total population will experience a chronic wound during their lifetime [Gottrup F (2004) Am J Surg 187:38S-43S].

The major chronic wound indications are venous ulcers, pressure ulcers and diabetic foot ulcers. Venous ulcers are defects in pathologically altered tissue on the lower leg based on chronic venous insufficiency, often accompanied by deep venous thrombosis. Pressure ulcers are the results of severe tissue hypoxemia in immobilized patients. Diabetic foot ulceration can affect up to 25% of patients with diabetes throughout their lifetime and often results in lower limb amputation. The standard of care for all of these wounds, as recommended by the German Society for Dermatology [Dissemond J et al (2014) JDDG 1610-0379/2014/1207:541-554] includes wound dressings, surgical and biological (maggot) debridement, infection control and negative pressure therapy. Regranex® (PDGF: platelet-derived growth factor) was the only registered pharmacological treatment for a long time, but its therapeutic efficacy is minor, as is the success of cell-based therapies. Recombinant human EGF (rhEGF) is registered as Heberprot-P® in several countries for treating ulcerations in the diabetic foot ulcus syndrome. Moreover, Trafermin (brand name: Fiblast®), also known as recombinant human basic fibroblast growth factor (rhbFGF), is a recombinant form of human basic fibroblast growth factor (bFGF) which is marketed in Japan as a topical spray for the treatment of skin ulcers.

Recurrence is a problem in one third of all chronic wounds, regardless of their treatment.

Even though they are anti-inflammatory in other settings, topical glucocorticoids cannot be used because one of their side effects is actually delayed wound healing [Hengge U R (2006) J Am Acad Dermatol 54:1-15]. Therefore, as a "dogma" in the prior art, topical glucocorticoids are described to impair wound healing. Further, non-steroidal anti-inflammatory drugs, e.g. ibuprofen, are only effective in ameliorating wound pain [Dissemond J et al (2014), supra].

There is therefore an ongoing and strong medical need for reliable and effective therapies for the treatment of impaired skin wound healing in patients.

It was surprisingly found in the present application, as shown in the examples and corresponding Figures, that the following selective Poly(ADP-ribose)polymerase (PARP) inhibitors a) to e) exhibit an outstanding fibroblast proliferation (2D) enhancing and fibroblast derived matrix formation (3D) enhancing effect, using wound exudates from chronic wound patients:

a) Rucaparib,
b) Talazoparib,
c) Veliparib,
d) Olaparib,
e) AZD 2461.

The fibroblast proliferation assay (2D) and the fibroblast derived matrix formation assay (3D) are predictive assays for wound healing.

Poly(ADP-ribose)polymerase (PARP) or poly(ADP-ribose)synthase (PARS) is a nuclear enzyme that has an essential role in recognizing DNA damage, facilitating DNA repair, controlling RNA transcription, mediating cell death, and regulating immune response. PARP activity is required for the repair of single-stranded DNA breaks through the base excision repair pathways. Cancer cells are often deficient in double-stranded DNA-repair capability, and are therefore more dependent on PARP directed single-stranded DNA-repair than are normal cells. Consequently, inhibition of PARP by specific PARP inhibitors has been described in the art to enhance the antitumor effects of DNA-damaging agents in cancer cells.

Further, there have been few reports on an enhancing effect of certain other specific PARP inhibitors in very specific models in the broadest context of wound healing (Farkas B et al (2002) Reduction of acute photodamage in skin by topical application of a novel PARP inhibitor. Biochem Pharmacol 63:921-932; Zhou X et al (2016) Poly-ADP-ribose polymerase inhibition enhances ischemic and diabetic wound healing by promoting angiogenesis. J Vasc Surg, doi 10.1016/j.jvs.2016.03.407; Byun Y-S et al (2015) Poly(ADP-ribose) polymerase inhibition improves corneal epithelial innervation and wound healing in diabetic rats. Invest Ophthalmol Vis Sci 56:1948-1955; El-Hamoly T et al (2015) 3-aminobenzaminde, a poly (ADP ribose) polymerase inhibitor, enhances wound healing in whole body gamma irradiated model. Wound Rep Reg 23:672-684; El-Hamoly T et al (2014) Activation of poly (ADP ribose) polymerase-1 delays wound healing by regulating keratinocyte migration and production of inflammatory mediators. Mol Med 20:363-371; Sarras M P (2014) Inhibition of poly-APD ribose polymerase enzyme activity prevents hyperglycemia-induced impairment of angiogenesis during wound healing. Wound Rep Reg 22:666-670; Virag L & Szabo C (2002) The therapeutic potential of poly (ADP ribose) polymerase inhibitors. Pharmacol Rev 54:375-429; Asmussen S et al (2011) The angiotensin-converting enzyme inhibitor captopril inhibits poly(ADP-ribose)polymerase activation and exerts beneficial effects in an ovine model of burn and smoke injury. Shock 3: 402-409; Thorsell A G (2016) Structural Basis for Potency and Promiscuity in Poly(ADP-ribose) Polymerase (PARP) and Tankyrase Inhibitors. J Med Chem 59:335-357; WO 01/42219 A2; Zhou X et al (2017) Poly-ADP-ribose polymerase inhibition enhances ischemic and diabetic wound healing by promoting angiogenesis. J Vasc Surg 65:1161-1169). Further, there has been a report for olaparib with limited predictability (Akbar A et al (2017) The clinically used poly (ADP ribose) polymerase (PARP) inhibitor olaparib improves organ function, suppresses inflammatory responses and accelerates wound healing in a murine model of third-degree burn injury. Br J Pharmacol doi: 10.1111/bph.13735).

However, the predictability of these reports for clinical efficacy is very limited. Further, Rucaparib, Talazoparib, Veliparib, Olaparib or AZD 2461 have not been investigated so far in clinical studies of wound healing or using patient tissues.

It was surprisingly found that the PARP inhibitor veliparib completely reversed inhibition of wound exudate (WE)-induced fibroblast proliferation for wound exudate from a diabetic patient in the proprietary and predictive assay system in Example 1 (Example 1.1, FIG. 1). The effect of veliparib could be confirmed in a number of further wound exudate samples from other patients.

Figure 2:
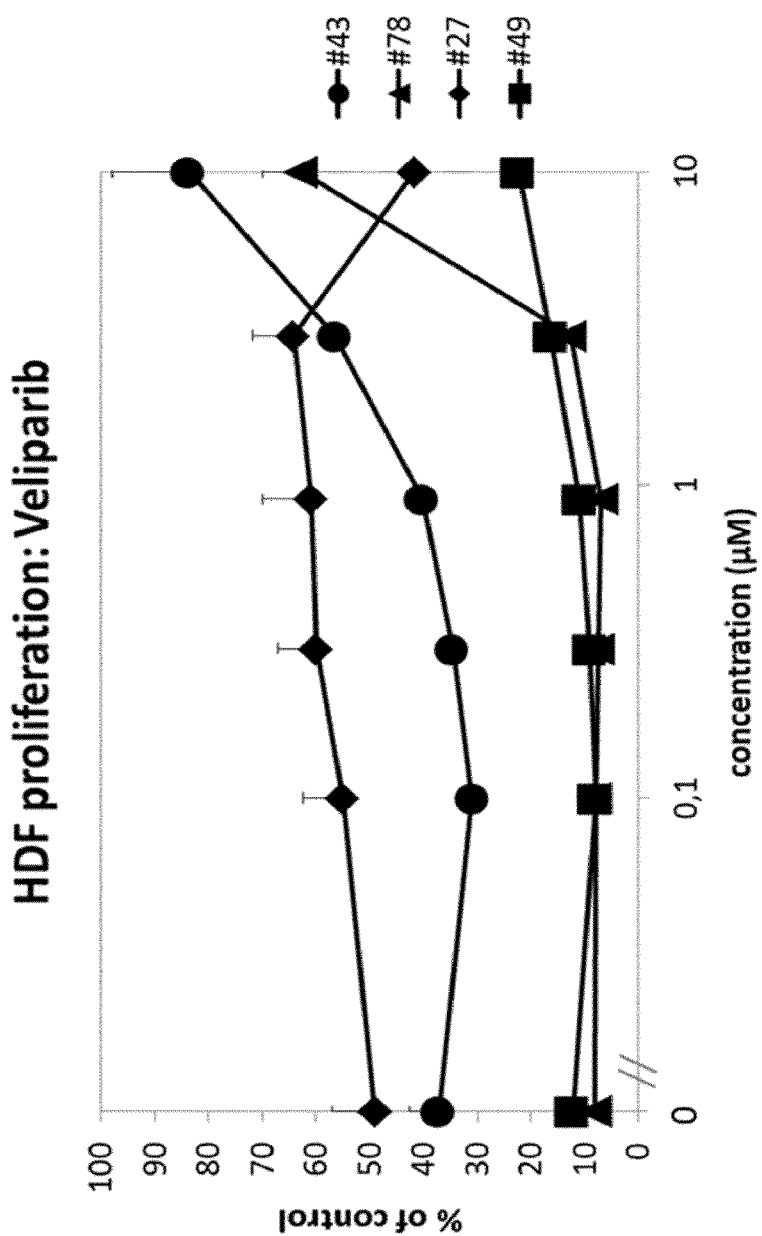
Figure 3:
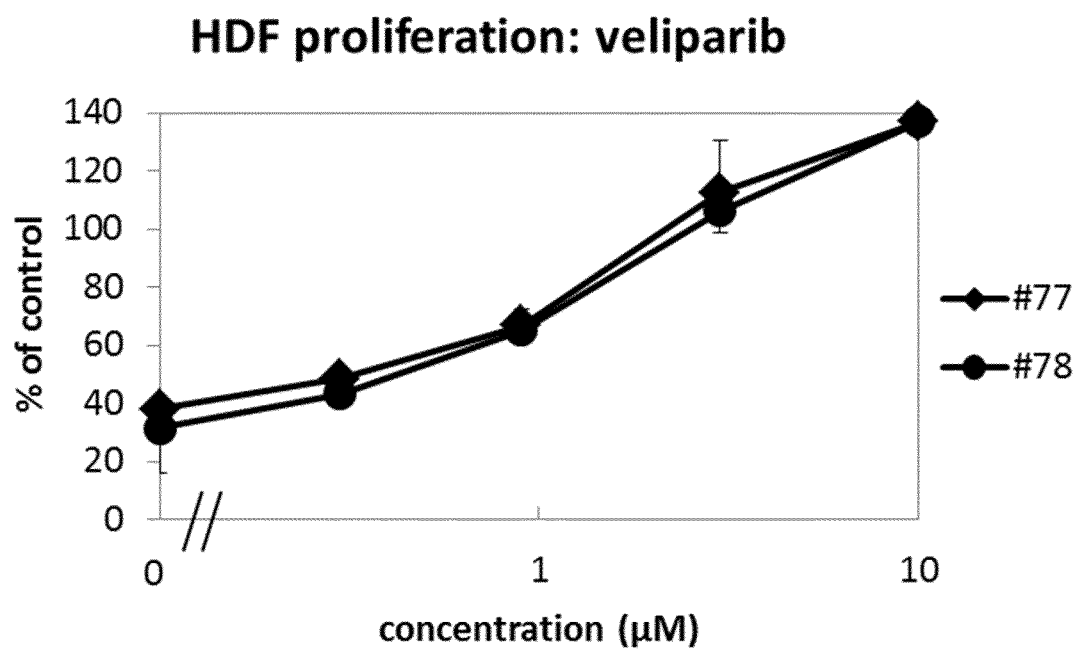

The effect of veliparib was further most prominent in patients with diabetes (FIG. 2). Moreover, the effect of veliparib was reproducible in different samples of the same patient (FIG. 3). Remarkably, said patient received a glucocorticoid, namely prednisolone, as co-medication.

Figure 7:
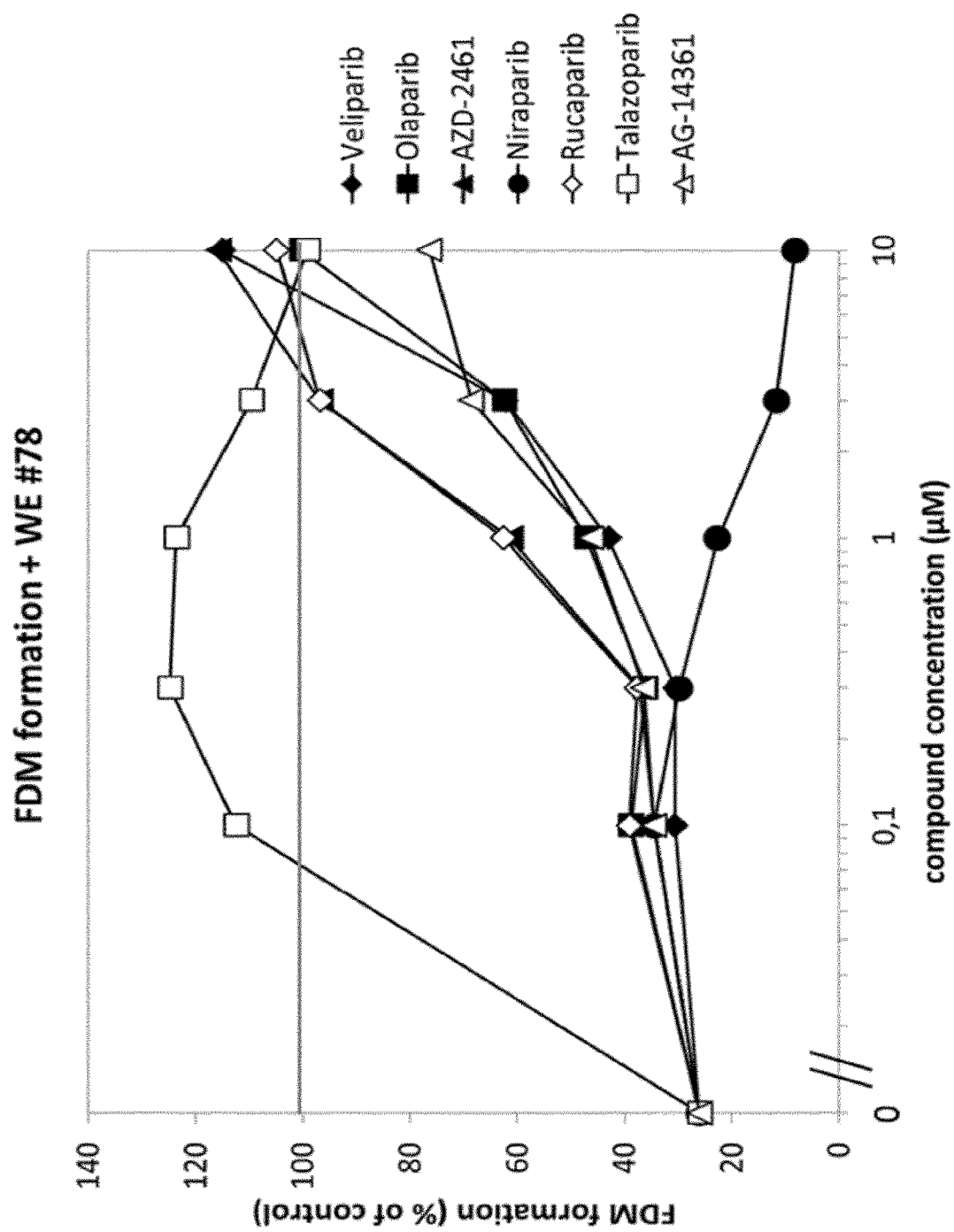
Figure 8:
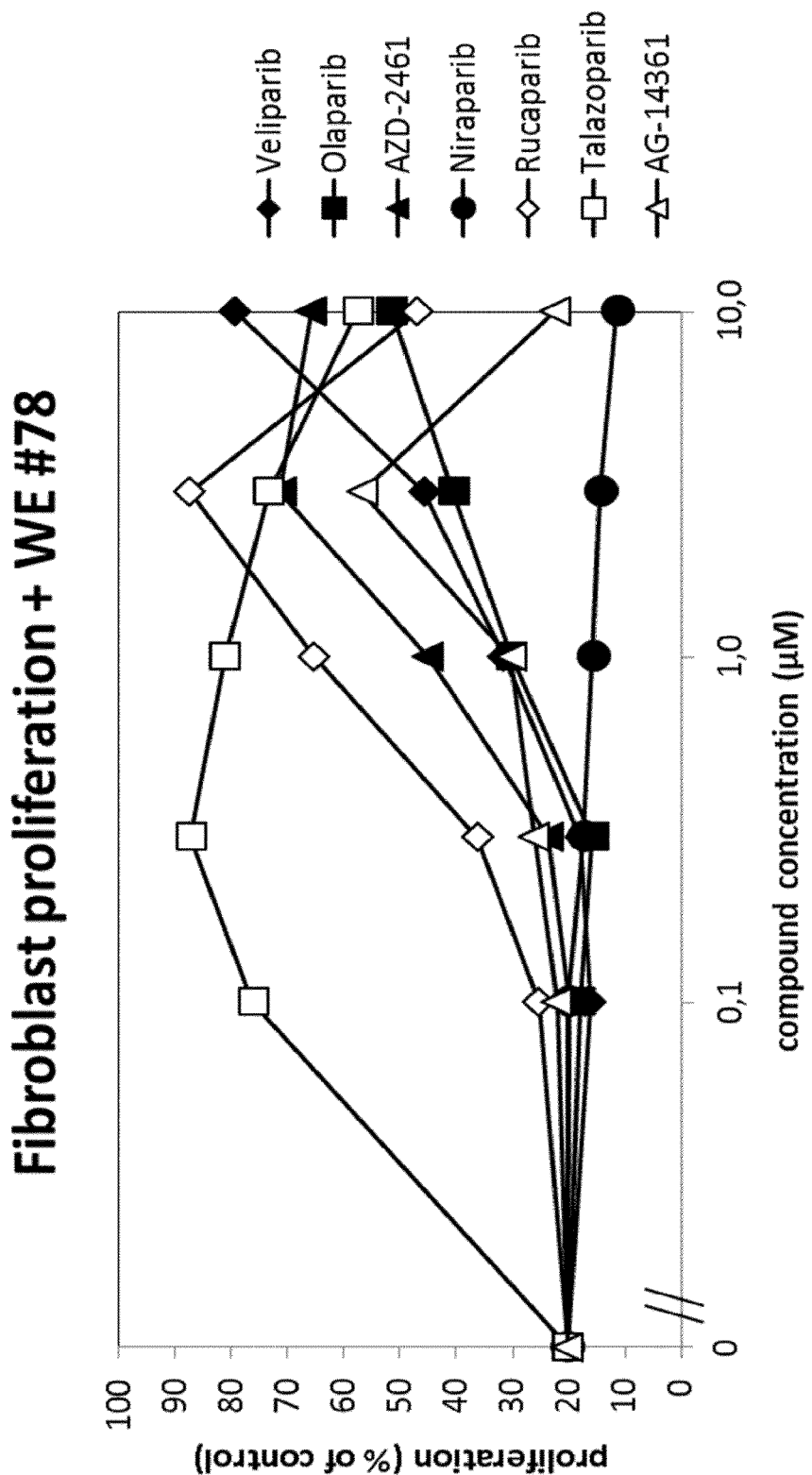

Further, only Rucaparib, Talazoparib, Veliparib, Olaparib and AZD 2461 surprisingly exhibited a strong enhancing effect in the fibroblast-derived matrix (also called FDM or 3D FDM) formation assay (FIG. 7). The strong positive effect of only Rucaparib, Talazoparib, Veliparib, Olaparib and AZD 2461 could be confirmed in the 2D fibroblast proliferation assay (FIG. 8).

Surprisingly, niraparib, which inhibits both PARP1 and PARP with an 1050 in the low nM range, does not show any activity in the assays. Also, AG-14351, which inhibits PARP1 with an 1050 in the low nM range, exhibits only a very weak effect at a concentration of 10 µM.

Figure 9:
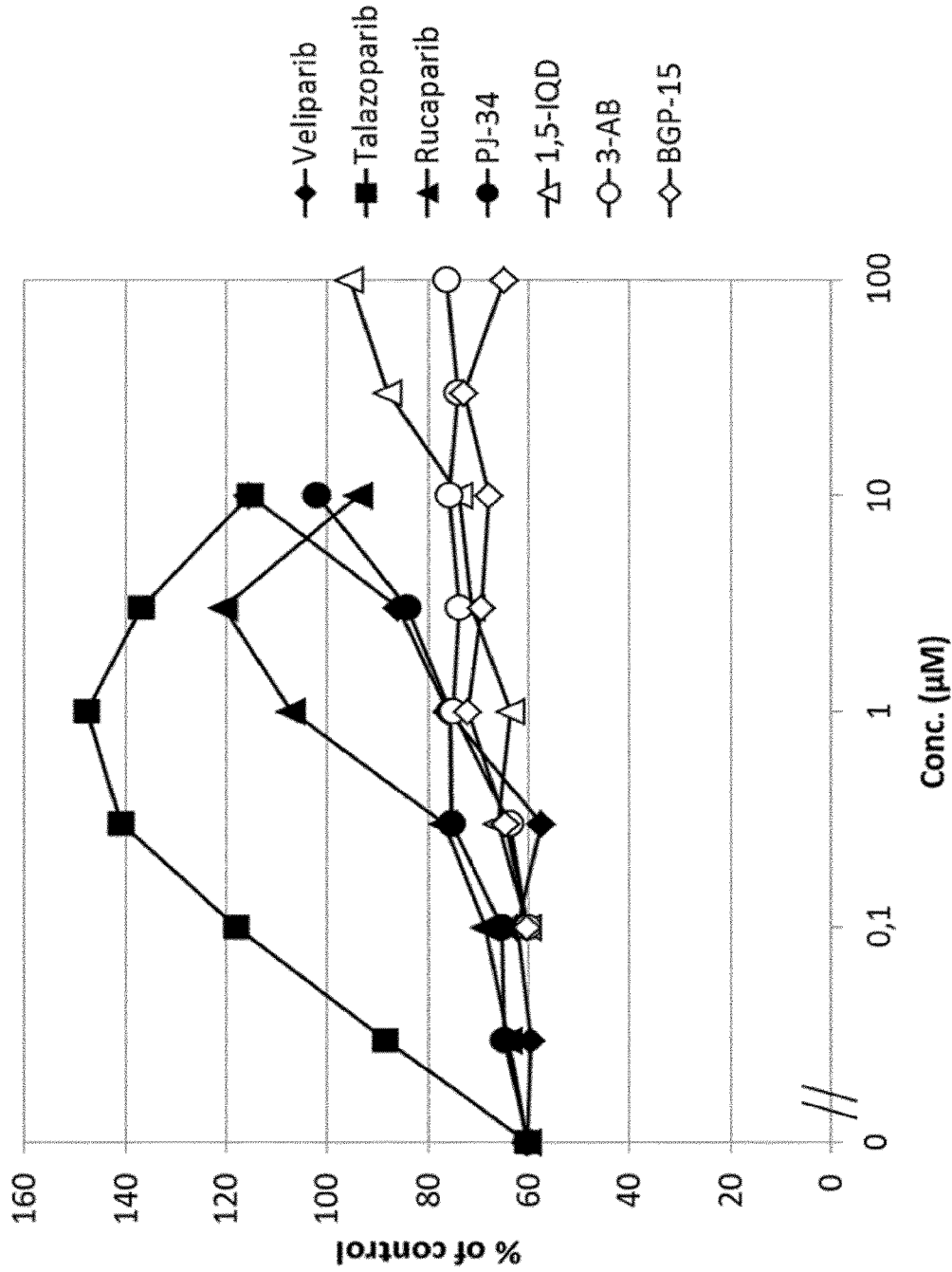
Figure 10:
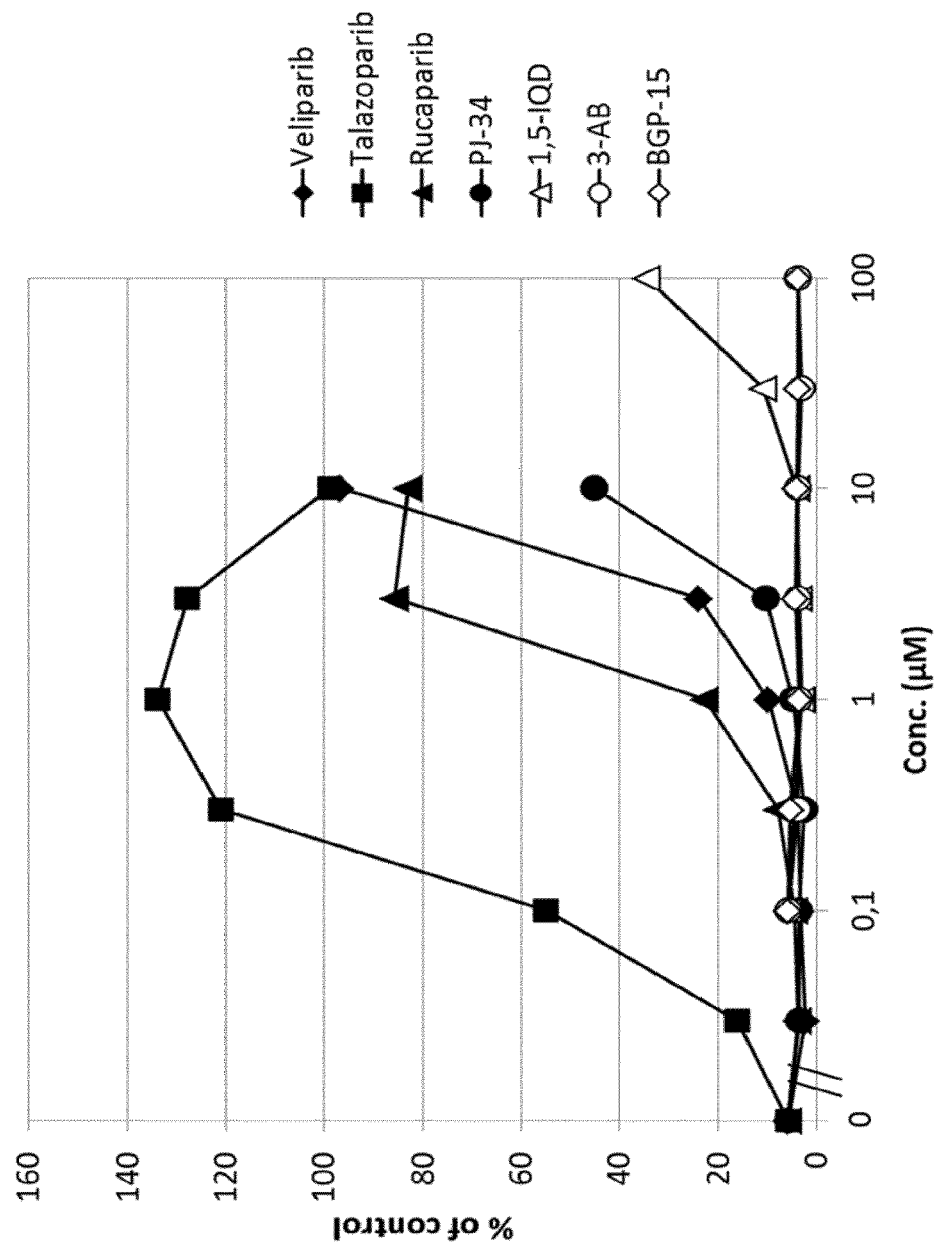

Moreover, still other PARP inhibitors, namely BGP-15, 3-AB, 1,5-IQD and PJ-34, were found to be either inactive or only weakly active in both the 2D fibroblast proliferation assay and the 3D fibroblast-derived matrix formation assay (FIGS. 9 and 10).

To sum up, niraparib, AG-14361, BGP-15, 3-AB, 1,5-IQD and PJ-34 were found to be either inactive or to exhibit only a weak effect in the assays. Notably, inactive compounds include niraparib, which inhibits both PARP1 and PARP with an 1050 in the low nM range. Also, AG-14351, which inhibits PARP1 with an 1050 in the low nM range shows weak activity at 10 µM.

Figure 11:
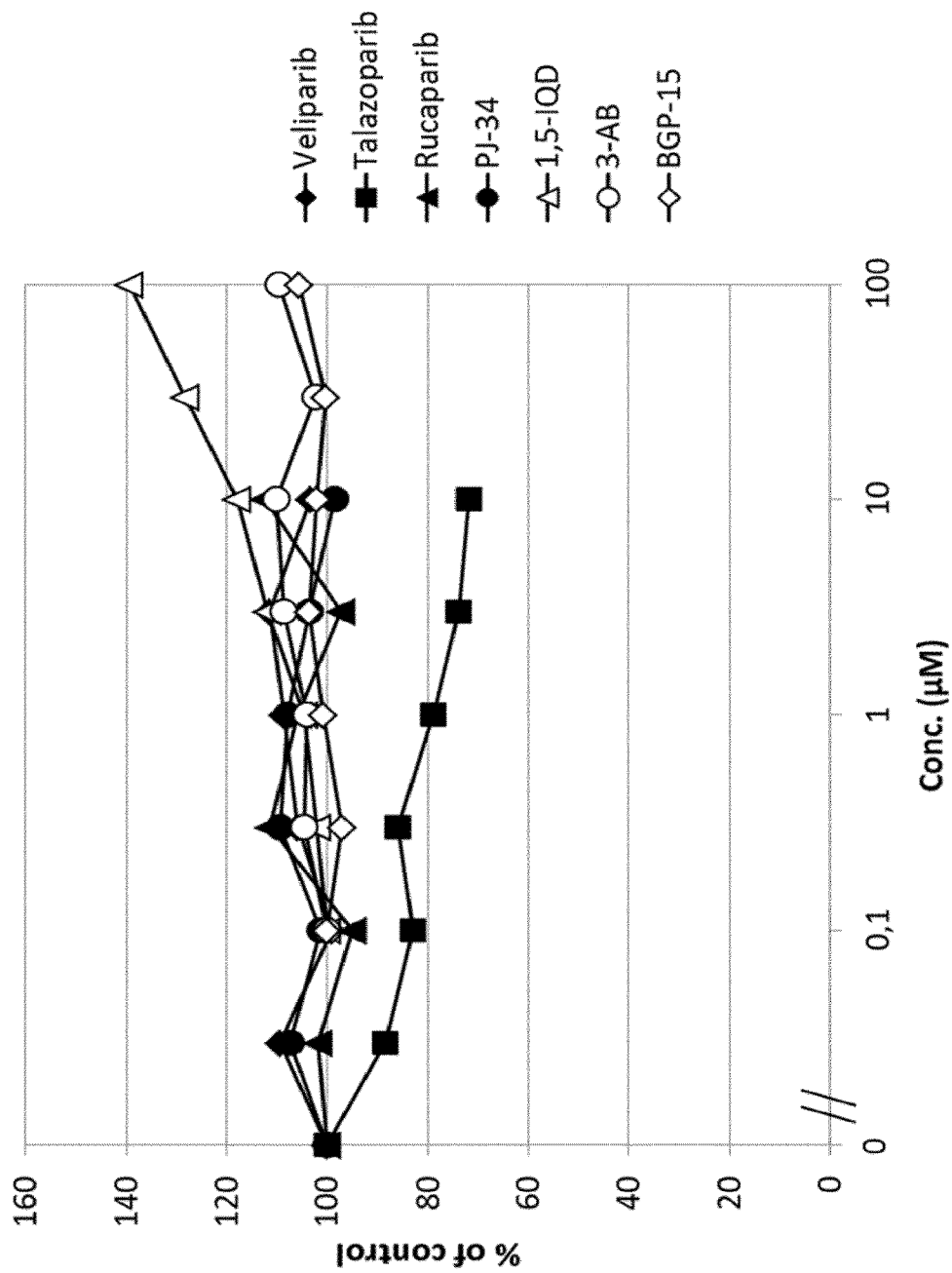

Remarkably, the PARP inhibitors Rucaparib, Talazoparib, Veliparib, Olaparib and AZD 2461 have either no effect on fibroblast proliferation in the absence of wound exudate, or only a marginal effect (FIG. 11). Therefore, it was unexpected to identify the strongly beneficial effect in the context of impaired wound healing for these specific compounds.

Moreover, as indicated above, the experimental results surprisingly indicate that Rucaparib, Talazoparib, Veliparib, Olaparib and AZD 2461 are in particular effective in the treatment of impaired wound healing for patients already obtaining glucocorticoids as therapy, such as a therapy of a co-morbidity as well as patients suffering from diabetes, or immunosuppressed patients.

Figure 4:
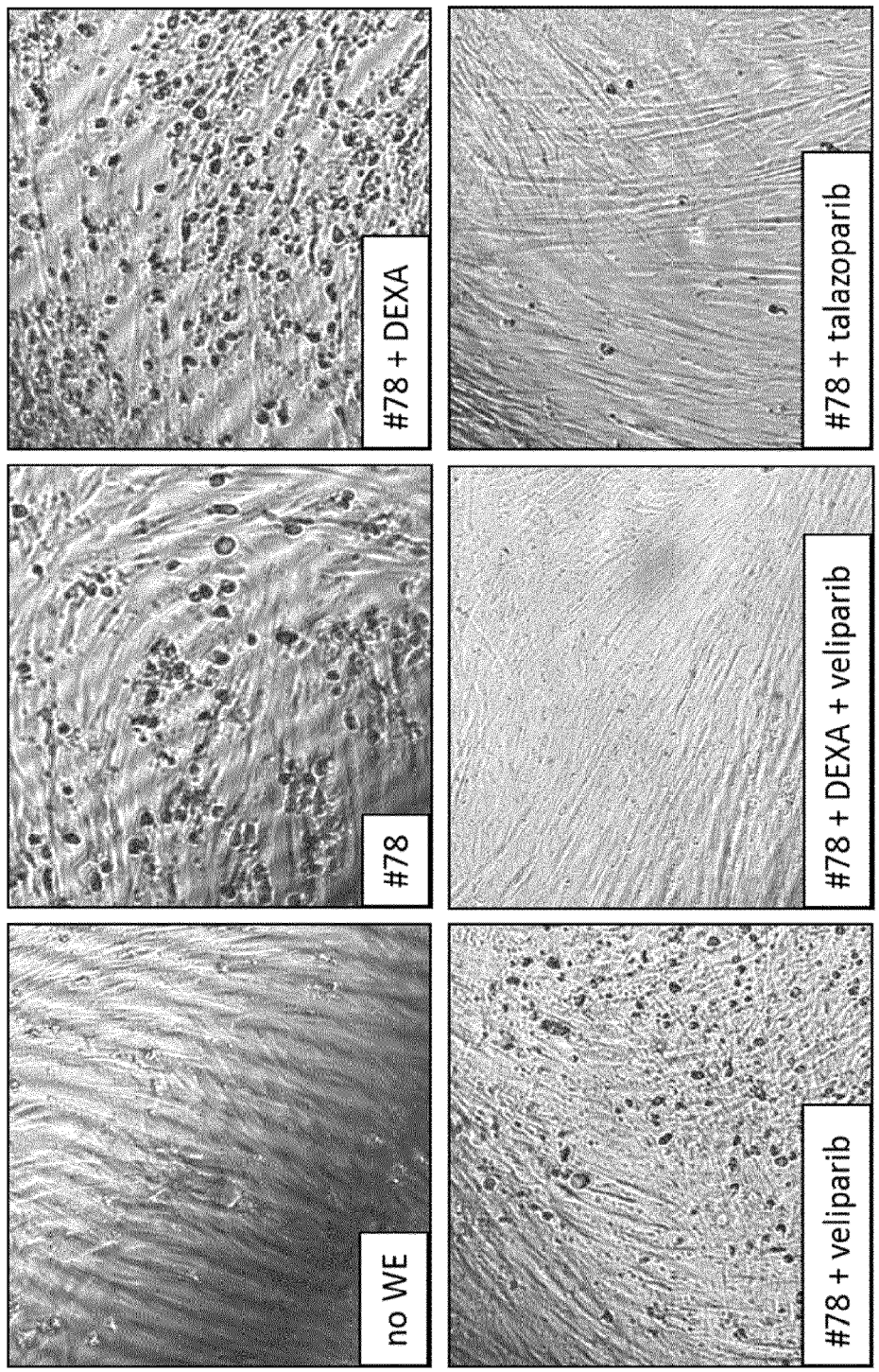

The beneficial effects of Rucaparib, Talazoparib, Veliparib, Olaparib and AZD 2461 for impaired wound healing as well as the synergistic effects of Rucaparib, Talazoparib, Veliparib, Olaparib and AZD 2461 and a glucocorticoid could be further experimentally confirmed. As shown in FIG. 4, talazoparib and veliparib both "cleaned up" WE-induced fibroblast matrix inhibition. Moreover, the combination of veliparib with dexamethasone was even superior to each substance alone, thereby showing a surprising synergistic effect.

Figure 12:
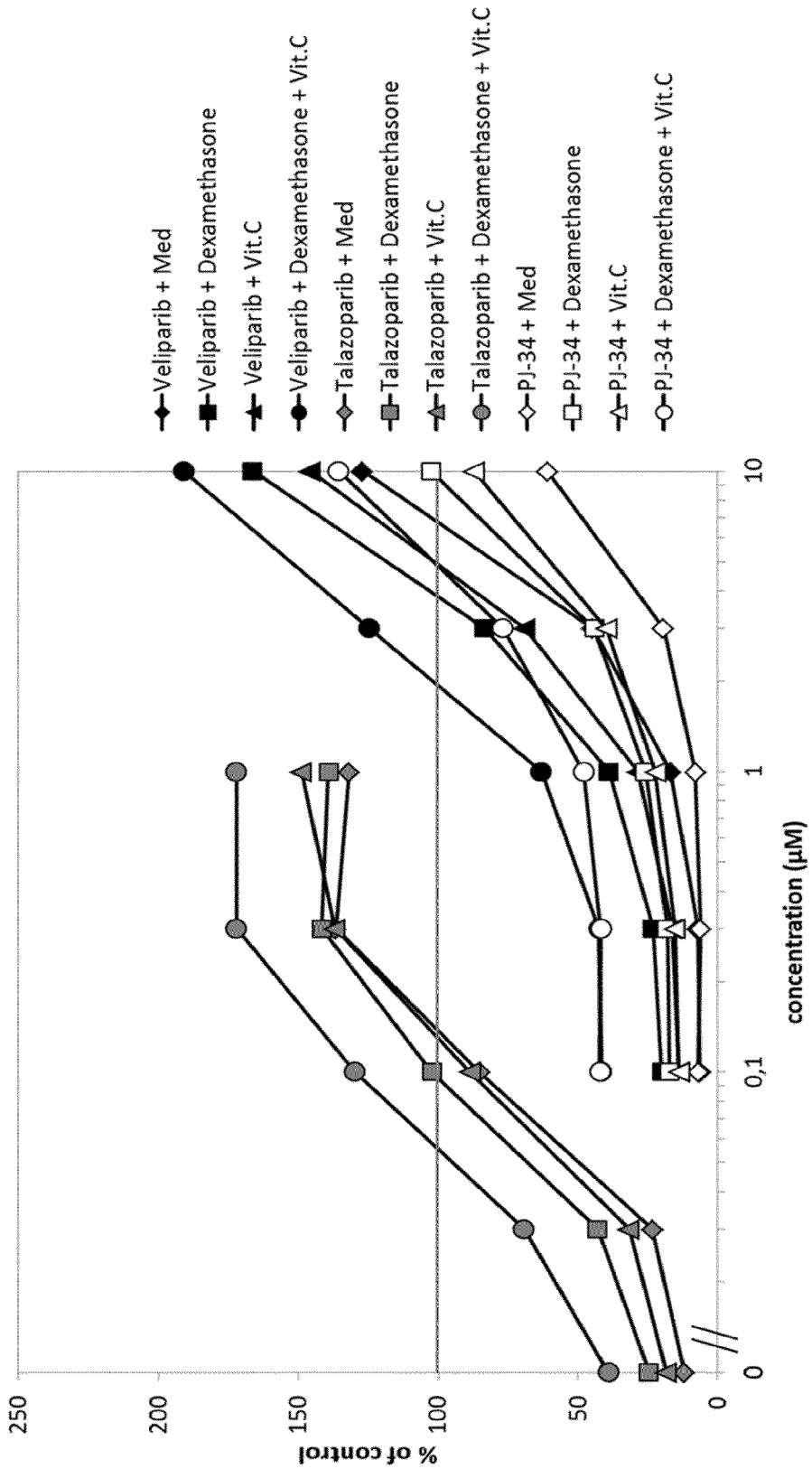

Moreover, it was surprisingly shown in the fibroblast proliferation assay and using titration of Veliparib, talazoparib and PJ-34 with fixed concentrations of dexamethasone (3 nM; suboptimal) and vitamin C (100 µg/ml), that both the glucocorticoid dexamethasone and vitamin C enhance the positive enhancing effect of veliparib and talazoparib, thereby showing a synergistic effect (FIG. 12). PJ-34 again shows only a weak effect.

Therefore, the experimental data confirm that Rucaparib, Talazoparib, Veliparib, Olaparib and AZD 2461 are in particular effective in the treatment of impaired wound healing for patients already obtaining glucocorticoids as therapy, such as a therapy of a co-morbidity and/or ascorbic acid as therapy or as nutritional supplement.

The strong and consistent synergistic effect could be confirmed both for the glucocorticoid and vitamin C and veliparib or talazoparib for a different patient (FIG. 12).

Figure 14:
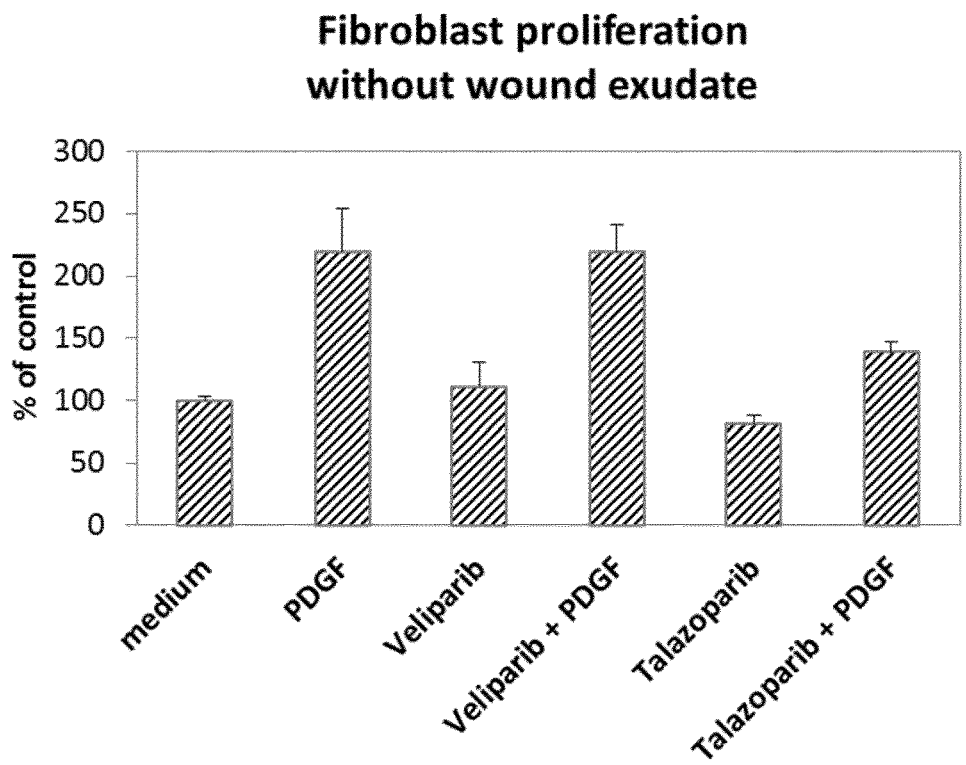
Figure 14:
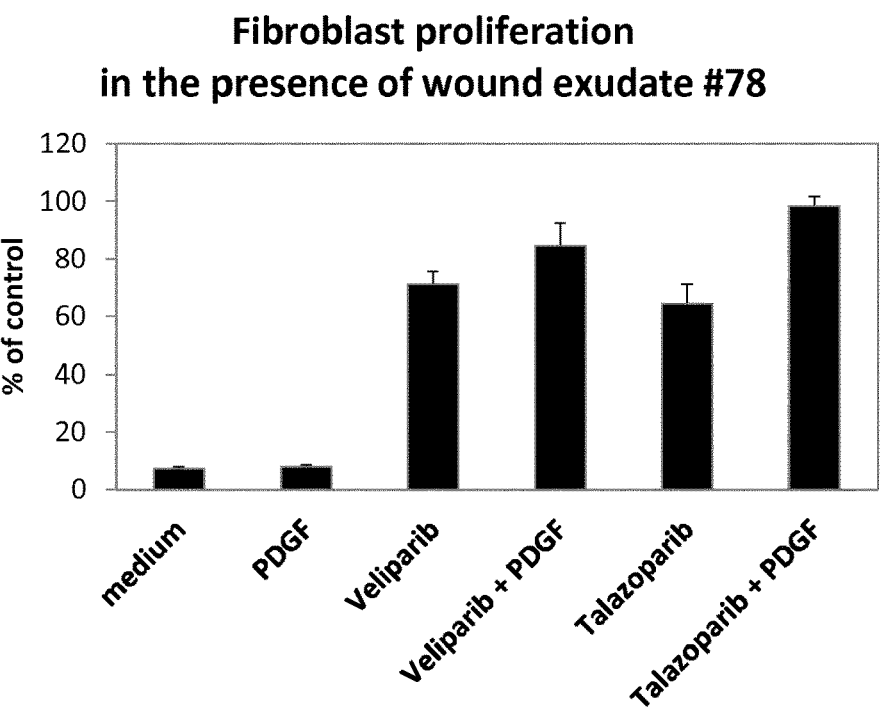

Moreover, it was surprisingly found that, in two separate experiments, the PARP inhibitors veliparib, olaparib, talazoparib and rucaparib showed an enhanced positive effect of recovery of fibroblast proliferation by PDGF in the presence of wound exudate #78 (FIG. 14). This enhancement was shown to depend on the dose of the respective PARP inhibitor. This effect was confirmed in a further wound exudate (#49). This positive additive or synergistic effect is surprising, as PDGF has no effect on the WE-induced inhibition of fibroblast proliferation with wound exudate #78. Notably, in the absence of WE, the PARP inhibitors veliparib, olaparib, talazoparib and rucaparib either had no effect on PDGF-induced induction of proliferation or showed inhibition of the PDGF effect. Therefore, veliparib and talazoparib are surprisingly found to be useful in treating impaired skin wound healing in patients treated with protein growth factors, in particular PDGF.

Figure 15:
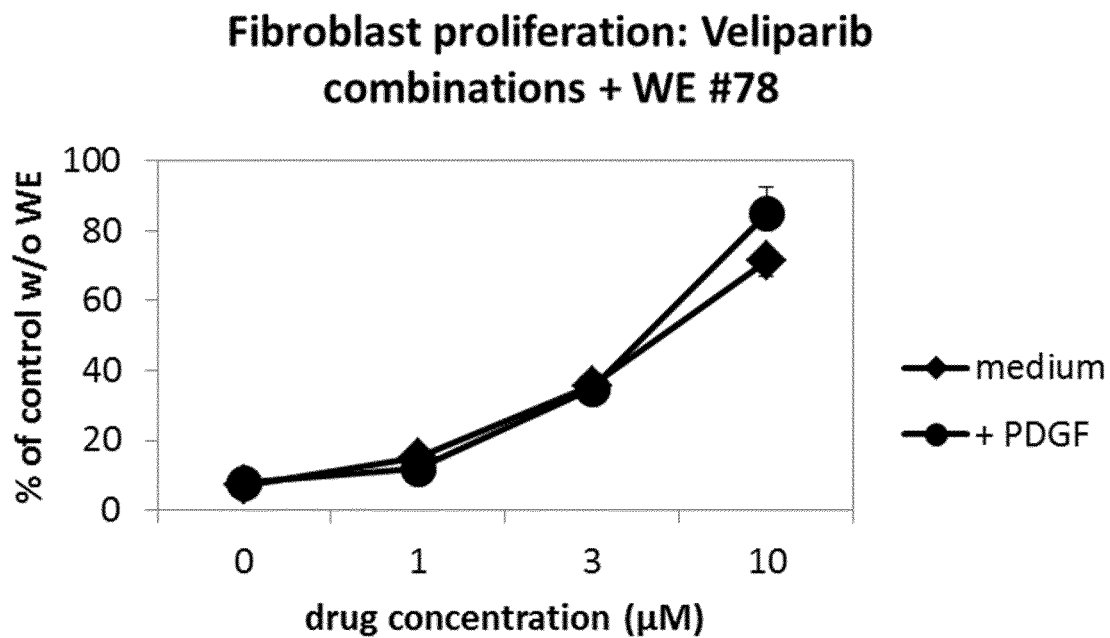
Figure 15:
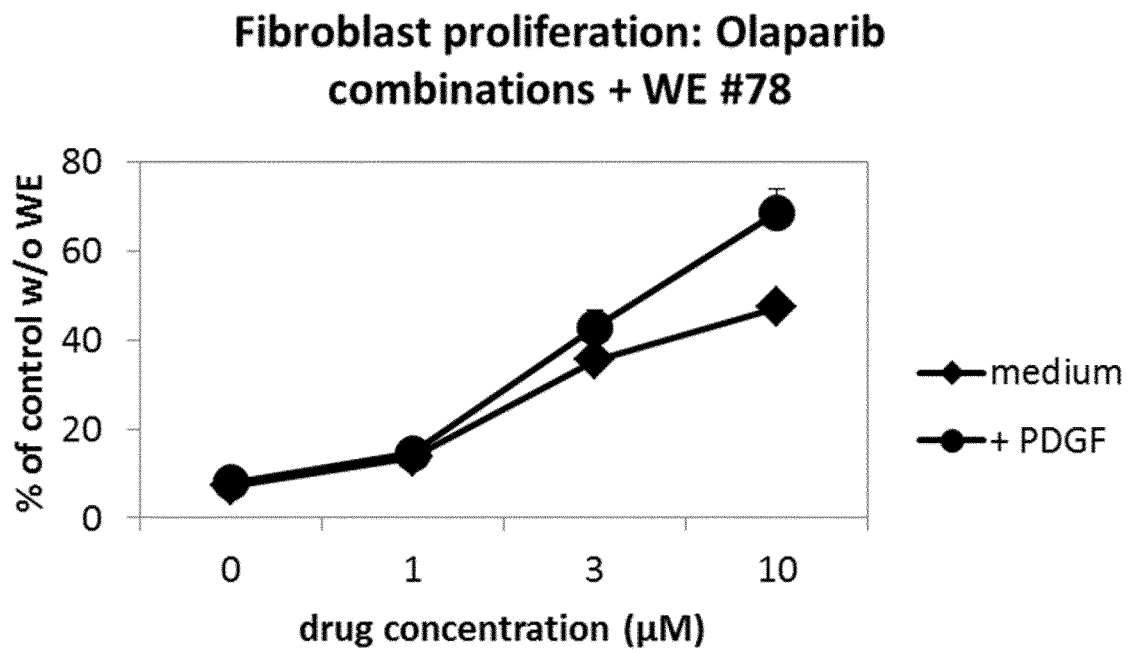
Figure 15:
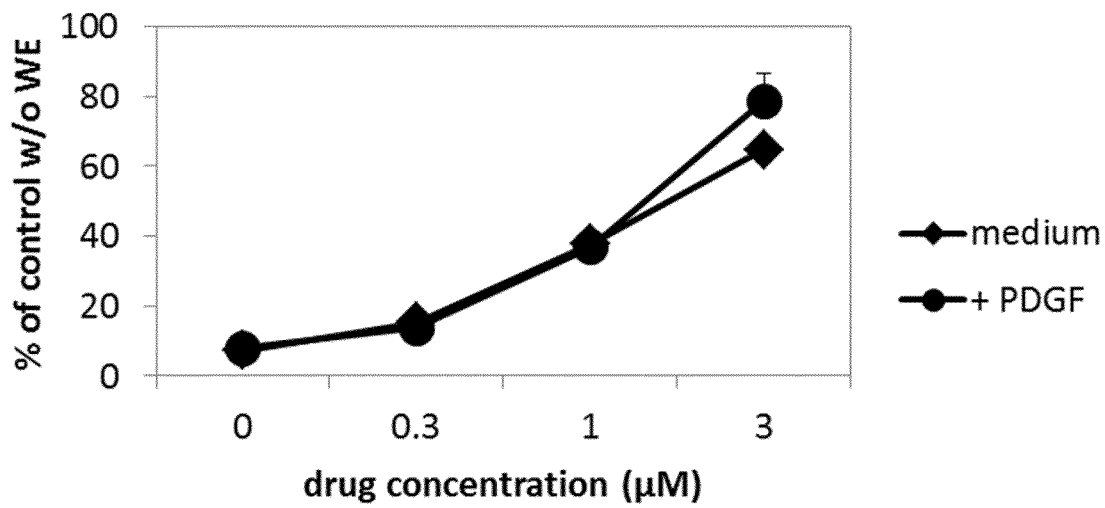
Figure 15:
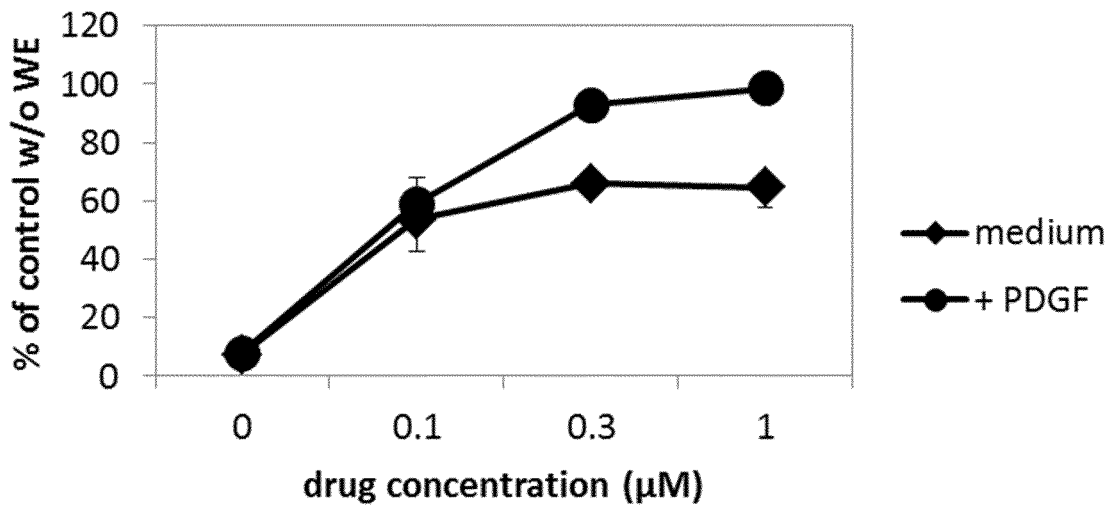

Moreover, FIG. 15 shows that veliparib, olaparib, rucaparib and talazoparib show a dose-dependent increase of HDF proliferation with wound exudate #78, which is even further enhanced by the addition of PDGF, which, on its own, is inactive in the presence of WE #78. Therefore, veliparib, olaparib, rucaparib and talazoparib are surprisingly found to be useful in treating impaired skin wound healing in patients treated with protein growth factors, in particular PDGF.

Figure 16:
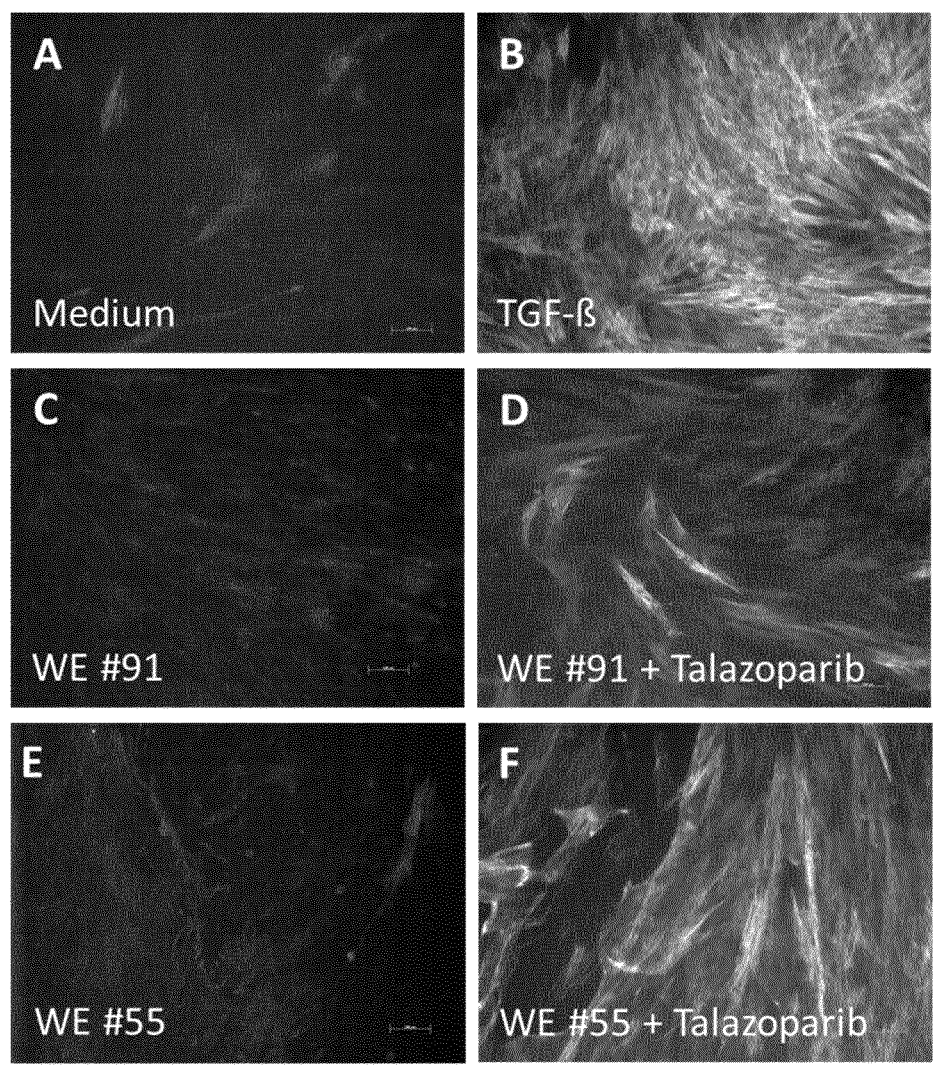

Further, it could be shown in the 2D fibroblast (human dermal fibroblast (HDF) assay that in the absence of wound exudate, TGF-ß increases the staining for the myofibroblast marker alpha-smooth muscle actin (α-SMA). In the presence of wound exudates, talazoparib alone is able to induce expression of α-SMA, an indicator of wound contractility (FIG. 16).

Figure 17:
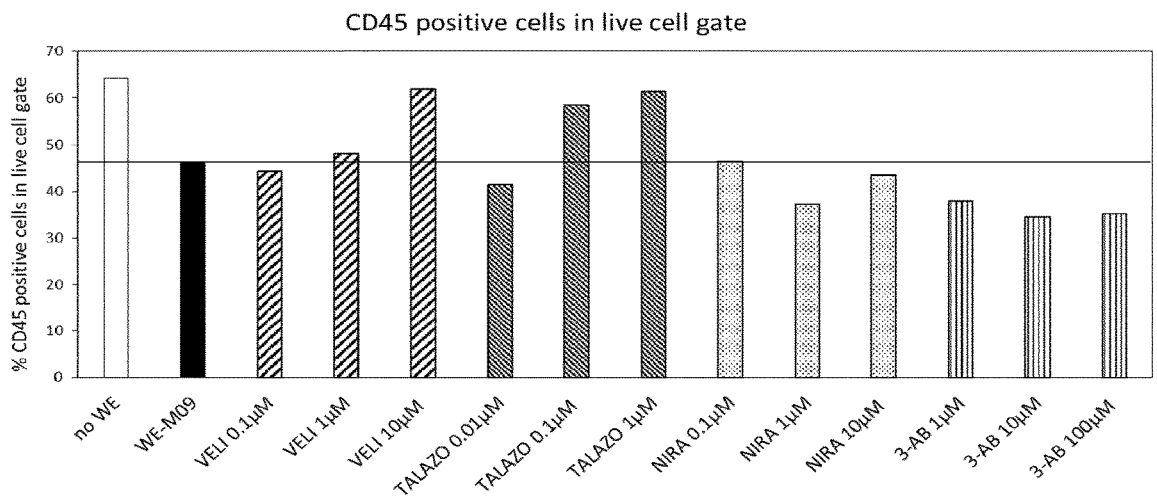
Figure 17:
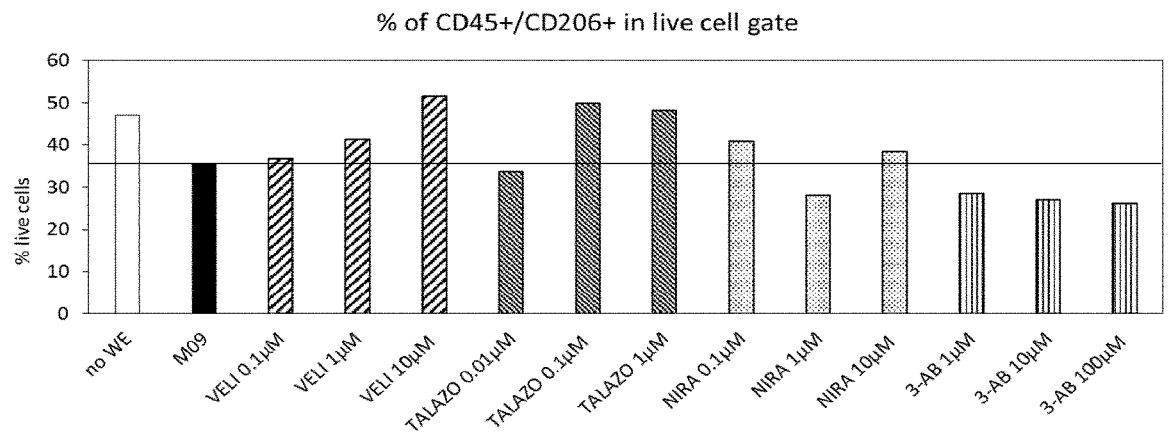
Figure 17:
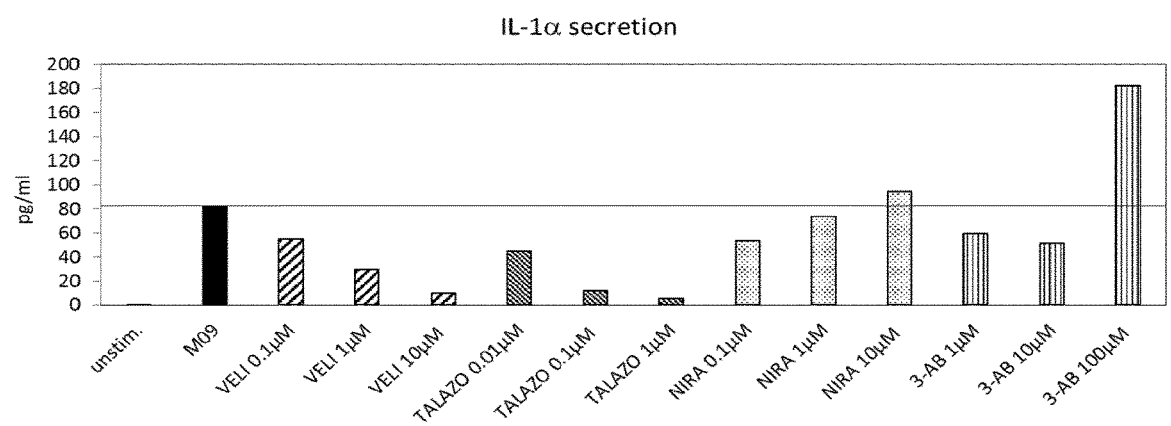

In a fibroblast-macrophage coculture experiment with wound exudate and determining the percentage of live cells in the FACS CD45-gate (corresponding to macrophages), it was shown that the percentage of live cells is reduced upon incubation with wound exudate, and the percentage of live cells is dose-dependently increased by veliparib and talazoparib, but not by niraparib and 3-AB (FIG. 17). The same is true for the macrophage M2 marker CD206. The proinflammatory cytokine IL-1α, induced by wound exudate, is only reduced by veliparib and talazoparib, but not by niraparib or 3-AB.

Figure 18:
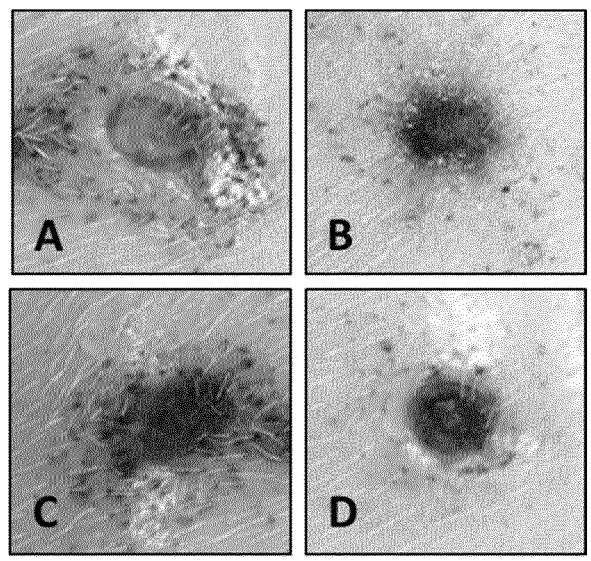
Figure 18:
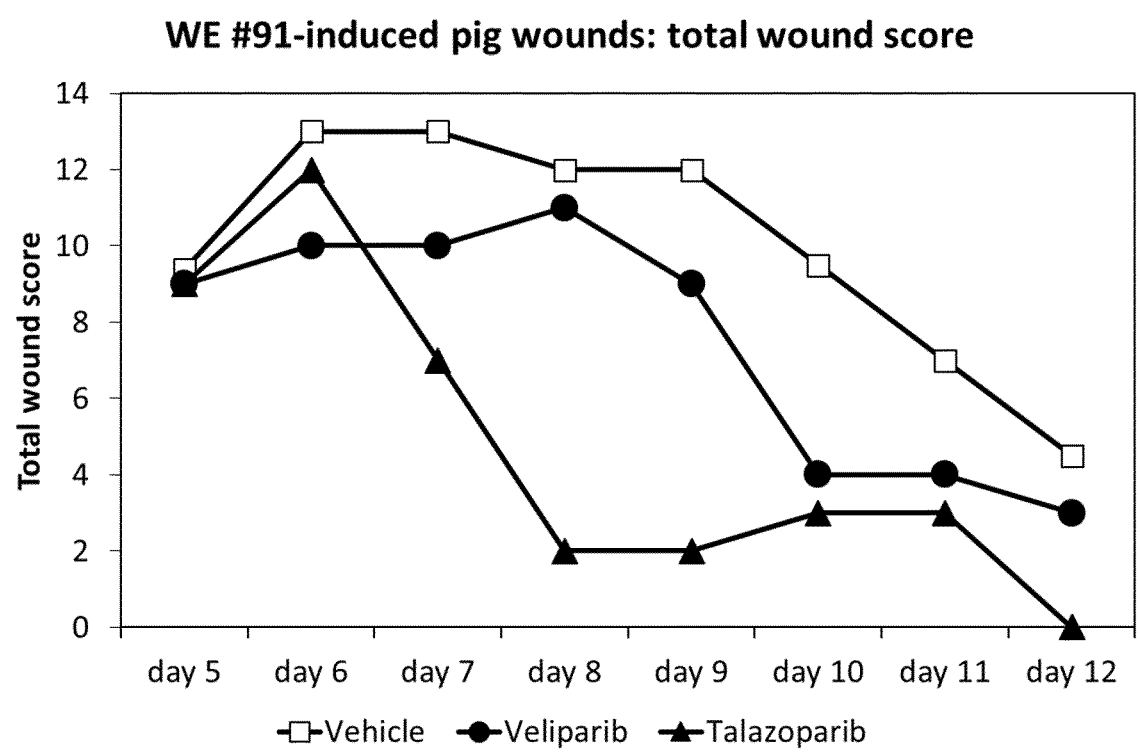

The compounds veliparib and talazoparib for use of the invention were tested in a human-related porcine in vivo animal model for impaired wound healing in humans and other mammals. In wound exudate-induced pig wounds, both veliparib and talazoparib surprisingly improve wound healing (FIG. 18).

In a further in vivo experiment, the time course of delayed pig wound healing induced by another wound exudate, WE #43, was determined. It was found that in particular talazoparib improves wound healing.

Moreover, the effects of different PARP inhibitors on wound exudate-induced inhibition of fibroblast proliferation and induction of IL-1ß secretion was determined. The compounds veliparib, olaparib, AZD-2461, rucaparib, AG-14351 and talazoparib enhanced cell proliferation while at the same time reducing IL-1ß secretion. The inhibitors niraparib, 3-AB and BGP-15 did not show any of these effects.

Thus, the PARP inhibitors Rucaparib, Talazoparib, Veliparib, Olaparib and AZD 2461 are surprisingly suitable for the treatment of chronic wounds, which exhibit impaired skin wound healing. Particularly strong effects were observed in diabetes patients as well as in patients already treated with Vitamin C and/or glucocorticoids, or protein growth factors.

Therefore, in one embodiment, the present invention relates to Rucaparib and/or Talazoparib and/or Veliparib and/or Olaparib, and/or AZD 2461, or a pharmaceutically acceptable salt thereof, for use in the treatment of impaired skin wound healing in a subject.

Rucaparib is a PARP inhibitor targeting PARP-1 which is known in the art and which has the following formula (I):

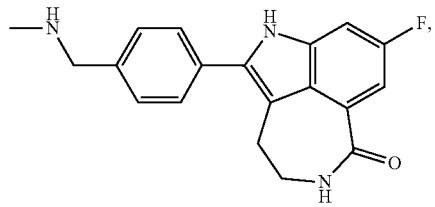

or a pharmaceutically acceptable salt thereof.

Talazoparib is a PARP inhibitor which is known in the art and which has the following formula (III):

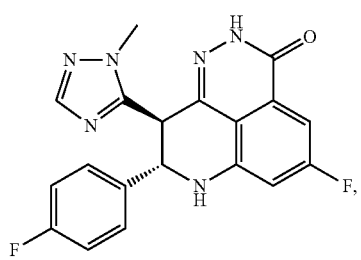

or a pharmaceutically acceptable salt thereof.

Veliparib, also called ABT-888, is a PARP inhibitor which is known in the art and which is 2-((2R)-2-methylpyrrolidin-2-yl)-1H-benzimidazole-4-carboxamide. Veliparib has the following formula (IV):

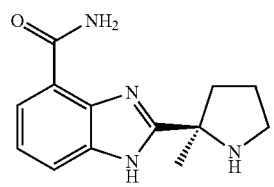

Olaparib, also called AZD-2281, is a PARP inhibitor which is known in the art, and which has the following formula (V):

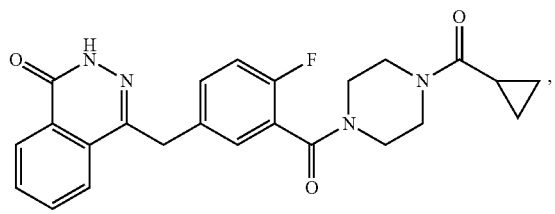

or a pharmaceutically acceptable salt thereof.

AZD-2461 is a PARP inhibitor which is known in the art and which has the following formula (VI):

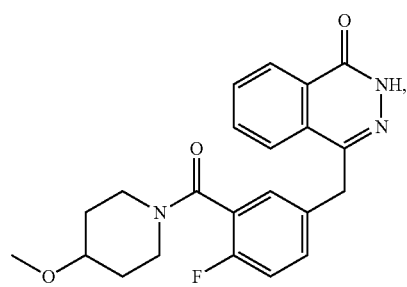

or a pharmaceutically acceptable salt thereof.

The term "pharmaceutically acceptable" is used to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound used in the invention.

Pharmaceutically acceptable acid addition salts can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalenesulfonate, 3-phenylpropionate, picrate, pivalate, thiocyanate, tosylate, and undecanoate.

Pharmaceutically acceptable base addition salts include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl (C1-C6) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Rucaparib, Talazoparib, Veliparib, Olaparib, or AZD 2461 is administered to a subject in a therapeutically effective amount. For systemic applications, the respective PARP inhibitor dose will be in the range of about 10 to 1000 mg/day, depending on the respective PARP inhibitor. Topical formulations of Rucaparib, Talazoparib, Veliparib, Olaparib, or AZD 2461 may be administered in a concentration of about 0,00001 to 10% (w/v), about 0,00001 to 6% (w/v) or about 0,00001 to 1% (w/v), such as 0.0001 to 0.1% (w/v), such as a cream, gel, lotion, ointment, liposomal or nanoparticulate formulation or the like 0.001 to 1% (w/v).

The invention may be used to treat or prevent different types of skin wounds exhibiting impaired skin wound healing. Different types of skin wounds exhibiting impaired skin wound healing which can be treated in accordance with the present invention include a wound of a diabetic patient, a skin wound which is infected by at least one microorganism, an ischemic wound, a wound in a patient suffering from deficient blood supply or venous stasis, an ulcer, such as a diabetic ulcer, venous ulcer, arterial ulcer, such as ulcus cruris arteriosum, mixed ulcer, or pressure ulcer, a neuropathic wound, ulcus cruris, surgical wound, burn, dehiscence, neoplastic ulcer, a bullous skin disease, such as epidermolysis bullosa, and rare ulcer. Microorganisms infecting skin wounds are known in the art and include bacteria and fungi, such as corynebacteria, staphylococci, streptococci, and yeasts such as *candida* species.

In one preferred embodiment of the present invention, the skin wound is selected from a wound of a diabetic patient, a skin wound which is infected by at least one microorganism, an ischemic wound, a wound in a patient suffering from deficient blood supply or venous stasis, an ulcer, such a diabetic ulcer, venous ulcer, arterial ulcer, such as ulcus cruris arteriosum, mixed ulcer, or pressure ulcer, a neuropathic wound, ulcus cruris, surgical wound, burn, dehiscence, neoplastic ulcer, a bullous skin disease, such as epidermolysis bullosa, and rare ulcer.

The subject or individual may be an otherwise healthy individual or may exhibit further diseases and/or co-morbidities, and/or is treated with medication(s) for further diseases and/or co-morbidities. In a preferred embodiment, the subject or individual, in addition to impaired skin wound healing, exhibits further diseases, and/or co-morbidities, and/or is treated with medication(s) for further diseases and/or co-morbidities.

In one preferred embodiment the subject suffers from at least one co-morbidity associated with impaired skin wound healing. Such co-morbidities are for example diabetes, suppressed immune system following transplantation of a graft and graft-versus-host disease (GvHD). Further co-morbidities include adipositas, increased blood pressure, venous stasis or peripheral arterial occlusion. Further co-morbidities are diseases treatable with glucocorticoids.

A co-morbidity is understood as the presence of one or more additional diseases or disorders co-occurring with a given disease.

It was surprisingly found that the treatment of a subject with Rucaparib, Talazoparib, Veliparib, Olaparib, or AZD 2461, wherein the subject receives glucocorticoid treatment and/or ascorbic acid treatment and/or protein growth factor treatment, is in particular effective in those subjects suffering from at least one co-morbidity associated with impaired skin wound healing such as diabetes, suppressed immune system following transplantation of a graft and GvHD.

Therefore, in another preferred embodiment of the present invention, the subject suffers from at least one co-morbidity associated with impaired skin wound healing, in particular diabetes.

The terms "treat", "treating" and "treatment" refer to alleviating or abrogating a disease and/or its attendant symptoms. The term "prevention" or "prevent" refers to treatment that prevents the occurrence of a condition in a subject.

A "wound" is understood as damage to a tissue of a living individual, such as cuts, tears, burns, or breaks, preferably a wound is understood as open injury of a tissue of a living individual.

The present invention relates to Rucaparib and/or Talazoparib and/or Veliparib and/or Olaparib, and/or AZD 2461, or a pharmaceutically acceptable salt thereof, for the prevention and/or treatment of impaired skin wound healing in a subject.

A "skin wound" is understood as a damage to a skin of a living individual, such as cuts, tears, burns, or breaks. Preferably, a skin wound is understood as open injury of the skin of a living individual. The skin may be located at any area of an individual, such as for example the head, the arms, the legs, the chest, or the back. Further, the individual may have one, two, three, four or more skin wounds.

Further, the area of a skin wound may differ. In a preferred embodiment, the skin wound forms wound exudate. In another preferred embodiment, the skin wound forms a wound biofilm.

"Impaired skin wound healing" refers to a skin wound which does not heal at an expected rate. In a preferred embodiment, the impaired skin wound healing is a non-healing skin wound or chronic skin wound. A non-healing skin wound is preferably understood as a skin wound which does not close within 2 months under standard therapy, preferably within 3 or more months under standard therapy. Preferably, a non-healing skin wound is characterized by a lack of wound closure, an increase of the area and/or depth of the wound, necrosis and/or infections of the skin wound, and/or lack of granulation.

As used herein, a "healing skin wound" is understood as a skin wound which heals at an expected rate, in particular, as a skin wound which closes within 2 months under standard therapy. Preferably, a healing skin wound is characterized by ongoing wound closure, granulation, absence of necrosis and/or absence of infections.

In a preferred embodiment of the present invention, the subject has undergone transplantation of a graft, and/or obtains immunosuppressive therapy, and/or is treated with at least one immunosuppressive drug.

Therefore, in another preferred embodiment of the present invention, the subject:
(i) has undergone transplantation of a graft, and/or
(ii) obtains immunosuppressive therapy,
and optionally suffers from diabetes.

In yet another preferred embodiment of the present invention, the subject is treated with at least one immunosuppressive drug, such as a glucocorticoid or a calcineurin inhibitor.

Therefore, in one preferred embodiment, immunosuppressive therapy is by administering a glucocorticoid and/or a calcineurin inhibitor. In another preferred embodiment, the immunosuppressive drug is selected from a glucocorticoid and a calcineurin inhibitor. Suitable calcineurin inhibitors are known in the art and include tacrolimus, pimecrolimus and cyclosporin A. Suitable glucocorticoids are described herein in more detail.

Rucaparib, Talazoparib, Veliparib, Olaparib, or AZD 2461 were shown to be useful in the medical uses of the present invention for the treatment of a plurality of skin wounds exhibiting impaired healing, including, in particular, a wound of a diabetic patient and diabetic ulcers.

Therefore, in yet another preferred embodiment of any of the above aspects of the invention, the skin wound is selected from a wound of a diabetic patient and/or a diabetic ulcer.

An ulcer is understood as a sore on the skin, accompanied by the disintegration of tissue. Ulcers can result in complete loss of the epidermis and often portions of the dermis and even subcutaneous fat.

The "subject" or "individual" is an animal, preferably the individual is a vertebrate, in particular a mammal, more preferably a human.

In another preferred embodiment of the present invention, the subject suffers from diabetes and/or has at least one diabetic ulcer.

The skin wound of the subject may already receive a treatment such as a standard therapy for treating wound healing, or may be untreated regarding the skin wound.

"Standard therapy" is understood as a treatment recommended in general by physicians for skin wounds, in particular one or more selected from wound dressings, surgical and biological (maggot) debridement, infection control, negative pressure therapy, and therapy with a biological or cell treatment.

Therefore, in one preferred embodiment the skin wound of the subject may be untreated or treated with standard therapy for treating wound healing or with one or more of the following for treating wound healing: compression, wound dressings, surgical debridement, biological debridement, infection control, antibiotic therapy, negative pressure therapy, proteins, in particular protein growth factors, antibodies, peptides, sugars, cells or cell constituents, artificial skin, human blood-derived products, gene therapy or genetically engineered wound bed modifications, drugs, herbal medicines, or plant extracts. In one preferred embodiment, the skin wound of the subject may be untreated or treated with standard therapy for treating wound healing wherein the standard therapy does not include treatment with protein growth factors. In another preferred embodiment, the skin wound of the subject may be untreated or treated with standard therapy for treating wound healing wherein the standard therapy includes treatment with protein growth factors.

Moreover, it was surprisingly found that the administration of Rucaparib, Talazoparib, Veliparib, Olaparib, or AZD 2461 is particularly effective in case of a patient who already receives a glucocorticoid therapy, namely a treatment with prednisolone, for treating an underlying co-morbidity. Further, synergistic effects were observed Rucaparib, Talazoparib, Veliparib, Olaparib, or AZD 2461 with glucocorticoids as well as with ascorbic acid and protein growth factors.

In another preferred embodiment, the present invention relates to Rucaparib and/or Talazoparib and/or Veliparib and/or Olaparib, and/or AZD 2461 for use in the prevention and/or treatment of impaired skin wound healing in a subject, wherein, the subject:
(i) is a subject treated with at least one glucocorticoid, and/or
(ii) is a subject to which a pharmaceutical, nutritional supplement or dietary supplement comprising ascorbic acid or a pharmaceutically acceptable salt thereof is administered, and/or
(iii) is a subject treated with at least one protein growth factor.

In one more preferred embodiment, the present invention relates to Rucaparib and/or Talazoparib and/or Veliparib and/or Olaparib, and/or AZD 2461 for use in the prevention and/or treatment of impaired skin wound healing in a subject, wherein the subject is a subject treated with at least one glucocorticoid, and optionally further:
is a subject to which a pharmaceutical, nutritional supplement or dietary supplement comprising ascorbic acid or a pharmaceutically acceptable salt thereof is administered, and/or
is a subject treated with at least one protein growth factor.

In one more preferred embodiment, the present invention relates to Rucaparib and/or Talazoparib and/or Veliparib and/or Olaparib, and/or AZD 2461 for use in the prevention and/or treatment of impaired skin wound healing in a subject, wherein the subject is a subject treated with at least one protein growth factor, and optionally further:
is a subject treated with at least one glucocorticoid, and/or
is a subject to which a pharmaceutical, nutritional supplement or dietary supplement comprising ascorbic acid or a pharmaceutically acceptable salt thereof is administered.

In one more preferred embodiment, the present invention relates to Rucaparib and/or Talazoparib and/or Veliparib and/or Olaparib, and/or AZD 2461 for use in the prevention and/or treatment of impaired skin wound healing in a subject, wherein the subject is a subject treated with at least one protein growth factor, and optionally further:
is a subject treated with at least one glucocorticoid, and/or
is a subject to which a pharmaceutical, nutritional supplement or dietary supplement comprising ascorbic acid or a pharmaceutically acceptable salt thereof is administered.

In one more preferred embodiment, the present invention relates to Rucaparib and/or Talazoparib and/or Veliparib and/or Olaparib, and/or AZD 2461 for use in the prevention and/or treatment of impaired skin wound healing in a subject, wherein the subject is a subject to which a pharmaceutical, nutritional supplement or dietary supplement comprising ascorbic acid or a pharmaceutically acceptable salt thereof is administered, and optionally further:
is a subject treated with at least one glucocorticoid, and/or is a subject treated with at least one protein growth factor.

A subject treated with at least one glucocorticoid is a subject to which a glucocorticoid was administered at least once, preferably several times within at least 1 or 2 weeks or months prior to the administration of the respective PARP inhibitor Rucaparib, Talazoparib, Veliparib, Olaparib, or AZD 2461. In a preferred embodiment, the glucocorticoid is administered to said patient repetitively, such as 1, 2, 3, 4, 5, 6, 7, 8, 9, 10 or more times, in particular over a time period of 1, 2, 3, 4, or 5 weeks or months or more. The glucocorticoid therapy may be a systemic therapy, such as an oral therapy, or a local therapy, such as a topical therapy. The subject is preferably treated with a therapeutically effective dose and regimen for treating the co-morbidity treatable with the respective glucocorticoid. Typically, for systemic applications, the glucocorticoid dose will be in the range of about 0.1 to 1000 mg/day, depending on the glucocorticoid and disease to be treated. Topical formulations of glucocorticoids are typically administered in a concentration of 0.001 to 10% (w/v), 0.001 to 6% (w/v) or 0.001 to 1% (w/v), such as 0.01 to 0.1% (w/v), such as a cream, gel, lotion, ointment or the like.

Co-morbidities that may be treated with a glucocorticoid are known in the art and include immunosuppression in the context of organ transplantation and Graft versus Host Disease (GvHD), allergic disorders, such as asthma, atopic dermatitis, contact dermatitis, drug hypersensitivity reactions, perennial or seasonal allergic rhinitis, and serum sickness, dermatologic diseases, such as bullous dermatitis herpetiformis, dermatitis, atopic dermatitis, eczema, itching, psoriasis, exfoliative erythroderma, mycosis fungoides, pemphigus, and severe erythema multiforme (Stevens-Johnson syndrome), endocrine disorders, such as primary or secondary adrenocortical insufficiency, congenital adrenal hyperplasia, hypercalcemia associated with cancer, and thyroiditis, gastrointestinal diseases, such as regional enteritis and ulcerative colitis, hematologic disorders, such as acquired (autoimmune) hemolytic anemia, congenital (erythroid) hypoplastic anemia (Diamond-Blackfan anemia), idiopathic thrombocytopenic purpura, pure red cell aplasia, and secondary thrombocytopenia; trichinosis with neurologic or myocardial involvement, tuberculous meningitis when used with appropriate antituberculous chemotherapy, for the palliative management of leukemias and lymphomas; diseases of the nervous system, such as acute exacerbations of multiple sclerosis, cerebral edema associated with primary or metastatic brain tumor, craniotomy, or head injury, ophthalmic diseases, such as sympathetic ophthalmia, temporal arteritis, uveitis, and ocular inflammatory conditions; renal diseases, such as idiopathic nephrotic syndrome or lupus erythematosus, respiratory diseases, such as berylliosis, fulminating or disseminated pulmonary tuberculosis, idiopathic eosinophilic pneumonias, symptomatic sarcoidosis; rheumatic disorders, such as acute gouty arthritis, acute rheumatic carditis, ankylosing spondylitis, psoriatic arthritis, rheumatoid arthritis, including juvenile rheumatoid arthritis and for the treatment of dermatomyositis, polymyositis, and systemic lupus erythematosus.

The glucocorticoid treatment is typically administered to patients to treat an underlying co-morbidity, such as an immunosuppressive therapy in the context of transplantation of a graft, or for locally treating a skin disorder such as atopic dermatitis or psoriasis.

In a preferred embodiment of the present invention, the glucocorticoid is selected from the group consisting of cortisol, cortisone acetate, prednisone, prednisolone, methylprednisolone, chloroprednisone, cloprednol, diflupredpredred, fludrocortisone acetate, fluocinolone, fluperolone, fluprednisolone, loteprednol, prednicarbate, tixocortol, triamcinolone, triamcinolone acetonide, dexamethasone, betamethasone, beclometasone, deoxycorticosterone acetate, alclometasone, clobetasol, clobetasone, clocortolone, desoximetasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, ulobetasol, amcinonide, budesonide, ciclesonide, deflazacort, desonide, formocortal, fluclorolone acetonide, fludroxycortide, flunisolide, fluocinolone acetonide, fluocinonide, halcinonide, hydroxymethylprogesterone, and medroxyprogesterone, or a pharmaceutically acceptable salt thereof.

In another preferred embodiment of the present invention, the subject is treated with at least one glucocorticoid by systemic or cutaneous administration.

A subject treated with a pharmaceutical, nutritional supplement or dietary supplement comprising ascorbic acid or a pharmaceutically acceptable salt thereof is a subject to which a pharmaceutical, nutritional supplement or dietary supplement comprising ascorbic acid or a pharmaceutically acceptable salt thereof was administered at least once, preferably several times within at least 1 or 2 weeks prior to the administration of the respective PARP inhibitor Rucaparib, Talazoparib, Veliparib, Olaparib, or AZD 2461. In a preferred embodiment, the pharmaceutical, nutritional supplement or dietary supplement comprising ascorbic acid or a pharmaceutically acceptable salt thereof is administered to said patient repetitively, such as 1, 2, 3, 4, 5, 6, 7, 8, 9, 10 or more times, in particular over a time period of 1, 2, 3, 4, or 5 weeks or months or more. The administration of the pharmaceutical, nutritional supplement or dietary supplement comprising ascorbic acid or a pharmaceutically acceptable salt thereof may be a systemic administration, such as oral administration, or local administration, such as topical administration. For example, a pharmaceutical, nutritional supplement or dietary supplement comprising ascorbic acid or a pharmaceutically acceptable salt thereof for oral administration may contain 50 mg to 1 g per dose, such as tablets, pills or capsules.

A pharmaceutical, nutritional supplement or dietary supplement comprising ascorbic acid or a pharmaceutically acceptable salt thereof may be administered to a patient to treat or prevent a vitamin C deficiency such as scurvy, or to maintain general well-being.

A subject treated with at least one protein growth factor is a subject to which a protein growth factor was administered at least once, preferably several times within at least 1 or 2 weeks or months prior to the administration of the respective PARP inhibitor Rucaparib, Talazoparib, Veliparib, Olaparib, or AZD 2461. In a preferred embodiment, the protein growth factor is administered to said patient repetitively, such as 1, 2, 3, 4, 5, 6, 7, 8, 9, 10 or more times, in particular over a time period of 1, 2, 3, 4, or 5 weeks or months or more. The protein growth factor therapy may be a systemic therapy, such as an oral therapy, or a local therapy, such as a topical therapy, preferably the therapy is a topical therapy. The subject is preferably treated with a therapeutically effective dose and regimen for treating or preventing impaired wound healing, or for treating an underlying co-morbidity, such as lung fibrosis in the case of TGF-β. Typically, for topical applications, the topical formulations of protein growth factors are typically administered in a concentration of 0.0001 to 10% (w/v), 0.0001 to 6% (w/v) or 0.0001 to 1% (w/v), such as 0.001 to 0.1% (w/v), such as a cream, gel, lotion, ointment or the like. In particular, a gel containing 0.01% PDGF-BB (becaplermin) may be used, which is marketed as Regranex®. The protein growth factor is in a preferred embodiment a human protein growth factor and/or is selected from a platelet derived growth factor (PDGF), transforming growth factor beta (TGF-ß), basic fibroblast growth factor (bFGF), keratinocyte growth factor (KGF), epidermal growth factor (EGF), Insulin-like growth factor 1 (IGF-1), vascular endothelial growth factor (VEGF) and (hepatocyte growth factor) HGF. In an even more preferred embodiment, the protein growth factor is selected from a platelet derived growth factor (PDGF), transforming growth factor beta (TGF-ß), and basic fibroblast growth factor (bFGF), most preferably the protein growth factor is PDGF, in particular becaplermin.

The experimental data summarized above show a beneficial effect for the PARP inhibitors Rucaparib, Talazoparib, Veliparib, Olaparib, or AZD 2461 in the context of a wound exudate from a patient who already receives a glucocorticoid therapy, e.g. as immunosuppressive therapy in the context of a prior organ transplantation. Accordingly, Rucaparib, Talazoparib, Veliparib, Olaparib, and AZD 2461 were surprisingly found to be suitable to treat or prevent impaired skin wound healing in subjects, that already receive a glucocorticoid therapy or to which Vitamin C is already administered as a pharmaceutical, nutritional supplement or dietary supplement, or that already receive a protein growth factor therapy.

The treatment with at least one glucocorticoid of a patient already receiving a glucocorticoid therapy may occur by various routes of administration, depending on the co-morbidity treated by the glucocorticoid, and may in particular be systemic or cutaneous administration. For example, the co-morbidity may be a skin disease such as eczema, dermatitis, atopic dermatitis or psoriasis. In this case, the subject may be treated by topical, in particular cutaneous, administration, e.g. with a glucocorticoid-containing cream, lotion, gel or the like, or by systemic administration, in particular oral administration, such as a glucocorticoid-containing tablet or pill. For example, the co-morbidity may be transplantation of a graft and/or GvHD. In this case, the subject may be treated by systemic administration, in particular oral administration, such as a glucocorticoid-containing tablet or pill.

Therefore, in yet another preferred embodiment of any of the above aspects of the invention, the subject is treated with at least one glucocorticoid by systemic or cutaneous administration.

Further, the administration of Rucaparib, Talazoparib, Veliparib, Olaparib, or AZD 2461 is particularly effective in case of a patient who already receives a protein growth factor therapy, in particular selected from a platelet derived growth factor (PDGF), transforming growth factor beta (TGF-ß), basic fibroblast growth factor (bFGF), keratinocyte growth factor (KGF), epidermal growth factor (EGF), Insulin-like growth factor 1 (IGF-1), vascular endothelial growth factor (VEGF) and hepatocyte growth factor (HGF) therapy, for treating an underlying co-morbidity or from treating or preventing impaired wound healing.

The treatment with at least one protein growth factor of a patient already receiving a protein growth factor therapy may occur by various routes of administration, depending on the co-morbidity treated by the protein growth factor, and may in particular be systemic or cutaneous administration. In a further embodiment, the route of administration may be systemic, local or cutaneous administration. In case of preventing or treating a skin disease such as wound healing, the protein growth factor is preferably administered topically or cutaneously, or locally, such as perilesionally and/or intralesionally, topically or cutaneously. In this case, the subject may be treated by topical, in particular cutaneous, administration, e.g. with a protein growth factor-containing cream, lotion, gel or the like or via local, such as perilesional and/or intralesional administration. For example, the patient already receives becaplermin (PDGF-BB) for treating or preventing impaired wound healing. In this case, the subject may be treated by topical administration, e.g. with a PDGF-BB-containing gel (Regranex®). In another example, the co-morbidity may be lung fibrosis, such as for a patient treated with TGF-β. In another example, the co-morbidity may be cancer or side-effects from cancer chemotherapy, such as oral mucositis, such as for a patient treated with human KGF (palifermin; recombinant KGF). In these cases, the subject may be treated by systemic administration, in particular oral administration, such as a protein growth factor-containing tablet or pill or by injection, such as intravenous injection. For example, palifermin may be administered by bolus injection of a buffered solution of palifermin, e.g. at a dose of 50 to 300 µg/kg bw, such as 180 µg/kg bw. For example, the patient already receives rhEGF (Heberprot-P®) for treating ulcerations in the diabetic foot ulcus syndrome. In this case, the subject may be treated by perilesional and/or intralesional administration, e.g. with rhEGF (Heberprot-P®). For example, the patient already receives human basic fibroblast growth factor (rhbFGF) (Trafermin; Fiblast®)) for treating skin ulcers. In this case, the subject may be treated by topical administration, e.g. with a topical spray containing human basic fibroblast growth factor (rhbFGF) (Trafermin; Fiblast®)).

Therefore, in yet another preferred embodiment of any of the above aspects of the invention, the subject is treated with at least one protein growth factor by systemic or topical administration, or systemic, local or topical administration, more preferably by topical, in particular cutaneous administration. In a further preferred embodiment, the subject is treated with at least one protein growth factor by local administration, such as perilesional and/or intralesional administration.

In a more preferred embodiment of the present invention, the protein growth factor is a human protein growth factor.

In another preferred embodiment of the present invention, the protein growth factor is selected from a platelet derived growth factor (PDGF), transforming growth factor beta (TGF-ß), basic fibroblast growth factor (bFGF), keratinocyte growth factor (KGF), epidermal growth factor (EGF), Insulin-like growth factor 1 (IGF-1), vascular endothelial growth factor (VEGF) and hepatocyte growth factor (HGF).

Further, it was surprisingly found that the assays based on fibroblast proliferation as described in Example 1.1 and fibroblast-derived matrix formation as described in Example 1.2 surprisingly allow for the identification of subjects suffering from impaired skin wound healing which are responsive to a treatment and/or prevention with Rucaparib, Talazoparib, Veliparib, Olaparib, or AZD 2461.

The assays may be used for successful stratification and identification of subjects suffering from impaired skin wound healing.

In another preferred embodiment of the present invention, the subject is identified to be responsive to the treatment of impaired skin wound healing by performing steps i) and/or ii):

i) measuring the proliferation of primary fibroblast cells in the presence of:
   (1) a wound exudate sample or wound biofilm sample obtained from the skin wound of said subject, and
   (2) the following compounds:
      (i) Rucaparib or a pharmaceutically acceptable salt thereof; and/or
      (ii) Talazoparib or a pharmaceutically acceptable salt thereof; and/or
      (iii) Veliparib or a pharmaceutically acceptable salt thereof; and/or
      (iv) Olaparib or a pharmaceutically acceptable salt thereof; and/or
      (v) AZD 2461 or a pharmaceutically acceptable salt thereof;

ii) measuring the fibroblast-derived matrix formation by primary fibroblast cells in the presence of:
   (1) a wound exudate sample or wound biofilm sample obtained from the skin wound of said subject, and
   (2) the following compounds:
      (i) Rucaparib or a pharmaceutically acceptable salt thereof; and/or
      (ii) Talazoparib or a pharmaceutically acceptable salt thereof; and/or
      (iii) Veliparib or a pharmaceutically acceptable salt thereof; and/or
      (iv) Olaparib or a pharmaceutically acceptable salt thereof; and/or
      (v) AZD 2461 or a pharmaceutically acceptable salt thereof.

In one preferred embodiment of the present invention, the sample is a wound exudate sample. In another preferred embodiment, the sample is a wound biofilm sample. In a more preferred embodiment, the sample is a wound exudate sample.

In a further preferred embodiment of the present invention, the subject is identified to be responsive to the treatment of impaired skin wound healing with Rucaparib and/or Talazoparib and/or Veliparib and/or Olaparib, and/or AZD 2461, or a pharmaceutically acceptable salt thereof, in case the value of proliferation of primary fibroblast cells measured in step i) and/or the value of the fibroblast-derived matrix formation by primary fibroblast cells measured in step ii) is at least 20% above a control value established in the absence of the compounds of (2).

The PARP inhibitor(s) Rucaparib, Talazoparib, Veliparib, Olaparib, and/or AZD 2461 to be administered to the subject in case the subject is identified to be responsive may be the same PARP inhibitor(s) or different PARP inhibitor(s) or a subgroup of the PARP inhibitor(s), preferably the same PARP inhibitor(s).

Measuring the proliferation of primary fibroblast cells in the presence of a wound exudate sample, or wound biofilm sample, obtained from said skin wound and the compounds of (2) may be performed as shown in the examples, in particular in Example 1.1. The assay is also referred to as "HDF proliferation", "human dermal fibroblast proliferation", "fibroblast proliferation" or "2D fibroblast proliferation" assay in the present application. For the assay, primary fibroblast cells are used, which may be primary mammal dermal fibroblasts, preferably primary human dermal fibroblasts. Methods for culturing primary human dermal fibroblast cells are known in the art and are for example described in the examples. For example, the cells may be cultured using DMEM medium containing FCS. In a further preferred embodiment, the cells are incubated on a solid support, thereby allowing the cells to adhere to the support, as for example described in the Examples, where multiwell plates were used. Further, the cells are contacted with the wound exudate sample, or wound biofilm sample, which is optionally diluted, e.g. diluted with medium or a saline aqueous liquid, and the compounds of (2). The contacting may be performed before or after adherence of the cells occurs. For example, the contacting may be achieved by adding the optionally diluted, liquid wound exudate sample, or wound biofilm sample, and the compounds of (2) to the cells either prior to adherence, for example at the seeding of the cells, or after adherence. The contacting may be achieved e.g. by pipetting, and optionally gentle mixing. The cells are incubated for an appropriate time, such as for 6 hours to 300 hours, more preferably 12 hours to 200 hours, even more preferably 24 hours to 120 hours. In the examples, 72 hours were successfully used. For negative control samples, a corresponding liquid in the absence of the compounds of (2) may be added in addition to wound exudate, or wound biofilm, or only wound exudate, or wound biofilm, is added. Subsequently, the amount, preferably the cell number, including the formation of extracellular matrix, of the primary fibroblast cells is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the primary fibroblast cells. The stained cells including the extracellular matrix formed may then be quantified e.g. by determining absorbance or fluorescence at a suitable wavelength, depending on the dye. Preferably, the steps are performed in 2D cell culture, which allows for culturing the cells adherently on a solid support. Preferably, the sample is a wound exudate sample.

Preferably, the method step includes the following steps:
(i) culturing primary human dermal fibroblast cells,
(ii) incubating the cells on a solid support, thereby allowing the cells to adhere to the support,
(iii) contacting the cells with (1) the wound exudate sample, or wound biofilm sample, which is optionally diluted, and the compounds of (2), wherein the contacting may be performed before or after adherence of the cells occurs, and wherein the contacting of (1) and (2) may be performed simultaneously or sequentially, and
(iv) determining the amount, preferably the cell number, including the formation of extracellular matrix, of the primary fibroblast cells, such as by fixing cells and determining total protein content,
preferably wherein the method is performed in 2D cell culture.

In one preferred embodiment of the present invention, the sample is a wound exudate sample. In another preferred embodiment, the sample is a wound biofilm sample. In a more preferred embodiment, the sample is a wound exudate sample.

The culturing of cells is preferably performed at about 20° C. to 40° C., more preferably 25° C. to 38° C., even more preferably at about 37° C.

Measuring the fibroblast-derived matrix formation by primary fibroblast cells in the presence of a wound exudate sample, or wound biofilm sample, obtained from a skin wound may be performed as shown in the examples, in particular in Example 1.2. The assay is also referred to as "ECM formation", "fibroblast-derived matrix", or "3D fibroblast derived matrix" assay in the present application. For the assay, primary fibroblast cells are used, which may be primary mammal dermal fibroblasts, preferably primary human dermal fibroblasts. In the examples, primary human dermal fibroblast cells are seeded on a support, which is preferably pre-coated with an adhesion enhancing agent, such as gelatin. For example, the coating may be achieved by incubating the support with a solution or suspension containing the adhesion enhancing agent, such as gelatin. In the examples, a 0.2% gelatin solution was successfully used. Preferably, the cells are cultured until confluence is reached. Subsequently, the cells are contacted with (i) a matrix promoting supplement, (ii) the wound exudate sample, or wound biofilm sample, which is optionally diluted, and (iii) the compounds of (2), wherein (i), (ii) and (ii) may be contacted simultaneously or sequentially. For example, the matrix promoting supplement, which is preferably selected from a solution comprising Vitamin C or a physiologically acceptable salt thereof, such as the sodium salt, or 2-phospho-L-ascorbic acid or a physiologically acceptable salt thereof, and a combination of EGF and insulin, is added to the cells, e.g. by pipetting, and optionally gentle mixing. The wound exudate sample, or wound biofilm sample, which is optionally diluted, may be contacted simultaneously or sequentially and the compounds of (2) are added simultaneously or sequentially. For example, the optionally diluted wound exudate sample, or wound biofilm sample, may be mixed with the matrix promoting supplement, and the mixture may be added to the cells, and the compounds of (2) are added subsequently. Alternatively, the optionally diluted wound exudate sample, or wound biofilm sample, may be added separately, but simultaneously, or separately, but subsequent to or prior to the matrix promoting supplement and/or the compounds of (2). In case of subsequent non-simultaneous contacting, the components (i), (ii) and (iii) are preferably contacted within 1 hour. The cells are subsequently incubated, preferably for 12 hours to 20 days, wherein the medium is optionally replaced at least one time with fresh medium supplemented with optionally diluted wound exudate, or wound biofilm, and matrix promoting supplement. In the example, the medium was replaced once after 4 days of incubation, and the total incubation was 8 days. As a 3-dimensional fibroblast-derived matrix is formed, the solid support preferably contains at least one cavity which allows for filling of the space and therefore allows for a 3D cell culture. Subsequently, the amount of the fibroblast-derived matrix is determined, such as by fixing cells and determining total protein content. The cells may for example be fixed using paraformaldehyde. Further, a suitable dye, such as sulforhodamine B may be used for determining the amount, preferably the cell number, including the formation of extracellular matrix, of the primary fibroblast cells. The stained cells including the formation of extracellular matrix may then be quantified e.g. by determining absorbance or fluorescence at a suitable wavelength, depending on the dye. For negative control samples, a corresponding liquid in the absence of the compounds of (2) may be added in addition to wound exudate, or wound biofilm, or only wound exudate, or wound biofilm, is added. Preferably, the sample is a wound exudate sample.

Accordingly, the method step preferably includes the following steps:
(i) seeding primary human dermal fibroblast cells on a support, which is preferably pre-coated with an adhesion enhancing agent, such as gelatin,
(ii) culturing the cells on the support, preferably until confluence is reached,
(iii) contacting the cells with (i) a matrix promoting supplement, (ii) the wound exudate sample, or wound biofilm sample, which is optionally diluted, and (iii) the compounds of (2), wherein (i) and (ii) may be contacted simultaneously or sequentially,
(iv) determining the amount of the fibroblast-derived matrix, such as by fixing cells and determining total protein content,
preferably wherein the method is performed in 3D cell culture.

In one preferred embodiment of the present invention, the sample is a wound exudate sample. In another preferred embodiment, the sample is a wound biofilm sample. In a more preferred embodiment, the sample is a wound exudate sample.

The "fibroblast-derived matrix" or "FDM" is understood as the extracellular matrix (ECM) formed by living fibroblast cells in an environment conducive for matrix formation, e.g. in the presence of a matrix promoting supplement. FDM is obtainable as described in the examples. In particular, FDM is obtainable by (i) seeding primary human dermal fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin.

A "matrix promoting supplement" is understood as a compound or composition which promotes the formation of fibroblast-derived matrix by living fibroblast cells in an in vitro cell culture. Suitable matrix promoting supplements are Vitamin C or a physiologically acceptable salt thereof, such the sodium salt, or 2-phospho-L-ascorbic acid or a physiologically acceptable salt thereof, and a combination of EGF and insulin, as well as compositions comprising the compounds, such as solutions or suspensions. A combination of EGF and insulin may be provided to the cell culture separately, e.g. as separate solutions comprising EGF or insulin respectively, or together, e.g. as solution comprising EGF and insulin.

An "adhesion enhancing agent" is an agent which enhances adhesion of cells to a solid support, such as a plastic support, but which does not substantially interfere with the viability of the cells. In a preferred embodiment, the adhesion enhancing agent is gelatin or fibronectin, more preferably gelatin.

"2D cell culture" is understood as a cell culture wherein the cells are cultured in a planar or substantially planar surface. In a preferred embodiment, the 2D cell culture is culturing of adherent cells.

"3D cell culture" is understood as a cell culture wherein the cells are cultured on a non-planar or substantially non-planar surface. In a preferred embodiment, the 3D cell culture is culturing of adherent cells and/or culturing of cells within a matrix, such as ECM, in particular FDM.

A "support" or "solid support" is preferably selected from a chip, array, such as a microarray or nanoarray, a plate, such as a multiwell plate, or a dish. For cell culture applications, the solid support is preferably suitable for culturing cells, for example the support may be a plastic support.

"Wound exudate" is understood as the extracellular fluid located within and above a skin wound. The wound exudate is also referred to a "liquid biopsy".

"Wound biofilm" is understood as substance, resulting from an infection of a skin wound by micro-organisms that are capable of forming colonies. Typically, the wound biofilm is a gummy or gum-like substance. A wound biofilm comprises microbial species selected from bacteria, fungi, yeasts, algae and other micro-organisms, and cellular debris. A wound biofilm is formed when certain types of micro-organisms attach themselves to the surface of skin wounds by secreting a gummy or gum-like substance. For example, a wound biofilm sample may be obtained by surgical sharp debridement of the wound surface or by wiping of the wound surface with a swab, such as a cotton swab or nylon-flocked swab, or wound dressing material.

A "wound exudate sample" or "WE" is understood as a sample of wound exudate obtained from a skin wound of an individual. Methods for obtaining a wound exudate sample are known in the art. For example, a wound exudate sample may be obtained by a physical or chemical method, in particular by applying negative pressure to the skin wound, such as by using a negative pressure drainage device, a method using capillary forces, collecting wound exudate in a film dressing or membrane, collecting wound exudate in a syringe, applying an absorptive material, such as absorptive beads, or a filter, or by using a swab, such as a cotton swab or nylon-flocked swab, in particular wherein the film dressing or membrane is a cellulose layer and/or wherein the absorptive material is a cellulose layer. Preferred suitable cellulose layers are nanocellulose layers. The volume of wound exudate sample may vary and may be in the range of 1 nl to 1 l, 10 nl to 10 1 l, or 100 nl to 1 l, such as 1 µl to 1 l, 1 ml to 1 l or 10 ml to 1 l. For example, wound exudate samples investigated in the examples had a volume of up to 400 ml and typically had a volume of 0.1 to 100 ml, in particular 1 to 50 ml. The wound exudate sample may be used the methods of the invention directly after obtaining the sample or may be stored, in particular stored at <4° C., <0° C. or <10° C., such as about −20° C., before usage in the methods of the invention.

The nanocellulose layer which can be used according to the invention may be a nanocellulose membrane or dressing, which is optionally covered, and which may have e.g. a disc-like form. Accordingly, the cellulose layer or nanocellulose layer is in one preferred embodiment a cellulose disc or nanocellulose disc. Typically, the nanocellulose surface area brought into contact with wound exudate is in the range of about 1 cm² to about 100 cm².

A "wound biofilm sample" or "WB" is understood as a sample of wound biofilm obtained from a skin wound of an individual. Methods for obtaining a wound biofilm sample are known in the art. For example, a wound biofilm sample may be obtained by surgical sharp debridement or by wiping of the wound surface with a swab, such as a cotton swab or nylon-flocked swab, or wound dressing material. The volume of wound biofilm sample may vary and may be in the range of 1 nl to 1 l, 10 nl to 1 l, or 100 nl to 1 l, such as 1 µl to 1 l, 1 ml to 1 l or 10 ml to 1 l. The wet weight of wound biofilm may vary and may be in the range of 10 µg to 10 g, 100 µg to 10 g, such as 1 mg to 10 g, 10 mg to 10 g, 100 mg to 10 g, or 1 g to 10 g. The wound biofilm sample may be used the methods of the invention directly after obtaining the sample or may be stored, in particular stored at <4° C., <0° C. or <10° C. before usage in the methods of the invention. The wound biofilm sample can be extracted with a suitable liquid, such as cell culture medium or buffer, in particular with liquid of 5 to 10 times of the weight of the sample.

It was surprisingly found that the above assays relating to measuring the proliferation of primary fibroblast cells and the fibroblast-derived matrix formation by primary fibroblast cells can reliably identify subjects responsive to a treatment and/or prevention of impaired skin wound healing of any of the above embodiments of the invention.

Moreover, it was found that the accuracy of the identification of responsive subjects is improved in case both measuring the proliferation of primary fibroblast cells and the fibroblast-derived matrix formation by primary fibroblast cells is performed. Accordingly, in a more preferred embodiment, the subject is identified to be responsive to the treatment of impaired skin wound healing in case the value of proliferation of primary fibroblast cells measured in step i) and the value of the fibroblast-derived matrix formation by primary fibroblast cells measured in step ii) is at least 20% above a control value established in the absence of the compounds of (2).

Further, the accuracy of the identification of responsive subjects is improved in case the measured values are clearly increased vis-à-vis the respective control value established in the absence of the compounds of (2).

Accordingly, in a yet further preferred embodiment, the subject is identified to be responsive to the treatment of impaired skin wound healing in case the value of proliferation of primary fibroblast cells measured in step i) and/or the value of the fibroblast-derived matrix formation by primary fibroblast cells measured in step ii) is at least 30%, 40%, 50%, 60%, 70%, 80%, 100% or more above a control value established in the absence of the compounds of (2).

The control value(s) may be determined in parallel or may be established independently, preferably in parallel.

In another embodiment, the present invention relates to an in vitro method for identifying a subject suffering from impaired skin wound healing to be responsive to the treatment with Rucaparib and/or Talazoparib and/or Veliparib and/or Olaparib and/or AZD 2461, or a pharmaceutically acceptable salt thereof, comprising performing steps i) and/or ii):

i) measuring the proliferation of primary fibroblast cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;

ii) measuring the fibroblast-derived matrix formation by primary fibroblast cells in the presence of:
  (1) a wound exudate sample, or wound biofilm sample, obtained from the skin wound of said subject, and
  (2) the following compounds:
    (v) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof, and/or
    (iv) Olaparib or a pharmaceutically acceptable salt thereof; and/or
    (v) AZD 2461 or a pharmaceutically acceptable salt thereof;

wherein the subject is identified to be responsive to the treatment with Rucaparib and/or Talazoparib and/or Veliparib and/or Olaparib and/or AZD 2461, or a pharmaceutically acceptable salt thereof, in case the value of proliferation of primary fibroblast cells measured in step i) and/or the value of the fibroblast-derived matrix formation by primary fibroblast cells measured in step ii) is at least 20% above a control value established in the absence of the compounds of (2).

In one preferred embodiment of the present invention, the sample is a wound exudate sample. In another preferred embodiment, the sample is a wound biofilm sample. In a more preferred embodiment, the sample is a wound exudate sample.

It is understood that the preferred embodiments described in the context of other embodiments of the present invention also apply to this embodiment of the invention. In particular, the preferred embodiments described above for the fibroblast proliferation assay and fibroblast-derived matrix formation assay are understood to also apply to these aspects and embodiments of the present invention.

In particular, the PARP inhibitor(s) Rucaparib, Talazoparib, Veliparib, Olaparib, and/or AZD 2461 which may be administered to the subject subsequent to the method of the invention, in case the subject is identified to be responsive, may be the same PARP inhibitor(s) or different PARP inhibitor(s) or a subgroup of the PARP inhibitor(s), preferably the same PARP inhibitor(s).

The accuracy and reliability of the in vitro methods of the present invention as well as the uses of the present invention wherein responsiveness is determined based on the cellular assays described above can be further increased by including a further assay in the method, which measures the proliferation of keratinocyte cells, such as primary keratinocyte cells or HaCaT cells. The use of HaCaT cells is to be more preferred as compared to primary keratinocytes and allows for reliable prediction, in combination with the fibroblast-based assays described above.

Therefore, in another preferred embodiment of an embodiment of any of the above aspects of the invention, the subject is identified to be responsive to the treatment of impaired skin wound healing with Rucaparib and/or Talazoparib and/or Veliparib and/or Olaparib and/or AZD 2461, or a pharmaceutically acceptable salt thereof, as described above, by performing steps i) and/or ii) and/or iiia):

i) measuring the proliferation of primary fibroblast cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;

ii) measuring the fibroblast-derived matrix formation by primary fibroblast cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;

iiia) measuring the proliferation of keratinocyte cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof.

In a more preferred embodiment, the subject is identified to be responsive to the treatment of impaired skin wound healing with Rucaparib and/or Talazoparib and/or Veliparib and/or Olaparib and/or AZD 2461, or a pharmaceutically acceptable salt thereof, as described above, in case the value of proliferation of primary fibroblast cells measured in step i) and/or the value of the fibroblast-derived matrix formation by primary fibroblast cells measured in step ii) and/or the value of the proliferation of keratinocyte cells in step iiia) is at least 20% above a control value established in the absence of the compounds of (2).

In one preferred embodiment of the present invention, the sample is a wound exudate sample. In another preferred embodiment, the sample is a wound biofilm sample. In a more preferred embodiment, the sample is a wound exudate sample.

Therefore, in a further aspect, the present invention relates to an in vitro method of identifying a subject suffering from impaired skin wound healing to be responsive to the treatment Rucaparib and/or Talazoparib and/or Veliparib and/or Olaparib and/or AZD 2461, or a pharmaceutically acceptable salt thereof,
comprising performing steps i) and/or ii) and/or iiia):
i) measuring the proliferation of primary fibroblast cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;

ii) measuring the fibroblast-derived matrix formation by primary fibroblast cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;
iiia) measuring the proliferation of keratinocyte cells in the presence of:
  (1) a wound exudate sample, or wound biofilm sample, obtained from the skin wound of said subject, and
  (2) the following compounds:
    (i) Rucaparib or a pharmaceutically acceptable salt thereof; and/or
    (ii) Talazoparib or a pharmaceutically acceptable salt thereof; and/or
    (iii) Veliparib or a pharmaceutically acceptable salt thereof; and/or
    (iv) Olaparib or a pharmaceutically acceptable salt thereof; and/or
    (v) AZD 2461 or a pharmaceutically acceptable salt thereof;
wherein the subject is identified to be responsive to the treatment of impaired skin wound healing in case the value of proliferation of primary fibroblast cells measured in step i) and/or the value of the fibroblast-derived matrix formation by primary fibroblast cells measured in step ii) and/or the value of the proliferation of keratinocyte cells in step iiia) is at least 20% above a control value established in the absence of the compounds of (2).

In one preferred embodiment of the present invention, the sample is a wound exudate sample. In another preferred embodiment, the sample is a wound biofilm sample. In a more preferred embodiment, the sample is a wound exudate sample.

In step iiia), the proliferation of keratinocyte cells is measured in the presence of a wound exudate sample, or wound biofilm sample, obtained from said skin wound and the compound(s) of (2). The keratinocyte proliferation assay preferably includes culturing human primary keratinocyte cells, or HaCaT cells, which is a standard keratinocyte cell line, under standard conditions, such as by using DMEM containing FCS as medium, as for example described in the Examples. The cells are subsequently incubated on a solid support, thereby allowing the cells to adhere to the support. Further, the cells are contacted with the wound exudate sample, or wound biofilm sample, which is optionally diluted, and the compounds of (2), wherein the contacting may be performed before or after adherence of the cells occurs. For example, the optionally diluted wound exudate sample, or wound biofilm sample, and the compounds of (2) may be independently added to the adherent cells, for example by pipetting or otherwise adding the liquid, or the optionally diluted wound exudate sample, or wound biofilm sample, may be added to the non-adherent cells, for example by pipetting or otherwise adding the liquid to the cells, followed by allowing the keratinocyte cells to adhere. The cells are subsequently incubated, preferably for 6 hours to 200 hours, preferably 24 hours to 100 hours. In the examples, the cells are incubated for 72 hours. Subsequently, the amount, preferably the cell number, of the keratinocyte cells, is determined, such as by fixing cells and determining total protein content. The cells may for example be fixed using paraformaldehyde. Further, a suitable dye, such as sulforhodamine B may be used for determining the amount, preferably the cell number, of the keratinocyte cells. The stained cells may then be quantified e.g. by determining absorbance or fluorescence at a suitable wavelength, depending on the dye. Preferably, the method is performed in 2D cell culture, which allows for culturing the cells adherently on a solid support.

A keratinocyte cell may be a primary keratinocyte cell or a keratinocyte cell line, in particular a human primary keratinocyte cell or a human keratinocyte cell line. In one preferred embodiment, the keratinocyte cells used in the present invention are selected from HaCaT cells and primary keratinocyte cells. HaCaT cells represent an established and widely used human keratinocyte cell line.

In a more preferred embodiment, the keratinocyte cells used in the present invention are HaCaT cells.

Therefore, in a preferred embodiment, measuring the proliferation of keratinocyte cells in the presence of a wound exudate sample, or wound biofilm sample, obtained from a skin wound and the compounds of (2) includes the following steps:
(i) culturing keratinocyte cells,
(ii) incubating the cells on a solid support, thereby allowing the cells to adhere to the support,
(iii) contacting the cells with the wound exudate sample, or wound biofilm sample, which is optionally diluted, and the compounds of (2), wherein the contacting may be performed before or after adherence of the cells occurs, and wherein the contacting of (1) and (2) may be performed simultaneously or sequentially, and
(iv) determining the amount, preferably the cell number, of the keratinocyte cells, such as by fixing cells and determining total protein content,
preferably wherein the method is performed in 2D cell culture.

Moreover, the accuracy and reliability can be further increased by including one or more additional assays which determine macrophage M1 and M2 markers and/or cytokine markers IL1alpha, IL1beta and/or TNFalpha in the context of wound exudate, or wound biofilm, obtained from the respective subject. These M1 and M2 markers may be cell surface protein markers, protein markers in the supernatant of macrophages or marker mRNAs in macrophages.

Macrophages are tissue-resident professional phagocytes and antigen-presenting cells (APC), which differentiate from circulating peripheral blood monocytes.

Activated macrophages of different phenotypes are classified by skilled persons into M1-macrophages and M2 macrophages. M1-macrophages are activated macrophages which comprise immune effector cells with an acute inflammatory phenotype. These are highly aggressive against bacteria and produce large amounts of lymphokines. The M2-macrophages are alternatively activated and anti-inflammatory.

A "M2 marker" is understood as a protein marker which is specific for M2 macrophages. Preferably, the marker is secreted by the macrophages. Suitable M2 markers are known in the art and are preferably selected from CCL22 and CCL18. The markers may be determined by methods known in the art, e.g. by using an immunological assay, even more preferably by using an ELISA assay.

A "M1 marker" is understood as a protein marker which is specific for M1 macrophages. Preferably, the marker is secreted by the macrophages. Suitable M1 markers are known in the art and are preferably selected from CXCL10 and IL-23p19. The markers may be determined by methods known in the art, e.g. by using an immunological assay, even more preferably by using an ELISA assay.

A "M1 cell surface marker" is understood as a protein marker which is expressed at the surface of macrophages, and which is specific for M1 macrophages. Suitable M1 cell surface markers are known in the art and are preferably selected from CD38, CD64 and CD197. The amount(s) and/or frequency distribution(s) of the cell surface markers may be determined by an immunological assay and/or a fluorescence assay, in particular by FACS analysis, whereby typically a frequency distribution is determined.

A "M2 cell surface marker" is understood as a protein marker which is expressed at the surface of macrophages, and which is specific for M2 macrophages. Suitable M2 cell surface markers are known in the art and are preferably selected from CD200 receptor (CD200R), CD206 and CD209. The amount(s) and/or frequency distribution(s) of the cell surface markers may be determined by an immunological assay and/or a fluorescence assay, in particular by FACS analysis, whereby typically a frequency distribution is determined.

A "M2 marker mRNA" is understood as an mRNA which is expressed by macrophages, and which is specific for M2 macrophages. Suitable M2 marker mRNAs are known in the art and are preferably selected CD200 receptor (CD200R), CD206, CD209, CCL22 and CCL18. The marker mRNAs may be determined by methods known in the art. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

A "M1 marker mRNA" is understood as an mRNA which is expressed by macrophages, and which is specific for M1 macrophages. Suitable M1 marker mRNAs are known in the art and are preferably selected from CD38, CD64, CD197, CXCL10 and IL-23p19. Preferably, the amount may be determined by contacting a probe which specifically binds to a marker mRNA, wherein the probe is optionally labelled, with the macrophage RNA under conditions which are conducive to hybridization, and detecting the hybridized probe. For example, the mRNA may be reversely transcribed into cDNA prior to detection.

The ratio of M1/M2 markers is indicative of a responsive subject, in combination with one or more cellular assays described above relating to measuring the proliferation of primary fibroblast cells, measuring the fibroblast-derived matrix (FDM) formation by primary fibroblast cells and measuring the proliferation of keratinocyte cells. In particular, an elevated ratio of M1/M2 markers, M1/M2 cell surface markers or M1/M2 marker mRNAs is indicative of a non-responsive subject, whereas a low ratio of M1/M2 markers, M1/M2 cell surface markers or M1/M2 marker mRNAs is indicative of a responsive subject.

Moreover, the amounts of the pro-inflammatory cytokines IL1 alpha, IL1beta and TNF-alpha secreted by macrophages in a macrophage/fibroblast co-culture were found to be particularly predictive for identifying healing skin wounds or non-healing skin wounds as well as for monitoring wound healing. In particular, higher amounts of these cytokines were found to be secreted in the presence of WE from non-healing wounds as compared to WE from healing wounds. Cytokines IL1 alpha, IL1beta and TNF-alpha are proteins, preferably human proteins, which are well-known to a skilled person. IL1alpha (also known as Interleukin-1α or IL-1α), IL1beta (also known as Interleukin-1β or IL-1β) and TNF-alpha (also known as Tumor Necrosis Factor α or TNF-α) may be determined by methods known in the art, e.g. by using an immunological assay, even more preferably by using an ELISA assay, as described in the Examples. IL1alpha, IL1 beta and TNF-alpha are known to be pro-inflammatory cytokines.

Therefore, in a further preferred embodiment of the present invention, one, two or three of the following assays iiib) to iiid) may be included in the uses and methods of the invention:

iiib) measuring the amount(s) of one or more M1 marker(s) and one or more M2 marker(s) in the supernatant of macrophages incubated with
  (1) a wound exudate sample or wound biofilm sample obtained from the skin wound of said subject, and
  (2) the compound(s) of (2) described for any of above embodiments of the invention,
  wherein the macrophages are in co-culture with fibroblasts, iiic) measuring the amount(s) and/or frequency distribution(s) of one or more M1 cell surface marker(s) and one or more M2 cell surface marker(s) on macrophages incubated with
  (1) a wound exudate sample or wound biofilm sample obtained from the skin wound of said subject, and
  (2) the compound(s) of (2) described for any of above embodiments of the invention,
  wherein the macrophages are in co-culture with fibroblasts, iiid) measuring the expression level(s) of one or more M1 marker mRNA(s) and one or more M2 marker mRNA(s) in macrophages incubated with
  (1) a wound exudate sample or wound biofilm sample obtained from the skin wound of said subject, and
  (2) the compound(s) of (2) described for any of above embodiments of the invention, wherein the macrophages are in co-culture with fibroblasts.

In one preferred embodiment of the present invention, the sample is a wound exudate sample. In another preferred embodiment, the sample is a wound biofilm sample. In a more preferred embodiment, the sample is a wound exudate sample.

Therefore, in a further preferred embodiment of the present invention, one, two or three of the following assays iiib) to iiid) or one, two, three or four of the following steps iiib) to iiie) may be included in the uses and methods of the invention:

iiib) measuring the amount(s) of one or more M1 marker(s) and one or more M2 marker(s) in the supernatant of macrophages incubated with
  (1) a wound exudate sample or wound biofilm sample obtained from said skin wound, and
  (2) the compound(s) of (2) described for any of above embodiments of the invention,
  wherein the macrophages are in co-culture with fibroblasts, and
  wherein the one or more M1 markers are selected from CXCL10 and IL-23p19, and the one or more M2 markers are selected from CCL22 and CCL18, iiic) measuring the amount(s) and/or frequency distribution(s) of one or more M1 cell surface marker(s) and one or more M2 cell surface marker(s) on macrophages incubated with
  (1) a wound exudate sample or wound biofilm sample obtained from said skin wound, and
  (2) the compound(s) of (2) described for any of above embodiments of the invention,
  wherein the macrophages are in co-culture with fibroblasts, and
  wherein the one or more M1 cell surface markers are selected from CD38, CD64 and CD197, and wherein the one or more M2 cell surface markers are selected from CD200 receptor, CD206 and CD209,
iiid) measuring the expression level(s) of one or more M1 marker mRNA(s) and one or more M2 marker mRNA(s) in macrophages incubated with
  (1) a wound exudate sample or wound biofilm sample obtained from said skin wound, and
  (2) the compound(s) of (2) described for any of above embodiments of the invention,
  wherein the macrophages are in co-culture with fibroblasts, and
  wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18,
iiie) measuring the amount(s) of one or more cytokine markers in the supernatant of macrophages incubated
  (1) with a wound exudate sample or wound biofilm sample obtained from said skin wound, and
  (2) the compound(s) of (2) described for any of above embodiments of the invention,
  wherein the macrophages are in co-culture with fibroblasts, and
  wherein the one or more cytokine markers are selected from IL-1alpha, IL-1beta and TNF-alpha.

Preferably, the subject is identified to be responsive to the treatment with the compound(s) of (2), in case the value of proliferation of primary fibroblast cells measured in step i) and/or the value of the fibroblast-derived matrix formation by primary fibroblast cells measured in step ii) and/or the value of the proliferation of keratinocyte cells in step iiia) is at least 20% above a control value established in the absence of the compound(s) of (2), and/or in case one or more of the following applies:
  the ratio of amount(s) of one or more M1 marker(s) to the amount(s) of one or more M2 marker(s) obtained in iiib) is/are below a control value established in the absence of the compound(s) of (2),
  the ratio of amount(s) and/or frequency distribution(s) of one or more M1 cell surface marker(s) to the amount(s) and/or frequency distribution(s) of one or more M2 cell surface marker(s) obtained in iiic) is/are below a control value established in the absence of the compound(s) of (2),
  the ratio of expression level(s) of one or more M1 marker mRNA(s) to the expression level(s) of one or more M2 marker mRNA(s) obtained in iiid) is/are below a control value established in the absence of the compound(s) of (2).

Preferably, the subject is identified to be responsive to the treatment with the compound(s) of (2), in case the value of proliferation of primary fibroblast cells measured in step i) and/or the value of the fibroblast-derived matrix formation by primary fibroblast cells measured in step ii) and/or the value of the proliferation of keratinocyte cells in step iiia) is at least 20% above a control value established in the absence of the compound(s) of (2), and/or in case one or more of the following applies:
  the ratio of amount(s) of one or more M1 marker(s) to the amount(s) of one or more M2 marker(s) obtained in iiib) is/are below a control value established in the absence of the compound(s) of (2),
  the ratio of amount(s) and/or frequency distribution(s) of one or more M1 cell surface marker(s) to the amount(s) and/or frequency distribution(s) of one or more M2 cell surface marker(s) obtained in iiic) is/are below a control value established in the absence of the compound(s) of (2), in particular wherein the ratio is selected from a CD38/CD209 ratio, a CD197/CD209 ratio and a CD197/CD206 ratio,
  the ratio of expression level(s) of one or more M1 marker mRNA(s) to the expression level(s) of one or more M2 marker mRNA(s) obtained in iiid) is/are below a control value established in the absence of the compound(s) of (2),
  the value obtained in iiie) is below a control value established in the absence of the compound(s) of (2).

It was found that the following M1 cell surface marker/M2 cell surface marker ratios are also predictive for responsiveness: a CD38/CD209 ratio, a CD197/CD209 ratio or a CD197/CD206 ratio below a control value established in the absence of the compound(s) of (2) is identifying a patient to be responsive to the treatment with the compound(s).

Therefore, in another preferred embodiment, the ratio of amount(s) and/or frequency distribution(s) is selected from a CD38/CD209 ratio, a CD197/CD209 ratio and a CD197/CD206 ratio.

The frequency distribution may be determined by determining the % age of cells which are positive for a given marker within a population, which is the most commonly used readout in FACS analysis. Alternatively, the amount may be determined by determining the quantity of cell surface expression, as a surrogate for the number of labelled molecules on the cell surface per individual cell when using labelled binding agents for the markers, as for example measured by the mean fluorescence intensity.

In a preferred embodiment, measuring the amount(s) of one or more M1 marker(s) and one or more M2 marker(s) in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the compounds of (2), and
(iv) determining the amount of one or more M1 markers and one or more M2 markers in the cell culture supernatant, preferably wherein the one or more M1 markers are selected from CXCL10 and IL-23p19, and/or the one or more M2 markers are selected from CCL22 and CCL18, more preferably wherein the markers are determined by using an immunological assay, even more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the compounds of (2), and optionally gentle mixing. The compounds are added after macrophages have differentiated; e.g. after 4 to 7 days. Further, the cells are incubated, preferably for 1 hour 100 hours, e.g. 4 hours to 100 hours. Subsequently, the amount of one or more M1 markers and one or more M2 markers in the cell culture supernatant is determined. The supernatant is typically harvested for such purpose and the markers are determined using a suitable assay, such as immunological assay. For example, an ELISA may be used.

In another preferred embodiment, measuring the amount(s) and/or frequency distribution(s) of one or more M1 cell surface marker(s) and one or more M2 cell surface marker(s) on macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the compounds of (2)
(iv) determining the amount(s) and/or frequency distribution(s) of one or more M1 cell surface marker(s) and one or more M2 cell surface marker(s) on the cell surface of macrophages.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the compounds of (2), and optionally gentle mixing. The compounds are added after macrophages have differentiated; e.g. after 4 to 7 days. Further, the cells are incubated, preferably for 1 hour 100 hours, e.g. 4 hours to 100 hours. Subsequently, the amount(s) and/or frequency distribution(s) of one or more M1 cell surface marker(s) and one or more M2 cell surface marker(s) on the cell surface of macrophages is/are determined. For example, the cells may be harvested and subjected to FACS analysis, gating on the monocyte/macrophage population. Geometric means of mean fluorescence intensities can be used to quantify surface marker expression.

Preferably, the one or more M1 cell surface markers are selected from CD38, CD64 and CD197, and/or the one or more M2 cell surface markers are selected from CD200 receptor (CD200R), CD206 and CD209, more preferably wherein the amount(s) and/or frequency distribution(s) of the cell surface markers are determined by an immunological assay and/or a fluorescence assay, in particular by FACS analysis.

It was found that the following M1 cell surface marker/M2 cell surface marker ratios are also predictive for determining responsiveness: a CD38/CD209 ratio, a CD197/CD209 ratio and a CD197/CD206 ratio. A CD38/CD209 ratio, a CD197/CD209 ratio or a CD197/CD206 ratio below a control value established in the absence of the compound(s) of (2) is identifying a patient to be responsive to the treatment with the compound(s).

Therefore, in another preferred embodiment, the ratio of amount(s) and/or frequency distribution(s) is selected from a CD38/CD209 ratio, a CD197/CD209 ratio and a CD197/CD206 ratio.

Accordingly, in another preferred embodiment, the one or more M1 cell surface marker is selected from CD38 and the one or more M2 cell surface marker is selected from CD209, or the one or more M1 cell surface marker is selected from CD197 and the one or more M2 cell surface marker is selected from CD209 and CD206.

In one preferred embodiment, step (iv) comprises contacting the macrophages with binding agents, preferably antibodies, which specifically recognize one or more M1 surface marker(s) and one or more M2 surface marker(s), wherein the binding agents are optionally labelled, in particular labelled with a fluorescent label, and determining the amount of binding molecules bound to the macrophages, in particular by determining mean fluorescence intensity, thereby determining the amount(s) of the cell surface markers. For example, antibodies specifically recognizing the surface markers and which contain a fluorescent label may be used.

In another preferred embodiment, step (iv) comprises contacting the macrophages with binding agents, preferably antibodies, which specifically recognize one or more M1 surface marker(s) and one or more M2 surface marker(s), wherein the binding agents are optionally labelled, in particular labelled with a fluorescent label, and determining the percentages of cells which are positive for the one or more M1 surface marker(s) and the one or more M2 surface marker(s), respectively, within a cell population, in particular wherein FACS analysis is performed, thereby determining the frequency distribution(s) of the cell surface markers. For example, antibodies specifically binding to the surface markers and which contain a fluorescent label may be used.

Determination of proteins as binding agents of a marker protein can be performed using any of a number of known methods for identifying and obtaining proteins that specifically interact with proteins or polypeptides, for example, a yeast two-hybrid screening system such as that described in U.S. Pat. Nos. 5,283,173 and 5,468,614, or the equivalent. A binding agent which specifically recognizes a marker has preferably at least an affinity of $10^7$ l/mol for its corresponding target molecule. The binding agent which specifically recognizes a marker preferably has an affinity of $10^8$ l/mol or even more preferred of $10^9$ l/mol for its target marker molecule. As the skilled person will appreciate, the term specific is used to indicate that other biomolecules present in the sample do not significantly bind to the binding agent which specifically recognizes the marker. Preferably, the level of binding to a biomolecule other than the target marker molecule results in a binding affinity which is only 10% or less, more preferably only 5% or less of the affinity to the target marker molecule, respectively. A preferred specific binding agent will fulfill both the above minimum criteria for affinity as well as for specificity.

A binding agent which specifically recognizes a marker preferably is an antibody reactive with the marker. The term antibody refers to a polyclonal antibody, a monoclonal antibody, antigen binding fragments of such antibodies, single chain antibodies as well as to genetic constructs comprising the binding domain of an antibody. The term "antibodies" includes polyclonal antibodies, monoclonal antibodies, fragments thereof such as F(ab')2, and Fab fragments, as well as any naturally occurring or recombinantly produced binding partners, which are molecules that specifically bind to a marker protein. Any antibody fragment retaining the above criteria of a specific binding agent can be used.

For measurement, the sample obtained from an individual is incubated with the binding agent that specifically recognizes the marker in question under conditions appropriate for formation of a binding agent marker-complex. Such conditions need not be specified, since the skilled artisan without any inventive effort can easily identify such appropriate incubation conditions. The amount of binding agent marker-complex is measured and used in the methods and uses of the invention. As the skilled artisan will appreciate there are numerous methods to measure the amount of the specific binding agent marker-complex all described in detail in relevant textbooks (cf., e.g., Tijssen P., supra, or Diamandis, E. P. and Christopoulos, T. K. (eds.), Immunoassay, Academic Press, Boston (1996)).

Particularly, monoclonal antibodies to the marker(s) are used in a quantitative (amount or concentration of the marker(s) is determined) immunoassay.

For example, the marker may be detected in a sandwich type assay format. In such assay a first specific binding agent is used to capture the marker in question on the one side and a second specific binding agent (e.g. a second antibody), which is labeled to be directly or indirectly detectable, is used on the other side.

The second specific binding agent may contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of binding agent remaining on the support after wash. The amount of the second binding agent that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (for review see, e.g., Scouten, W. H., Methods in Enzymology 135:30-65, 1987). Spectroscopic methods can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well known techniques.

Immunoassays for measuring marker proteins of the invention include for example ELISA, enzyme immunoassay (EIA) and electro-chemiluminescence immunoassay (ECLIA) for the quantitative determination of a marker protein described herein.

In another preferred embodiment, measuring the expression level(s) of one or more M1 marker mRNA(s) and one or more M2 marker mRNA(s) in macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample, or wound biofilm sample, which is optionally diluted, and the compounds of (2), and
(iv) determining the expression level(s) of one or more M1 marker mRNA(s) and one or more M2 marker mRNA(s) in the macrophages.

In one preferred embodiment of the present invention, the sample is a wound exudate sample. In another preferred embodiment, the sample is a wound biofilm sample. In a more preferred embodiment, the sample is a wound exudate sample.

Preferably, the one or more M1 marker mRNA(s) are selected from CD38, CD64, CD197, CXCL10 and IL-23p19, and/or the one or more M2 marker mRNA(s) are selected from CD200 receptor (CD200R), CD206, CD209, CCL22 and CCL18, more wherein the method comprises contacting a probe which specifically binds to a marker mRNA, wherein the probe is optionally labelled, with the macrophage RNA under conditions which are conducive to hybridization, and detecting the hybridized probe.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample, or wound biofilm sample, which is optionally diluted, for example by pipetting the sample to the cells, and the compounds of (2), and optionally gentle mixing. The compounds are added after macrophages have differentiated; e.g. after 4 to 7 days. Further, the cells are incubated, preferably for 1 hour 100 hours, e.g. 4 hours to 100 hours. Subsequently, the expression level(s) of one or more M1 marker mRNA(s) and one or more M2 marker mRNA(s) in the macrophages is determined. For example, the cells may be harvested and mRNA expression level(s) may be determined using suitable probes. For example, the expression level of a housekeeping gene such as actin or GAPDH may be determined and the expression level(s) of M1 or M2 marker RNA(s) may be determined as expression level relative to a housekeeping gene.

In another preferred embodiment, measuring the amount(s) of one or more cytokine markers selected from IL-1alpha, IL-1beta and TNF-alpha in the supernatant of macrophages incubated with a wound exudate sample or wound biofilm sample obtained from a skin wound includes the following steps:
(i) co-culturing primary human monocyte cells with (a) human dermal fibroblast cells in 2D cell culture or (b) fibroblast-derived matrices,
(ii) incubating the cells until macrophage differentiation is reached, optionally wherein CD163 is used as a cell surface marker of macrophage differentiation,
(iii) contacting the cells with a wound exudate sample or wound biofilm sample, which is optionally diluted, and the compounds of (2), and
(iv) determining the amount of one or more cytokine markers selected from IL-1alpha, IL-1beta and TNF-alpha in the cell culture supernatant,
preferably wherein the cytokine markers are determined by using an immunological assay, more preferably by using an ELISA assay.

In one preferred embodiment of the present invention, the sample is a wound exudate sample. In another preferred embodiment, the sample is a wound biofilm sample. In a more preferred embodiment, the sample is a wound exudate sample.

For example, primary human monocyte cells may be co-cultured with human dermal fibroblast cells in 2D cell culture, or with fibroblast-derived matrices. Methods for generating fibroblast-derived matrices are described above, as well as in the examples. Subsequently, the cells are incubated until macrophage differentiation is reached. For example, CD163 can be used as a cell surface marker of macrophage differentiation. Further, the cells are contacted with a wound exudate sample or wound biofilm sample, which is optionally diluted, and the compounds of (2), wherein the contacting may be performed for example by pipetting the sample to the cells, and optionally gentle mixing. The compounds are added after macrophages have differentiated; e.g. after 4 to 7 days. Further, the cells are incubated, preferably for 1 hour to 100 hours, e.g. 4 hours to 100 hours. Subsequently, the amount of one or more of IL-1alpha, IL-1beta and TNF-alpha in the cell culture supernatant is determined. The supernatant is typically harvested for such purpose and the cytokine markers are determined using a suitable assay, such as immunological assay. For example, an ELISA may be used. In a preferred embodiment, the sample is a wound exudate sample.

The amounts of IL-1alpha, IL-1beta and TNF-alpha in the supernatant of macrophages are indicative for a patient responsive to the treatment with the compound(s) of (2). Accordingly, a patient is identified to be responsive to the treatment with the compound(s) of (2) in case the value obtained for the amounts of IL-1alpha, IL-1beta and TNF-alpha is below a control value established in the absence of the compound(s) of (2).

In yet another embodiment, the present invention relates to a kit or kit-of-parts, comprising:
(a) a pharmaceutical composition comprising Rucaparib and/or Talazoparib and/or Veliparib and/or Olaparib and/or AZD 2461, or a pharmaceutically acceptable salt thereof, and
(b) a diagnostic kit comprising one or more of the following:
  i) primary fibroblast cells,
  ii) a support having a plurality of defined areas or cavities, wherein a subset of areas or cavities are (i) coated with adhesion enhancing agent, and/or (ii) are filled with fibroblast-derived matrix (FDM),
  iii) a matrix promoting supplement.

It is understood that the preferred embodiments described in the context of other embodiments of the present invention also apply this embodiment of the invention.

The pharmaceutical compositions, cells and matrix promoting supplement may be provided in containers, vials, syringes, ampules or the like.

The diagnostic kit of b) optionally further comprises one or more of the following:
iv) keratinocyte cells,
v) a matrix promoting supplement,
vi) monocyte cells, and
vii) binding agents, preferably antibodies, which specifically recognize one or more M1 marker(s) and one or more M2 marker(s), and/or binding agents, preferably antibodies, which specifically recognize one or more M1 surface marker(s) and one or more M2 surface marker(s), and/or probes which specifically recognize one or more M1 marker mRNA(s) and one or more M2 marker mRNA(s)
viii) binding agents, preferably antibodies, which specifically recognize one or more one or more cytokine markers selected from IL-1alpha, IL-1beta and TNF-alpha.

In a more preferred embodiment, the diagnostic kit of b) further comprises viii) binding agents, preferably antibodies, which specifically recognize one or more one or more cytokine markers selected from IL-1alpha, IL-1beta and TNF-alpha.

Preferred M1 and M2 marker(s), cell surface marker(s) and/or marker mRNA(s) are described above.

In one preferred embodiment, the binding agents, preferably antibodies of vii) above are binding agents, preferably antibodies, which specifically recognize one or one more M1 cell surface marker(s) and one or more M2 cell surface marker(s), wherein the one ore more M1 cell surface markers are selected from CD38, CD64 and CD197, and wherein the one or more M2 cell surface markers are selected from CD200 receptor, CD206 and CD209, and, optionally:
binding agents, preferably antibodies, which specifically recognize one or more M1 marker(s) and one or more M2 marker(s), and/or probes which specifically recognize one or more M1 marker mRNA(s) and one or more M2 marker mRNA(s), wherein the one or more M1 markers are selected from CXCL10 and IL-23p19, and the one or more M2 markers are selected from CCL22 and CCL18, and wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18, and Accordingly, in another more preferred embodiment, the one or more M1 cell surface marker is selected from CD38 and the one or more M2 cell surface marker is selected from CD209, or the one or more M1 cell surface marker is selected from CD197 and the one or more M2 cell surface marker is selected from CD209 and CD206.

In one preferred embodiment, the keratinocyte cells are selected from HaCaT cells and primary keratinocyte cells, in particular human primary keratinocyte cells.

In a more preferred embodiment, the keratinocyte cells used in the present invention are HaCaT cells.

Fibroblast-derived matrix (FDM) is obtainable by (i) seeding primary human dermal fibroblast cells on a support, which is pre-coated with an adhesion enhancing agent, such as gelatin, (ii) culturing the cells on the support, preferably until confluence is reached and (iii) contacting the cells with a matrix promoting supplement, such as Vitamin C or a physiologically acceptable salt thereof, or 2-phospho-L-ascorbic acid or a physiologically acceptable salt thereof, or a combination of EGF and insulin. FDM may be formed in situ or may be transferred to the support after formation.

Moreover, supports, such as chips are preferred, which allow for performing the in vitro methods of the invention or method steps of the medical uses of the invention. For example, a chip may be provided, which allows for identifying subjects to be responsive to a treatment of impaired wound healing with Rucaparib and/or Talazoparib and/or Veliparib and/or Olaparib, and/or AZD 2461 or the pharmaceutically acceptable salt thereof.

Therefore, in another preferred embodiment, the present invention relates to a kit or kit-of-parts of the invention, wherein the support ii) of the diagnostic kit (b) is suitable for performing a method of the present invention or method steps of the medical uses of the invention, wherein the support comprises a plurality of defined areas or cavities and wherein:
a) a subset of areas or cavities are coated with an adhesion enhancing agent,
b) a subset of areas or cavities are coated with an adhesion enhancing agent and/or filled with fibroblast-derived matrix (FDM),
c) a subset of areas or cavities are untreated,
d) optionally:
  d1) a subset of areas or cavities contain binding agents, preferably antibodies, which specifically recognize one or more M1 marker(s), and
  d2) a subset of areas or cavities contain binding agents, preferably antibodies, which specifically recognize one or more one or more M2 marker(s),
e) optionally:
  e1) a subset of areas or cavities contain binding agents, preferably antibodies, which specifically recognize one or more M1 surface marker(s), and
  e2) a subset of areas or cavities contain binding agents, preferably antibodies, which specifically recognize one or more M2 surface marker(s),
f) optionally:
  f1) a subset of areas or cavities contain probes which specifically recognize one or more M1 marker mRNA(s), and
  f2) a subset of areas or cavities contain probes which specifically recognize one or more M2 marker mRNA(s), and
g) optionally: a subset of areas or cavities contain binding agents, preferably antibodies, which specifically recognize one or more cytokine markers selected from IL-1 alpha, IL-1 beta and TNF-alpha
wherein the subsets a) to g) are not overlapping, preferably
(x) at least some of the areas or cavities pursuant to a) further contain primary fibroblast cells, and/or
(xi) at least some of the areas or cavities pursuant to (x) or b) further contain monocyte cells, and/or
(xii) at least some of the areas or cavities pursuant to c) further contain primary fibroblast cells, and/or
(xiii) at least some of the areas or cavities pursuant to c) further contain keratinocyte cells,
wherein the areas or cavities pursuant to (xii) and (xiii) are not overlapping.

In one preferred embodiment, the one or more M1 markers are selected from CXCL10 and IL-23p19, and the one or more M2 markers are selected from CCL22 and CCL18.

In one preferred embodiment, the one or more M1 cell surface markers are selected from CD38, CD64 and CD197, and wherein the one or more M2 cell surface markers are selected from CD200 receptor, CD206 and CD209.

In one preferred embodiment, the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18.

In one more preferred embodiment, the support of the kit or kit-of-parts is a chip, array, such as a microarray or nanoarray, a plate, such a multiwell plate, or a dish, and/or the support is a plastic support.

The solid support of the kit or kit-of-parts preferably contains a plurality of defined cavities. Cavities allow for filling of the space and therefore allow for a 3D cell culture. For example, a multiwell plate or a microarray or nanoarray comprising a plurality of defined cavities may be used. In the examples, a multiwell plate was successfully used. Preferably, the solid support does not substantially interfere with the viability of the cells and/or is suitable for culturing cells, for example the support may be a plastic support. For 3D cell culture, the solid support may contain a plurality of defined wells. For example, multi-well plates may be used. In one preferred embodiment, the support comprises 2, 3, 4, 5, 6, 7, 8, 9, 10 or more defined areas or cavities, such as 2, 3, 4, 5, 6, 7, 8, 9 or 10 to $10^5$, 2, 3, 4, 5, 6, 7, 8, 9 or 10 to $10^4$, 2, 3, 4, 5, 6, 7, 8, 9 or 10 to $10^3$, or 2, 3, 4, 5, 6, 7, 8, 9 or 10 to $10^2$ defined areas or cavities.

The pharmaceutical compositions contain the respective active agent(s), and optionally one or more pharmaceutically acceptable excipients and/or pharmaceutically acceptable excipients. The active agent(s) is/are Rucaparib and/or Talazoparib and/or Veliparib and/or Olaparib and/or AZD 2461 or a pharmaceutically acceptable salt thereof, respectively. In a preferred embodiment, the kit or kit-of-parts, comprising in (a) a pharmaceutical composition contains as active agent Rucaparib or Talazoparib or Veliparib or Olaparib or AZD 2461, or a pharmaceutically acceptable salt thereof.

A "pharmaceutically acceptable carrier" means a carrier or diluent that does not cause significant irritation to an organism and does not abrogate the biological activity and properties of the administered active agent. The carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

In a preferred embodiment of any of the above aspects of the invention, Rucaparib and/or Talazoparib and/or Veliparib and/or Olaparib and/or AZD 2461 or a pharmaceutically acceptable salt thereof is/are formulated for systemic, preferably oral or intravenous administration, or Rucaparib and/or Talazoparib and/or Veliparib and/or Olaparib and/or AZD 2461 or a pharmaceutically acceptable salt thereof is/are formulated for local administration, in particular for topical, mucosal or subcutaneous administration. For example, formulations for oral or intravenous administration of Rucaparib and/or Talazoparib and/or Veliparib and/or Olaparib and/or AZD 2461 or a pharmaceutically acceptable salt thereof are known in the art. Moreover, the skilled person is aware of techniques for providing formulations for local administration, in particular for topical, mucosal or subcutaneous administration. For example, Rucaparib and/ or Talazoparib and/or Veliparib and/or Olaparib and/or AZD 2461 or a pharmaceutically acceptable salt thereof may be formulated as being incorporated into a wound dressing or bandage, or as gel, semi-solid gel, cream, lotion, ointment, spray, dispersion, salve, liposomal or nanoparticulate formulation or for application by microneedles.

Therefore, in another preferred embodiment of the present invention, Rucaparib and/or Talazoparib and/or Veliparib and/or Olaparib, and/or AZD 2461 or the pharmaceutically acceptable salt thereof for use of the present invention is/are formulated for systemic, preferably oral or intravenous administration.

In another preferred embodiment of the present invention, Rucaparib and/or Talazoparib and/or Veliparib and/or Olaparib, and/or AZD 2461 or the pharmaceutically acceptable salt thereof for use of the present invention is/are formulated for local administration, in particular for topical, mucosal or subcutaneous administration.

"Ascorbic acid" according to the present invention refers to L-(+) ascorbic acid or 1,2-Dihydroxyethyl]-3,4-dihydroxy-5-hydrofurane-2-one, and derivatives thereof which are metabolized to L-(+) ascorbic acid in the human body, such as dehydroascorbic acid (DHA) or a pharmaceutically acceptable salt thereof. A preferred ascorbic acid or pharmaceutically acceptable salt thereof according to the present invention is selected from L-(+) ascorbic acid or a pharmaceutically acceptable salt thereof and dehydroascorbic acid or a pharmaceutically acceptable salt thereof, more preferably L-(+) ascorbic acid or a pharmaceutically acceptable salt thereof. Preferred pharmaceutically acceptable salts of ascorbic acid include the sodium and calcium salt.

The term "PARP inhibitor" as used herein refers to an inhibitor or antagonist of Poly(ADP-ribose) polymerases (PARP 1 and/or PARP2) activity. In a preferred embodiment, a PARP inhibitor inhibits PARP1 and optionally further inhibits PARP2. A PARP inhibitor or antagonist is a compound that selectively inhibits the activity of PARP and refers to a compound that, when administered to a subject, reduces the PARP activity within the subject. The compounds for use of the present invention, Rucaparib and/or Talazoparib and/or Veliparib and/or Olaparib and/or AZD 2461 or a pharmaceutically acceptable salt thereof, are selective PARP inhibitors.

"Glucocorticoids" or "GCs" are a class of corticosteroids. Glucocorticoids are corticosteroids that bind to the glucocorticoid receptor (GR). Glucocorticoids are well known in the art and in medical practice. Numerous glucocorticoids have marketing approval for the treatment of diseases and are widely used in medical practice. Suitable glucocorticoids include cortisol, cortisone acetate, prednisone, prednisolone, methylprednisolone, chloroprednisone, cloprednol, difluprednate, fludrocortisone acetate, fluocinolone, fluperolone, fluprednisolone, loteprednol, prednicarbate, tixocortol, triamcinolone, triamcinolone acetonide, dexamethasone, betamethasone, beclometasone, deoxycorticosterone acetate, alclometasone, clobetasol, clobetasone, clocortolone, desoximetasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, ulobetasol, amcinonide, budesonide, ciclesonide, deflazacort, desonide, formocortal, fluclorolone acetonide, fludroxycortide, flunisolide, fluocinolone acetonide, fluocinonide, halcinonide, hydroxymethylprogesterone, and medroxyprogesterone and pharmaceutically acceptable salts thereof.

Therefore, in yet another preferred embodiment of any of the above aspects of the invention, the glucocorticoid is selected from the group consisting of cortisol, cortisone acetate, prednisone, prednisolone, methylprednisolone, chloroprednisone, cloprednol, difluprednate, fludrocortisone acetate, fluocinolone, fluperolone, fluprednisolone, loteprednol, prednicarbate, tixocortol, triamcinolone, triamcinolone acetonide, dexamethasone, betamethasone, beclometasone, deoxycorticosterone acetate, alclometasone, clobetasol, clobetasone, clocortolone, desoximetasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, ulobetasol, amcinonide, budesonide, ciclesonide, deflazacort, desonide, formocortal, fluclorolone acetonide, fludroxycortide, flunisolide, fluocinolone acetonide, fluocinonide, halcinonide, hydroxymethylprogesterone, and medroxyprogesterone or a pharmaceutically acceptable salt thereof. Typically, for systemic applications, the glucocorticoid dose will be in the range of about 0.1 to 1000 mg/day, depending on the glucocorticoid. Topical formulations of glucocorticoids are typically administered in a concentration of 0.001 to 10% (w/v), 0.001 to 6% (w/v) or 0.001 to 1% (w/v), such as 0.01 to 0.1% (w/v), such as a cream, gel, lotion, ointment, liposomal or nanoparticulate formulation or the like.

A "protein growth factor" is a protein which exhibits an enhancing and/or stimulatory effect on the proliferation of at least one cell type present in the skin of an animal. In a preferred embodiment, the protein growth factor does not cause cancer when administered to a subject, in particular when administered topically to a subject and/or the protein growth factor is suitable for administration to a subject for therapeutic and/or preventive purposes. In a preferred embodiment, the protein growth factor is a human protein growth factor. In yet another preferred embodiment, the protein growth factor is a recombinant protein growth factor, in particular recombinant protein growth factor. In a more preferred embodiment, the protein growth factor is selected from a platelet derived growth factor (PDGF), transforming growth factor beta (TGF-ß), basic fibroblast growth factor (bFGF), keratinocyte growth factor (KGF), epidermal growth factor (EGF), Insulin-like growth factor 1 (IGF-1), vascular endothelial growth factor (VEGF) and (hepatocyte growth factor) HGF. In an even more preferred embodiment, the protein growth factor is selected from a platelet derived growth factor (PDGF), transforming growth factor beta (TGF-ß), and basic fibroblast growth factor (bFGF), most preferably the protein growth factor is PDGF, in particular becaplermin. A PDGF is preferably selected from a PDGF containing a homodimer or heterodimer of the group selected from PDGF-A, PDGF-B, PDGF-C and PDGF-D, more preferably selected from PDGF-A and PDGF-B. In an even more preferred embodiment, the PDGF is the homodimer of the B chain of platelet-derived growth factor, designated PDGF-BB or becaplermin. In a preferred embodiment, KGF is KGF-2, in particular human KGF-2. In another preferred embodiment, the protein growth factor is human epidermal growth factor (EGF), in particular recombinant human EGF (rhEGF).

In a yet further embodiment, the present invention relates to a method of preventing or treating impaired skin wound healing in a subject, comprising administering to a subject in need thereof a therapeutically effective amount of Rucaparib and/or Talazoparib and/or Veliparib and/or Olaparib, and/or AZD 2461, or a pharmaceutically acceptable salt thereof.

"Effective amount" refers to the amount sufficient to induce a desired biological, pharmacological, or therapeutic outcome in a subject. A therapeutically effective amount of a compound can be employed as a zwitterion or as a pharmaceutically acceptable salt. A therapeutically effective amount means a sufficient amount of the compound to treat or prevent impaired skin wound healing at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

FIGURE LEGEND

FIG. 1: shows profiling of compound veliparib in the human dermal fibroblast proliferation assay (2D) with or without wound exudate from patients #78 and #43. Squares: no WE added; circles: WE added from patient #43; triangles: WE added from patient #78. X-axis shows concentration of veliparib. Veliparib completely reversed inhibition of wound exudate (WE)-induced fibroblast proliferation with wound exudate #78 (diabetic patient).

FIG. 2: shows profiling of compound veliparib in the human dermal fibroblast proliferation assay (2D) with or without wound exudate from a plurality of patients. Squares: WE added from patient #49; circles: WE added from patient #43; triangles: WE added from patient #78; diamonds: WE added from patient #27. X-axis shows concentration of veliparib. The effect of veliparib was most prominent in the two patients with diabetes.

FIG. 3: shows the reproducibility of the effect of veliparib in fibroblast 2D culture with different samples of one patient. The different samples from one patient are denoted #77 and #78. The patient has the following co-morbidities: diabetes, adipositas, and kidney transplantation. circles: WE added from sample #78; diamonds: WE added from sample #77. X-axis shows concentration of veliparib. The effect of veliparib was reproducible in different samples of the same patient (day 1 and day 8). This patient received a glucocorticoid (prednisolone) as co-medication. This suggests that veliparib is in particular suitable for treating impaired skin wound healing in patients already receiving a glucocorticoid as therapy. This finding is surprising as it is opposed to the "dogma" in the prior art describing glucocorticoids to impair wound healing.

FIG. 4: shows the effect of talazoparib, veliparib and the glucocorticoid dexamethasone in the 3D fibroblast culture regarding the formation of fibroblast-derived matrix as optically evaluated by microscopy. DEXA: dexamethasone. Talazoparib and veliparib, "cleaned up" WE-induced fibroblast matrix inhibition. Surprisingly, the effect of talazoparib was found to be particularly strong and beneficial. Moreover, the combination of veliparib with dexamethasone was superior to each substance alone.

Figure 5:
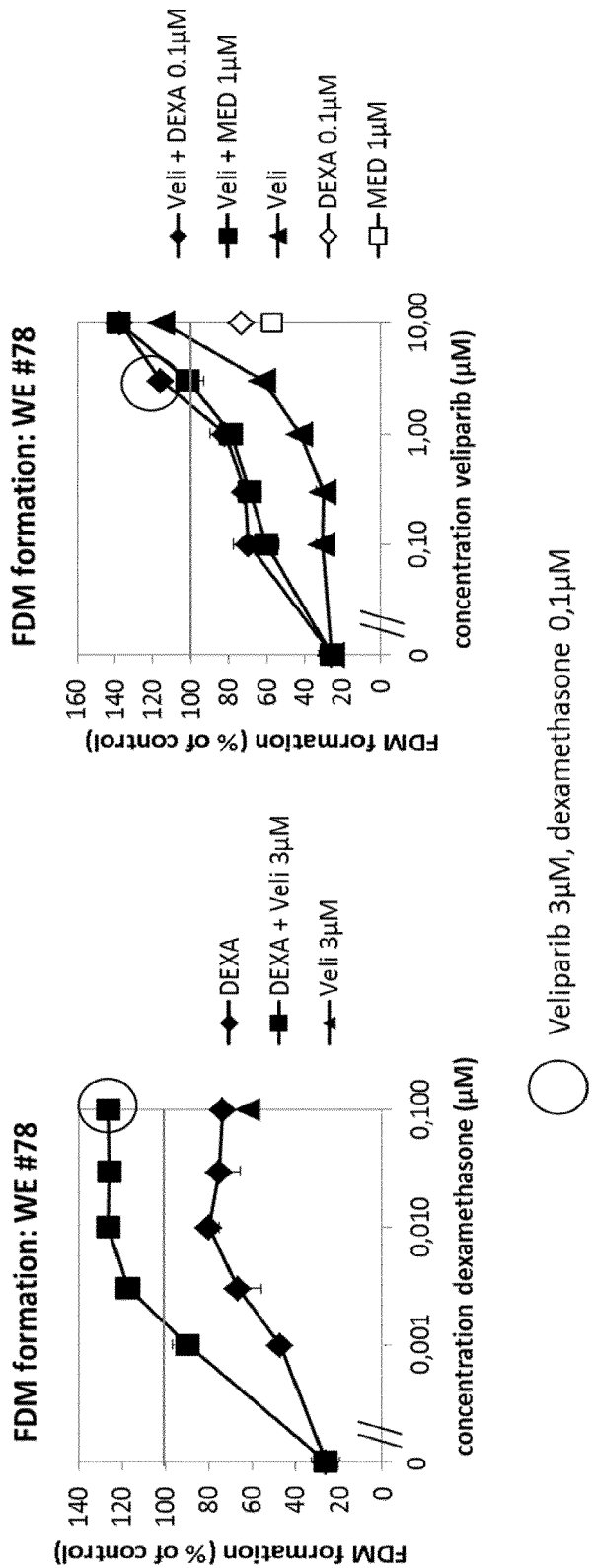

FIG. 5: shows the effect of talazoparib, veliparib and glucocorticoids in 3D fibroblast culture regarding the formation of fibroblast-derived matrix in patient #78. DEXA: dexamethasone; veli: veliparib; MED: medroxyprogesterone. Glucocorticoids DEXA (=dexamethasone) and MED (=medroxyprogesterone) enhance the effect of veliparib on rescuing FDM formation after WE treatment. Veliparib, in turn, enhances the effect of glucocorticoids in this patient (co-morbidities: diabetes, immunosuppression after kidney transplantation).

Figure 6:
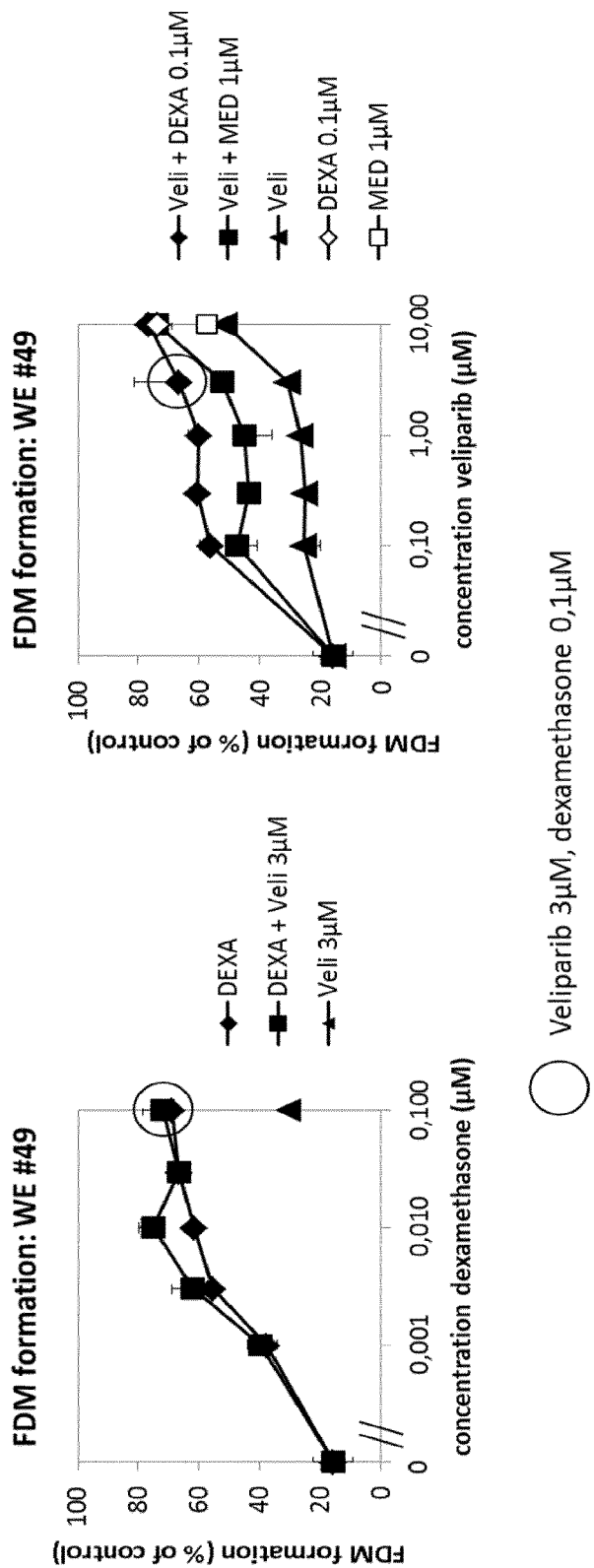

FIG. 6: shows the effect of talazoparib, veliparib and glucocorticoids in 3D fibroblast culture regarding the formation of fibroblast-derived matrix in patient #49 (patient is non-diabetic and non-immunosuppressed). DEXA: dexamethasone; veli: veliparib; MED: medroxyprogesterone. In this patient (non-diabetic, non-immunosuppressed), the effect of veliparib could be enhanced with glucocorticoids, but not vice versa. Therefore, veliparib is surprisingly found to be useful in treating impaired skin wound healing, in particular in patients treated with glucocorticoids.

FIG. 7: shows the effect of a plurality of PARP inhibitors in 3D fibroblast culture with WE from patient #78. Talazoparib was the most active of the PARP inhibitors tested in 3D culture. This is in line with its higher potency in tumor models in vitro and in vivo. Filled diamonds: veliparib; filled squares: olaparib; filled triangles: AZD-2461; filled circles: niraparib; open diamonds2: rucaparib; open squares2: talazoparib; open triangles2: AG-14361. A strong and consistent positive effect could only be shown for talazoparib, veliparib, olaparib, rucaparib, and AZD-2461. Surprisingly, niraparib, which inhibits both PARP1 and PARP with an 1050 in the low nM range, does not show any activity. Also, AG-14351, which inhibits PARP1 with an 1050 in the low nM range, exhibits only a very weak effect at a concentration of 10 µM.

FIG. 8: shows PARP inhibitor compound profiling: Mechanistically related PARP inhibitor compounds in 2D fibroblast culture with WE from patient #78. Filled diamonds: veliparib; filled squares: olaparib; filled triangles: AZD-2461; filled circles: niraparib; open diamonds: rucaparib; open squares: talazoparib; open triangles: AG-14361. The effect from 3D fibroblast culture relating to FDM formation could be reproduced in the 2D assay on human dermal fibroblast proliferation. Accordingly, a strong and consistent positive effect could only be shown for talazoparib, veliparib, olaparib, rucaparib, and AZD-2461. Surprisingly, niraparib, which inhibits both PARP1 and PARP with an 1050 in the low nM range, does not show any activity. Also, AG-14351, which inhibits PARP1 with an 1050 in the low nM range, exhibits only a very weak effect at a concentration of 10 µM.

FIG. 9: shows additional PARP inhibitor compound profiling data: Mechanistically related PARP inhibitor compounds in 2D fibroblast culture with WE from patient #43. Filled diamonds: veliparib; filled squares: talazoparib; filled triangles: rucaparib; filled circles: PJ-34; open triangles: 1,5 IQD; open circles: 3-AB; open diamonds: BGP-15. Accordingly, a strong and consistent positive effect could only be shown for talazoparib, Veliparib and rucaparib. The literature PARP inhibitor compounds discussed in the context of skin disorders (PJ-34, 1,5-IQD; 3-AB and BGP-15) are either inactive or exhibit a very weak activity.

FIG. 10: shows additional PARP inhibitor compound profiling data: Mechanistically related PARP inhibitor compounds in 2D fibroblast culture with WE from patient #78.

Filled diamonds: veliparib; filled squares: talazoparib; filled triangles: rucaparib; filled circles: PJ-34; open triangles: 1,5 IQD; open circles: 3-AB; open diamonds: BGP-15. Accordingly, a strong and consistent positive effect could only be shown for talazoparib, Veliparib and rucaparib. The literature PARP inhibitor compounds discussed in the context of skin disorder (PJ-34, 1,5-IQD; 3-AB and BGP-15) are either inactive or exhibit a very weak activity.

FIG. 11: shows additional PARP inhibitor compound profiling; mechanistically related compounds in 2D fibroblast culture without WE (control). Filled diamonds: veliparib; filled squares: talazoparib; filled triangles: rucaparib; filled circles: PJ-34; open triangles: 1,5 IQD; open circles: 3-AB; open diamonds: BGP-15. Most compounds have no effect on fibroblast proliferation in the absence of WE. Talazoparib even exhibits a weak inhibitory activity.

FIG. 12: shows 2D fibroblast culture results with wound exudate from patient #78: 3 different PARP inhibitors (veliparib, talazoparib and PJ-34)±dexamethasone±Vit. C. Both dexamethasone and vitamin C synergistically enhance the PARP inhibitor compound effects. Veliparib and talazoparib surprisingly show strongly beneficial effects. In contrast thereto, PJ-34 exhibits only a weak effect.

Figure 13:
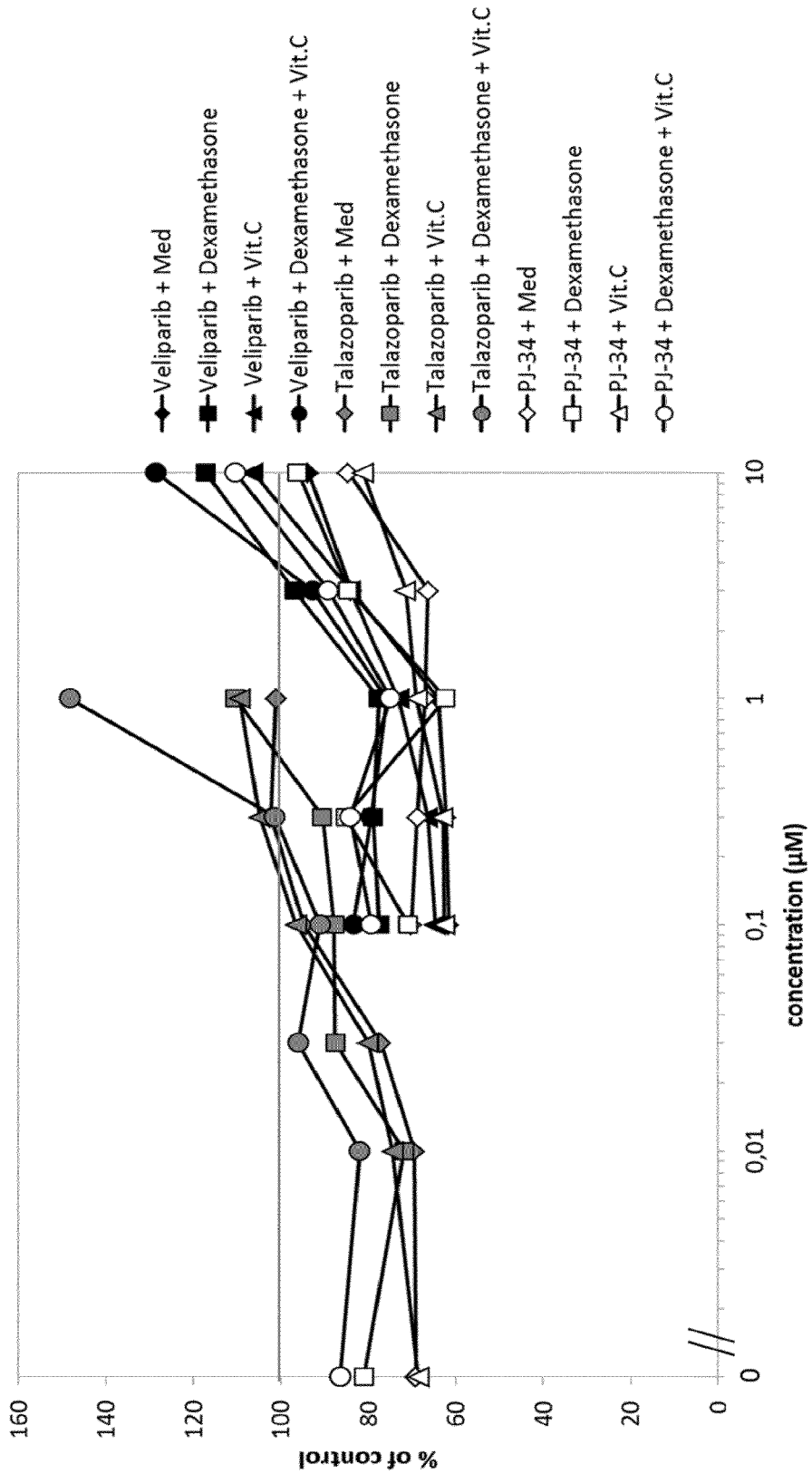

FIG. 13: shows 2D fibroblast culture results with wound exudate from patient #43: 3 different PARP inhibitors (veliparib, talazoparib and PJ-34)±dexamethasone±Vit. C. Both dexamethasone and vitamin C synergistically enhance the PARP inhibitor compound effects. Veliparib and talazoparib surprisingly show strongly beneficial effects. In contrast thereto, PJ-34 exhibits only a weak effect.

FIG. 14: shows 2D fibroblast culture (human dermal fibroblast (HDF) proliferation assay) results without wound exudate as compared to with wound exudate #78: veliparib or talazoparib±PDGF. In the absence of WE, PDGF induces HDF proliferation, whereas in the presence of WE #78, PDGF has no effect. Veliparib (10 µM) and talazoparib (1 µM) have no or even an inhibitory effect on fibroblasts on their own in the absence of WE, but induce proliferation in the presence of WE #78. Surprisingly, this effect is additively or synergistically enhanced by PDGF (20 ng/ml). The results are summarized as follows: 1. In the presence of WE, veliparib and talazoparib surprisingly enhance HDF proliferation. 2. When PDGF was combined with either veliparib or talazoparib, surprisingly the combination with the protein growth factor was better than each compound alone. Therefore, veliparib and talazoparib are surprisingly found to be useful in treating impaired skin wound healing in patients treated with protein growth factors, in particular PDGF.

FIG. 15: shows 2D fibroblast (human dermal fibroblast (HDF) proliferation) culture results with wound exudate #78: veliparib, olaparib, rucaparib or talazoparib±PDGF. In the presence of wound exudate #78, veliparib, olaparib, rucaparib and talazoparib show a dose-dependent increase of HDF proliferation, which is even further enhanced by the addition of PDGF, which, on its own, is inactive in the presence of WE #78. (Diamonds: PARP inhibitor compound in medium+WE #78; circles: PARP inhibitor compound+PDGF, 20 ng/ml, in medium+WE #78). Therefore, veliparib, olaparib, rucaparib and talazoparib are surprisingly found to be useful in treating impaired skin wound healing in patients treated with protein growth factors, in particular PDGF.

FIG. 16: shows 2D fibroblast (human dermal fibroblast (HDF) proliferation) culture results without and with wound exudates #91 and #55 in the absence and presence of TGF-ß (20 ng/ml) to induce myofibroblast differentiation or talazoparib (0.1 µM). In the absence of wound exudate (A-B), TGF-ß increases the staining for the myofibroblast marker alpha-smooth muscle actin (α-SMA). In the presence of wound exudates #91 and #55 (C-F), talazoparib alone is able to induce expression of α-SMA, an indicator of wound contractility.

FIG. 17: shows results of a fibroblast-macrophage coculture experiment with wound exudate #78: veliparib (VELD, talazoparib (TALAZO), niraparib (NIRA) and 3-AB. A) The percentage of live cells in the FACS CD45-gate (corresponding to macrophages), which is reduced upon incubation with wound exudate, is dose-dependently increased by veliparib and talazoparib, but not by niraparib and 3-AB. B) The same is true for the macrophage M2 marker CD206. C) The proinflammatory cytokine IL-1α, however, induced by wound exudate, is only reduced by veliparib and talazoparib, but not by niraparib or 3-AB.

FIG. 18: shows wound exudate-induced pig wounds on day 10, after 5 days of compound treatment. A) delayed healing induced by wound exudate #91, treated with vehicle, B) normal wound healing, C) delayed healing induced by wound exudate #91, treated with 10 mM veliparib, and D) delayed healing induced by wound exudate #91, treated with 1 mM talazoparib. F) Time course of delayed pig wound healing, induced by WE #91: day 5, last induction with wound exudate; day 6, first day of treatment with vehicle (open symbols), veliparib 10 mM (closed circles) or talazoparib 1 mM (closed triangles); day 10, last day of treatment; day 12, last day of observation. Both veliparib and talazoparib improve wound healing.

Figure 19:
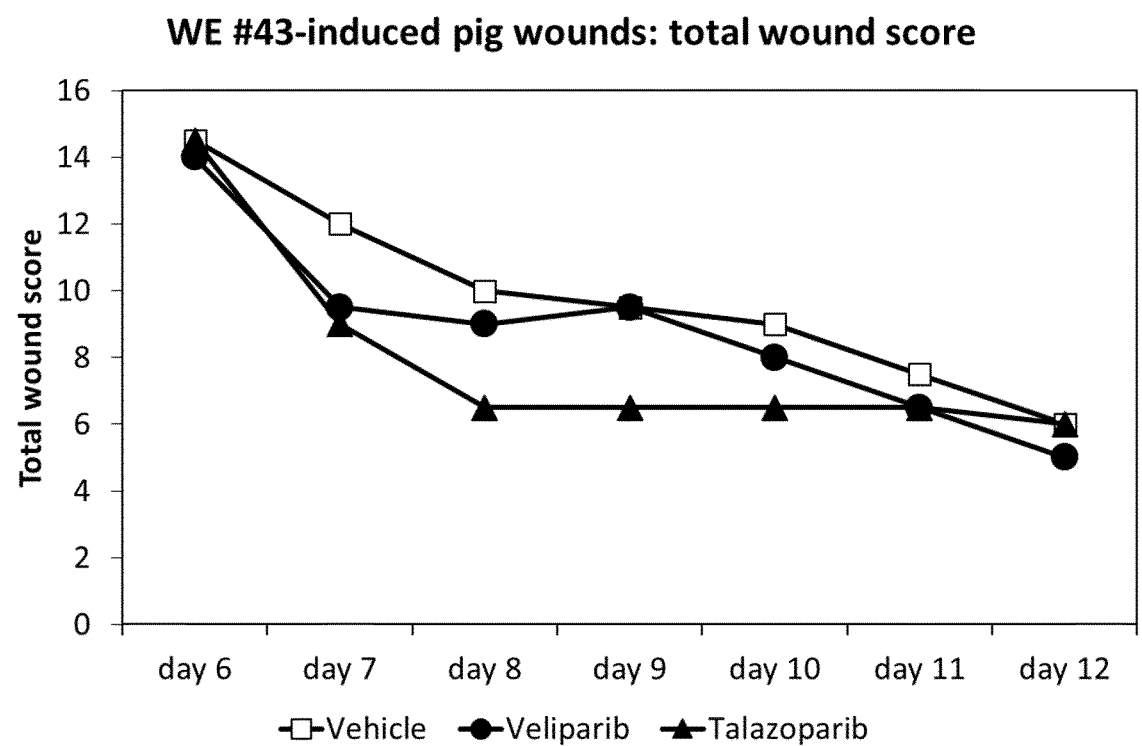

FIG. 19: shows the time course of delayed pig wound healing, induced by WE #43: day 6, first day of treatment with vehicle (open symbols), veliparib 10 mM (closed circles) or talazoparib 1 mM (closed triangles); day 10, last day of treatment; day 12, last day of observation. Talazoparib improves wound healing, while veliparib has only a minor effect with this wound exudate.

Figure 20:
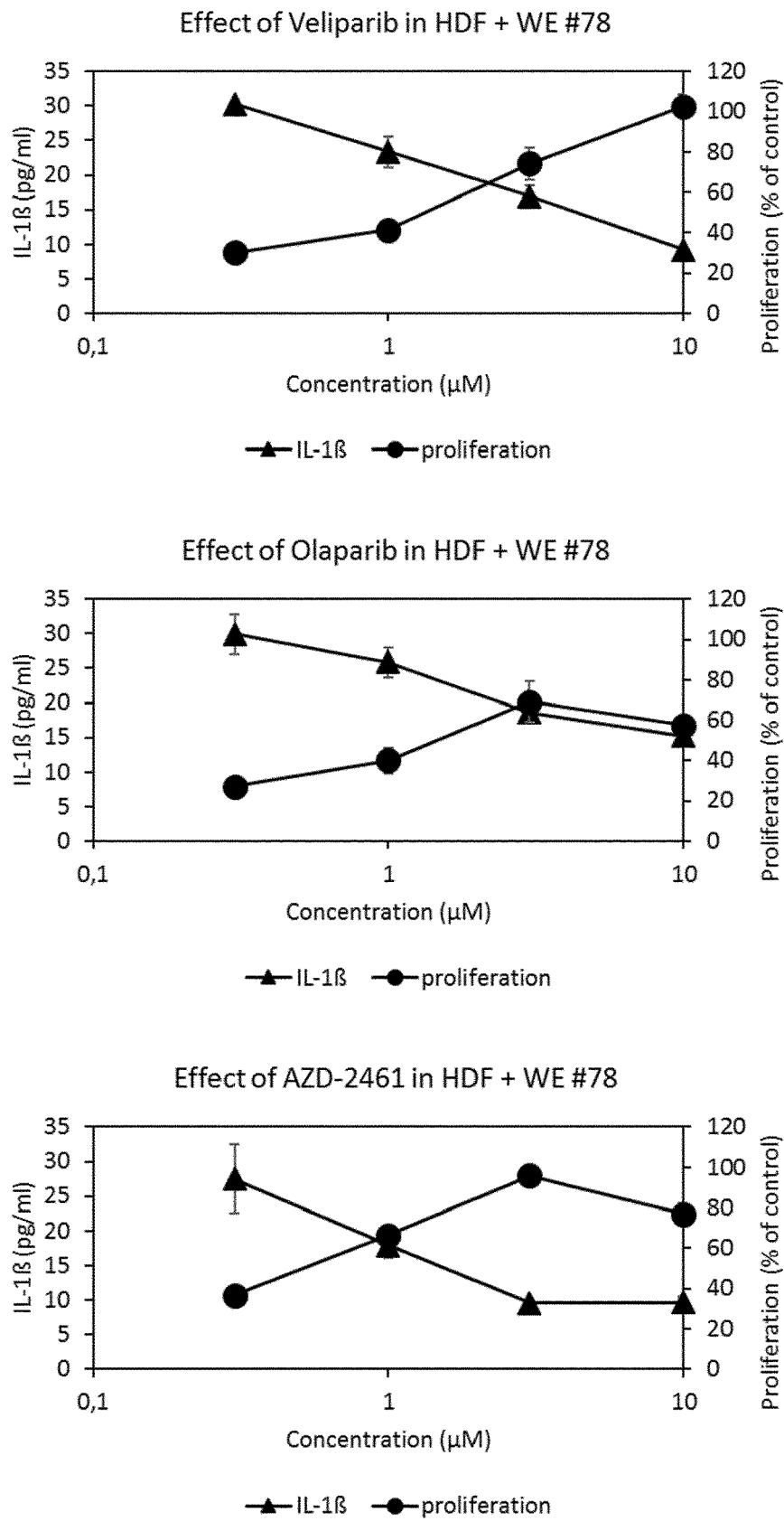
Figure 20:
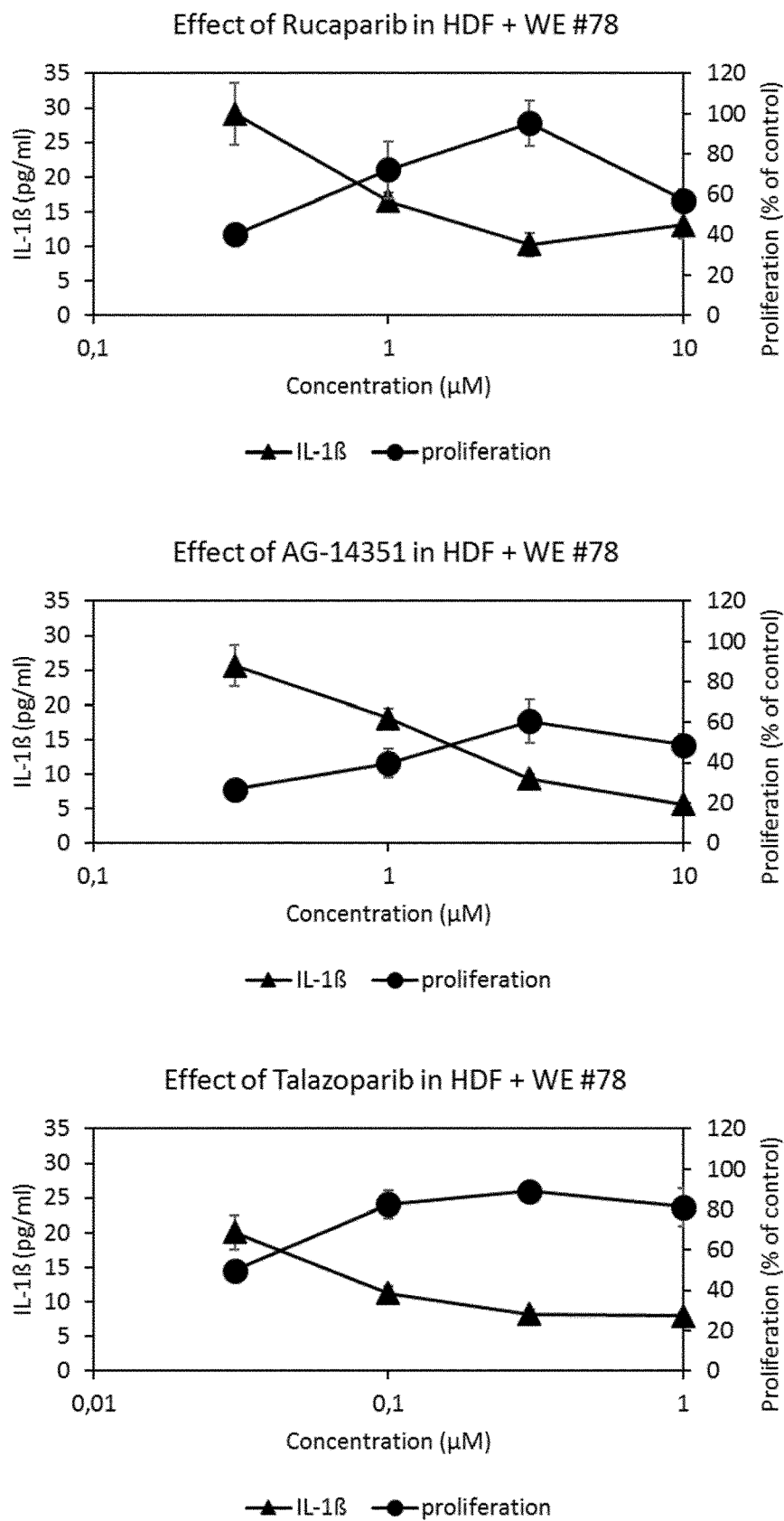
Figure 20:
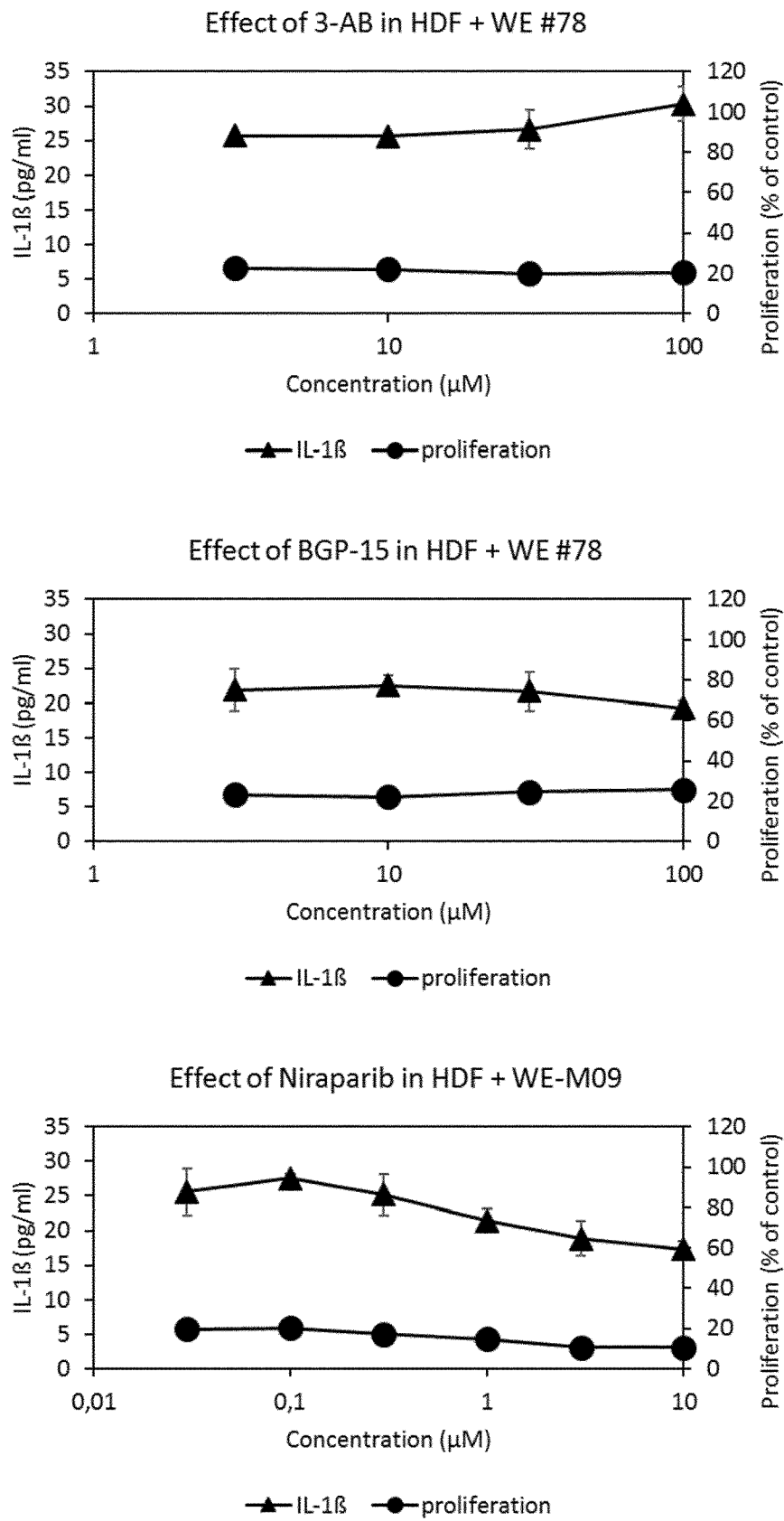

FIG. 20: shows the effects of different PARP inhibitors on wound exudate-induced inhibition of fibroblast proliferation and induction of IL-1ß secretion. The compounds veliparib, olaparib, AZD-2461, rucaparib, AG-14351 and talazoparib enhanced cell proliferation while at the same time reducing IL-1ß secretion. The inhibitors niraparib, 3-AB and BGP-15 did not show any of these effects.

EXAMPLES

Example 1: Assays Used in the Invention

Abbreviations

Abbreviation Description
bFGF Basic fibroblast growth factor
DMSO Dimethylsulfoxide
EC Endothelial cells
FACS Fluorescence activated cell sorting
FCS Fetal calf serum
FDM Fibroblast-derived matrices
FGF10 Fibroblast growth factor 10 (KGF2)
HaCaT Human keratinocyte cell line
HBSS Hank's balanced salt solution
HDF Human dermal fibroblasts
hEGF Human epidermal growth factor
HGF Hepatocyte growth factor
hIGF-1 Human insulin-like growth factor-1
hVEGF Human vascular endothelial growth factor
KGF2 Keratinocyte growth factor 2 (FGF10)
M-CSF Macrophage colony stimulating factor
PBS Phosphate buffered saline PDGF-BB Platelet-derived growth factor
RPMI Roswell Park Memorial Institute medium
SRB Sulforhodamine B
TGFbeta Transforming growth factor beta (TGF-ß)
WE Wound exudate The assays described in Examples 1.1 and 1.2 represent predictive models for skin wound healing. Most of the non-healing wound exudates (WE) obtained from a variety of patients inhibit proliferation of primary human fibroblasts (HDF) in the assay as described in Example 1.1 and also inhibit the formation of fibroblast-derived matrices (FDM) in 3D, as described in Example 1.2. Approximately one third of the WE enhance FDM formation; most of these WE are from 2 patients.

Example 1.1: Primary Human Dermal Fibroblast (HDF) Proliferation Assay: Measuring the Proliferation of Primary Fibroblast Cells and the Secretion of IL-1ß in the Presence of a Wound Exudate Sample Obtained from a Skin Wound of an Individual Primary human dermal fibroblasts (HDF) were purchased from CELLnTEC, Bern. They were routinely grown in Dulbecco's modified Eagle's medium (DMEM) containing 10% FCS, 2 mM glutamine, and 100 U/ml penicillin/100 μg/ml streptomycin. Media, antibiotics, and glutamine were bought from Lonza. The cells were used at passage 5-15. Cells were trypsinized and seeded at 5000 cells/well in 200 μl into the inner wells of 96-well plates. The outer wells were loaded with sterile water. The cells were allowed to adhere overnight and then incubated for 72 hours at 37° C. under the following conditions: graded compound concentrations or 20 ng/ml PDGF-BB (Tonbo Biosciences) in the absence or presence of different dilutions of sterile-filtered WE in medium. For control samples, 200 μl medium was added instead of specific stimuli. Alternatively, the cells were seeded into 384-well plates at 2500 cells/well directly together with test compounds or growth factors and WE or medium in a total volume of 50pl.

At the end of the 72-hour incubation period, supernatants were removed for the determination of IL-1ß, and the cells were fixed with 4% paraformaldehyde (Morphisto) for 15 minutes at room temperature and washed 3 times with PBS. A control plate was fixed after the overnight adherence of the cells (day 1) to determine the starting cell number.

Total cellular protein was determined as a measure of cell number by staining the fixed cells with sulforhodamine B (SRB, Sigma). A 0.4% SRB solution in 1% acetic acid was added to the wells for 30 minutes. The wells were then washed with 1% acetic acid until the wash solution remained colorless. After drying, the dye was eluted with 10 mM Tris.HCl, pH8.5, and absorbance was measured either at 550 or 492 nm for lower and higher cell densities, respectively. The average absorbance of the sample representing the day 1 starting cell number (for 96-well plates) was subtracted from the absorbance values of the WE-treated cells.

IL-1ß levels were determined with a commercial ELISA kit. The amount of IL-1ß contained in the wound exudate added to the cells was subtracted from the total IL-ß in the supernatants in order to determine the cytokine secreted by the cells.

All experiments were carried out in triplicate for each sample and concentration, and means±standard deviation (SD) were used for the evaluation of the experiment. Results are expressed as percentage of control values for unstimulated cells.

Example 1.2: Measuring the Fibroblast-Derived Matrix Formation (FDM) by Primary Fibroblast Cells: Measuring the Fibroblast-Derived Matrix Formation by Primary Fibroblast Cells in the Presence of a Wound Exudate Sample Obtained from a Skin Wound HDF cells were seeded at 5000 cells/well on day −3 into 96-well tissue culture plates (1250 cells/well for 384-well plates), which had been pre-coated for 1 hour at 37° C. with 0.2% gelatin solution (Sigma). When the cells reached confluence (=day 0), a matrix promoting supplement (vitamin C: 2-phospho-L-ascorbic acid trisodium salt, 100 μg/ml; Sigma) was added together with test samples containing PDGF-BB, TGF-ß1 or graded concentrations of compounds −/+WE as described for the HDF proliferation assay. After 4 days, medium was replaced by fresh vitamin C—and stimulus—as well as compound-containing medium, maintaining the conditions initiated on day 0. TGF-ß1 and PDGF-BB were included as positive controls to promote FDM formation and cell growth, respectively. After a total incubation time of 8 days, FDM production was measured in fixed cultures via SRB staining and evaluated as described above. In some cases, the experiment was stopped and evaluated already on day 4.

Example 1.3: Keratinocyte Proliferation Assay: Measuring the Proliferation of Keratinocyte Cells in the Presence of a Wound Exudate Sample Obtained from a Skin Wound The HaCaT keratinocyte cell line was routinely cultured in DMEM containing 10% FCS, 2 mM glutamine, and 100 U/ml penicillin/100 μg/ml streptomycin. The proliferation assay was carried out as described for HDF cells. Primary human keratinocytes were grown in KBM medium (Lonza) containing 0.06 mM calcium and supplemented with growth factors (Lonza) on plastic coated with rat tail collagen (40 μg/ml; Gibco) or gelatin (0.2%; Sigma). No antibiotics were used. The proliferation assay was carried out as described for HDF cells.

Example 1.4: Primary Human Dermal Microvascular Endothelial Cell Proliferation Assay: Measuring the Proliferation of Endothelial Cells in the Presence of a Wound Exudate Sample Obtained from a Skin Wound The primary human endothelial cells HMVEC-d-(Lonza) were cultured in EGM-2-MV BulletKit medium (Lonza). The proliferation assay was carried out as described for HDF cells.

Example 1.5: Primary Human Macrophage Stimulation Assay

Primary human macrophages were differentiated from monocytes, which had been isolated from peripheral blood mononuclear cells (PBMC). PBMC were isolated from buffy coats obtained from the Red Cross, Vienna, using LymphoPrep (Technoclone). 30 ml of buffy concentrate was diluted 1:2 with PBS, gently underlayered with 15 ml Lymphoprep in a 50 ml falcon tube and centrifuged for 25 minutes at 1800 rpm at 21° C. The interphase was carefully transferred to a new falcon tube and filled up to 50 ml with ice cold PBS. After another centrifugation step (10 minutes, 1200 rpm, 4° C.), the cell pellet was washed 3 times with PBS, resuspended in RPMI medium containing 20% FCS and 10% DMSO and frozen in liquid nitrogen. Monocytes were generated from frozen aliquots using positive selection with the CD14 Beads-Kit (Miltenyi) on an autoMACS-Sorter (Miltenyi) according to the manufacturer's instructions.

For culture and differentiation into macrophages, monocytes were seeded at 3-5×10$^6$ monocytes/well in 6-well-plates (Nunc) and incubated with 20 ng/ml M-CSF (R&D Systems) in RPMI supplemented with 10% FCS, 2 mM glutamine, and 100 U/ml penicillin/100 µg/ml streptomycin in a total volume of 5 ml per well. After 2 days, 2 ml of the supernatant were removed and replaced by 2.5 ml/well of fresh medium containing 20 ng/ml M-CSF. On the third day, microscopic examination revealed differentiation into adherent, frequently elongated cells.

The macrophages were harvested and re-seeded in 200 µl or 50 µl serum-free medium on 96-well or 384-well plates, respectively, combining cells with graded concentrations of test compounds in the absence or presence of various dilutions of sterile-filtered WE.

A combination of 100 ng/ml LPS (Sigma) and 50 ng/ml IFN-γ (PeproTech) served as positive control for the induction of cytokine secretion. For negative control samples, medium was added instead of specific stimuli.

After 24 hours, the supernatants were transferred to fresh plates and frozen at −20° C. for future cytokine analysis (IL-1α, IL-1ß, IL-6, TNF-α). The cytokine concentration of the input WE was subtracted from the supernatant levels in order to calculate WE-induced cytokine stimulation.

Example 1.6: Human Monocyte-Dermal Fibroblast Co-Cultures as In Vitro Models that Reflect Macrophage Behavior in Human Skin measuring (a) the amount(s) of one or more M1 marker(s) and one or more M2 marker(s) in the supernatant of macrophages incubated with a wound exudate sample obtained from a skin wound, wherein the macrophages are in co-culture with fibroblasts, and (b) measuring the amount(s) and/or frequency distribution(s) of one or more M1 cell surface marker(s) and one or more M2 cell surface marker(s) on macrophages incubated with a wound exudate sample obtained from a skin wound, wherein the macrophages are in co-culture with fibroblasts, (c) measuring the expression level(s) of one or more M1 marker mRNA(s) and one or more M2 marker mRNA(s) in macrophages incubated with a wound exudate sample obtained from a skin wound, wherein the macrophages are in co-culture with fibroblasts and (d) the amount(s) of one or more cytokine markers selected from IL-1alpha, IL-1beta and TNF-alpha in the supernatant of macrophages incubated with a wound exudate sample obtained from a skin wound, wherein the macrophages are in co-culture with fibroblasts CD14$^+$ monocytes, isolated from PBMC of healthy donors by magnetic bead separation were incubated either alone or in the presence of primary human dermal fibroblasts (CellNTec) or fibroblast-derived matrices (FDM). FDM had been generated from primary human dermal fibroblasts by a 3-week incubation with the growth supplements vitamin C or insulin and EGF (vitamin C: 2-phospho-L-ascorbic acid trisodium salt, 100 µg/ml; human EGF, 5 ng/ml; human insulin, 5 µg/ml). Alternatively, fibroblast monolayer cultures can be used as well. After 4 days to a week to allow for macrophage differentiation in the presence or absence of M-CSF (25 ng/ml), the cultures were stimulated overnight with graded concentrations of test compounds in the absence or presence of various dilutions of sterile-filtered WE. IFN-g (50 ng/ml), LPS (100 ng/ml) and IL-4 (25 ng/ml) or combinations thereof served as controls for M1 and M2 macrophage induction. For negative control samples, medium was added instead of specific stimuli. WE were added to the culture medium for overnight stimulation at dilutions ranging from 1:25 to 1:100.

Supernatants were harvested and frozen for cytokine determination by ELISA, and cells were harvested and subjected to FACS analysis, gating on the monocyte population. Geometric means or mean fluorescence intensities (MFI) were used to quantify surface marker expression.

Specific mRNA levels are determined as ratios compared to a housekeeping gene; the values obtained are "expression relative to housekeeping gene".

There are 2 possibilities for evaluation: a) the % of cells positive for a given marker within a population, which is the most commonly used readout in FACS analysis, or b) the quantity of cell surface expression (as surrogate for the number of labelled molecules on the cell surface per individual cell), as measured by the mean fluorescence intensity. The following readouts were used:

FACS: CD38, CD64 and CD197 for M1 macrophages, CD200 receptor (CD200R), CD206 and CD209 for M2 macrophages, CD163 as a marker of macrophage differentiation. Ratios of M1/M2 cell surface marker expression were calculated.

ELISA: CXCL10 and IL-23p19 for M1 macrophages and CCL22 and CCL18 as M2 macrophage markers, IL-1alpha, IL-1beta and TNF-alpha as pro-inflammatory markers indicative of an M1 phenotype.

mRNA: CD38, CD64 CD38, CD64 and CD197 for M1 macrophages, CD200 receptor (CD200R), CD206 and CD209 for M2 macrophages, CD163 as a marker of macrophage differentiation.

Example 1.7: Determination of CCL18

CCL18 in WE and in macrophage supernatants was determined in F96 Maxisorp Nunc Immuno plates (Nunc, #439454) using the hCCL18/PARC DuoSet ELISA Kit from R&D Systems (#DY394) according to the manufacturer's instructions. Enzyme reaction and measurement were performed as described for IL-1a.

Example 1.8: Analysis of Macrophage Surface Markers by Flow Cytometry

Cells were harvested and resuspended in FACS buffer (PBS containing 2% FCS). Unspecific antibody binding was prevented by incubation with human Trustain FCR blocking solution (Biolegend, #422302) on ice for 10 minutes. The following fluorchrome-conjugated antibodies from eBioscience (now ThermoFisher Scientific) were used to detect specific surface markers by staining on ice for 30 minutes: CD38-PerCPeFluor710 (#46-0388-42), CD197-APC (#17-1979-42), CD206-AF488 (#53-2069-42), CD209-PerCP Cy5.5 (#45-2099-42). Co-staining with CD45 eFluor (#506 69-0459-42) was used to distinguish macrophages from primary human fibroblasts when analyzed from co-cultures. After washing cells with FACS buffer, they were fixed with 1% paraformaldehyde in PBS and stored at 4° C. in the dark until data were acquired on a Gallios flow cytometer from Beckman Coulter and analyzed with the Kaluza analysis software 1.3.

Example 1.9: Immunolocalization of Alpha-Smooth Muscle Actin

After fixation with paraformaldehyde, the cells were incubated for 1 hour at room temperature with a monoclonal mouse-anti-human antibody against alpha-smooth muscle actin (α-SMA) from e-Bioscience, washed 3 times with PBS and developed with an Alexa Fluor-labelled donkey-anti-mouse IgG (Molecular Probes). The cells were washed 3 times with PBS and examined in a Zeiss ZEISS Observer.Z1 microscope, using the software AxioVision 48.

Example 1.10: Porcine Model of Delayed Wound Healing Induced by Human Wound Exudates The pig is regarded as the species with the highest correlation to man in skin anatomy and physiology. Pig wounds tend to heal by a combination of granulation tissue formation and contraction, similar to human wounds, and porcine wound healing studies show a high concordance with human studies. We developed a chronically inflamed porcine wound model. Acute pig wounds were stimulated by a combination of human chronic wound fluids and the toll-like receptors 7 and 8 (TLR7,8) agonist resiquimod (R848).

Female domestic white pigs at the age of 10-12 weeks and a body weight of approximately 12 kg were sedated with 20 mg Ketamin/2 mg Xylacin i.m. followed by inhalation anesthesia via Isofluran. Immediately after induction of anesthesia, a fentanyl transdermal patch (50 μg/h) was applied to control postsurgical pain. The fentanyl patch was replaced daily for the first 3 days after surgery and afterwards only when signs of pain were apparent. Before wounding, the back hair of the animals was clipped and the skin was cleaned with Braunol and disinfected with Skinsept. Then a total of 24 full-thickness excisional wounds per animal were applied using a 6 mm disposable biopsy punch. Immediately after wounding 50 μl of a 0.05% R848 gel was applied topically to the wounds which were covered with dressing (Mölnlycke Health Care AB, Sweden). 6 hours later, the wounds were treated with 3% HPMC (hydroxypropyl methylcellulose)-gellified human wound exudates or human serum as controls. Wound exudates had been harvested from negative pressure wound therapy systems used to treat patients diagnosed with chronic ulcers. Induction of wound inflammation by R848 and wound exudate was carried out for a total of 5 consecutive days.

From day 6 to day 10, veliparib and talazoparib at 10 mM and 1 mM, respectively, were dissolved in vehicle (50% propylene glycol/47.5% water/0.5% Tween 80/2.0% HPMC), applied to the wounds once daily and covered with dressing. Until day 12, wounds and surrounding skin were clinically examined once daily, upon dressing change, and observed changes were scored on a scale from 0-3. The following criteria were used:

Wound:
1) Moist=1, Dry=0
2) Filled with granulation tissue: empty=1, partially or completely filled=0
3) Purulent content/crust: no=0 to severe=3
4) Eschar formation: no=2, partially covered=1, fully covered=0

Surrounding skin:
1) Erythema: no=0 to severe=3
2) Swelling: no=0 to severe=3
3) Dark blueish color change: no=0 to severe=3
4) Yellowish-white color change: no=0 to severe=3

The total achievable score (non-healing) is 19. Healing is associated with low scores.

Example 1.11: Test Compounds

Low molecular weight compounds (see list in Table 1) were dissolved in DMSO (Bioreagent for cell culture, Sigma) at 10 mM or 100 mM and diluted at least 1:1000 in medium for cellular assays (final DMSO concentration ≤0.1%). Compounds were typically tested in half-logarithmic dilution series (1:3.33), starting at 10 μM or 100 μM as the highest compound concentration.

Protein growth factors (see list in Table 1) were dissolved according to the manufacturers' recommendations and used at final concentrations ranging from 0.02 to 1000 ng/ml.

Cells were incubated with compounds for 72 hours in proliferation assays and up to 8 days for FDM assay (refreshed after 4 days). When compounds were tested for their effect on WE stimulation, the incubation of cells with compounds was started and ended simultaneously with WE-incubation.

TABLE 1

List of low molecular weight compounds and protein growth factors for cellular assays

| Compound | Source |
|---|---|
| Dexamethasone 21-acetate | Sigma-Aldrich |
| Prednisolone | Sigma-Aldrich |
| Hydrocortisone | Lonza |
| Medroxyprogesterone | MedChem Express |
| Progesterone | MedChem Express |
| Veliparib dihydrochloride | MedChem Express |
| Olaparib | MedChem Express |
| AZD-2461 | MedChem Express |
| Niraparib | MedChem Express |
| Rucaparib phosphate | MedChem Express |
| Talazoparib | MedChem Express |
| PJ-34 hydrochloride | Cayman Chemical |
| 1,5-Isoquinolinediol | Cayman Chemical |
| 3-Aminobenzamide | Cayman Chemical |
| BGP-15 | Cayman Chemical |
| PDGF | Tonbo Biosciences |
| bFGF | eBioscience |
| TGFbeta | eBioscience |
| HGF | R&D Systems |
| hEGF | Gibco |
| hIGF-1 | Gibco |
| FGF10 (KGF2) | R&D Systems |
| hVEGF | Gibco |

The invention claimed is:

1. A method for treating impaired skin wound healing in a human subject, the method comprising administering a therapeutically effective amount of Veliparib, or a pharmaceutically acceptable salt thereof, to a chronic wound of the subject, wherein the wound comprises chronic wound exudate.

2. The method of claim 1, wherein the chronic wound is selected from a wound of a diabetic patient, a skin wound which is infected by at least one microorganism, an ischemic wound, a wound in a patient suffering from deficient blood supply or venous stasis, an ulcer, a neuropathic wound, ulcus cruris, surgical wound, burn, dehiscence, neoplastic ulcer, a bullous skin disease, and rare ulcer.

3. The method of claim 1, wherein the subject suffers from at least one co-morbidity associated with impaired skin wound healing, in particular diabetes, and/or wherein the subject is treated with at least one immunosuppressive drug.

4. The method of claim 1, wherein the subject suffers from diabetes and/or has at least one diabetic ulcer.

5. The method of claim 1, wherein the subject:
   (i) is a subject treated with at least one glucocorticoid, and/or
   (ii) is a subject to which a pharmaceutical, nutritional supplement or dietary supplement comprising ascorbic acid or a pharmaceutically acceptable salt thereof is administered, and/or
   (iii) is a subject treated with at least one protein growth factor.

6. The method of claim 1, wherein the subject:
   (i) has undergone transplantation of a graft, and/or
   (ii) obtains immunosuppressive therapy,
   and optionally suffers from diabetes.

7. The method of claim 1, wherein the subject is identified to be responsive to the treatment of impaired skin wound healing by performing steps i) and/or ii):
   i) measuring the proliferation of primary fibroblast cells in the presence of:
      (1) a wound exudate sample obtained from the chronic wound of said subject, and
      (2) Veliparib or a pharmaceutically acceptable salt thereof;
   ii) measuring the fibroblast-derived matrix formation by primary fibroblast cells in the presence of:
      (1) a wound exudate sample obtained from the chronic wound of said subject, and
      (2) Veliparib or a pharmaceutically acceptable salt thereof.

8. The method of claim 7, wherein the subject is identified to be responsive to the treatment of impaired skin wound healing with Veliparib, or a pharmaceutically acceptable salt thereof, in case the value of proliferation of primary fibroblast cells measured in step i) and/or the value of the fibroblast-derived matrix formation by primary fibroblast cells measured in step ii) is at least 20% above a control value established in the absence of Veliparib or a pharmaceutically acceptable salt thereof.

9. The method of claim 7, wherein, in addition, step iiia) and/or one, two, three or four of the following steps iiib) to iiie) are performed:
   iiia) measuring the proliferation of keratinocyte cells in the presence of:
      (1) a wound exudate sample obtained from the chronic wound of said subject, and
      (2) Veliparib or a pharmaceutically acceptable salt thereof;
   iiib) measuring the amount(s) of one or more M1 marker(s) and one or more M2 marker(s) in the supernatant of macrophages incubated with
      (1) a wound exudate sample obtained from said chronic wound, and
      (2) Veliparib or a pharmaceutically acceptable salt thereof;
   wherein the macrophages are in co-culture with fibroblasts, and
   wherein the one or more M1 markers are selected from CXCL10 and IL-23p19, and the one or more M2 markers are selected from CCL22 and CCL18,
   iiic) measuring the amount(s) and/or frequency distribution(s) of one or more M1 cell surface marker(s) and one or more M2 cell surface marker(s) on macrophages incubated with
      (1) a wound exudate sample obtained from said chronic wound, and
      (2) Veliparib or a pharmaceutically acceptable salt thereof;
   wherein the macrophages are in co-culture with fibroblasts, and
   wherein the one or more M1 cell surface markers are selected from CD38, CD64 and CD197, and wherein the one or more M2 cell surface markers are selected from CD200 receptor, CD206 and CD209,
   iiid) measuring the expression level(s) of one or more M1 marker mRNA(s) and one or more M2 marker mRNA(s) in macrophages incubated with
      (1) a wound exudate sample obtained from said chronic wound, and
      (2) Veliparib or a pharmaceutically acceptable salt thereof;
   wherein the macrophages are in co-culture with fibroblasts, and
   wherein the one or more M1 marker mRNA(s) are selected from CD38, CD64, CD197, CXCL10 and IL-23p19, and the one or more M2 marker mRNA(s) are selected from CD200 receptor (CD200R), CD206, CD209, CCL22 and CCL18,
   iiie) measuring the amount(s) of one or more cytokine markers in the supernatant of macrophages incubated
      (1) with a wound exudate sample obtained from said chronic wound, and
      (2) Veliparib or a pharmaceutically acceptable salt thereof;
   and
   wherein the one or more cytokine markers are selected from IL-1alpha, IL-1beta and TNF-alpha,
   and
   wherein the subject is identified to be responsive to the treatment with Veliparib, or a pharmaceutically acceptable salt thereof, in case the value of proliferation of primary fibroblast cells measured in step i) and/or the value of the fibroblast-derived matrix formation by primary fibroblast cells measured in step ii) and/or the value of the proliferation of keratinocyte cells in step iiia) is at least 20% above a control value established in the absence of the compound(s) of (2), and/or in case one or more of the following applies:
   the ratio of amount(s) of one or more M1 marker(s) to the amount(s) of one or more M2 marker(s) obtained in iiib) is/are below a control value established in the absence of Veliparib or a pharmaceutically acceptable salt thereof,
   the ratio of amount(s) and/or frequency distribution(s) of one or more M1 cell surface marker(s) to the amount(s) and/or frequency distribution(s) of one or more M2 cell surface marker(s) obtained in iiic) is/are below a control value established in the absence of Veliparib or a pharmaceutically acceptable salt thereof,
   the ratio of expression level(s) of one or more M1 marker mRNA(s) to the expression level(s) of one or more M2 marker mRNA(s) obtained in iiid) is/are below a control value established in the absence of Veliparib or a pharmaceutically acceptable salt thereof, the value obtained in iiie) is below a control value established in the absence of Veliparib or a pharmaceutically acceptable salt thereof.

10. The method of claim 1, wherein Veliparib or the pharmaceutically acceptable salt thereof is
  (i) formulated for systemic, preferably oral or intravenous administration, or
  (ii) formulated for local administration, in particular for topical, mucosal or subcutaneous administration.

11. The method of claim 5, wherein the glucocorticoid is selected from the group consisting of cortisol, cortisone acetate, prednisone, prednisolone, methylprednisolone, chloroprednisone, cloprednol, difluprednate, fludrocortisone acetate, fluocinolone, fluperolone, fluprednisolone, loteprednol, prednicarbate, tixocortol, triamcinolone, triamcinolone acetonide, dexamethasone, betamethasone, beclometasone, deoxycorticosterone acetate, alclometasone, clobetasol, clobetasone, clocortolone, desoximetasone, diflorasone, difluocortolone, fluclorolone, flumetasone, fluocortin, fluocortolone, fluprednidene, fluticasone, fluticasone furoate, halometasone, meprednisone, mometasone, mometasone furoate, paramethasone, prednylidene, rimexolone, ulobetasol, amcinonide, budesonide, ciclesonide, deflazacort, desonide, formocortal, fluclorolone acetonide, fludroxycortide, flunisolide, fluocinolone acetonide, fluocinonide, halcinonide, hydroxymethylprogesterone, and medroxyprogesterone, or a pharmaceutically acceptable salt thereof, and/or wherein the subject is treated with at least one glucocorticoid by systemic or cutaneous administration.

12. The method of claim 5, wherein the protein growth factor is a human protein growth factor and/or wherein the protein growth factor is selected from a platelet derived growth factor (PDGF), transforming growth factor beta (TGF-ß), basic fibroblast growth factor (bFGF), keratinocyte growth factor (KGF), epidermal growth factor (EGF), Insulin-like growth factor 1 (IGF-1), vascular endothelial growth factor (VEGF) and hepatocyte growth factor (HGF).

* * * * *